(12) United States Patent
Ross

(10) Patent No.: US 9,522,187 B2
(45) Date of Patent: *Dec. 20, 2016

(54) CANCER THERAPY USING BETA GLUCAN AND ANTIBODIES

(71) Applicants: University of Louisville Research Foundation, Inc., Louisville, KY (US); Trunetta Jo Dockter Ross

(72) Inventor: Gordon D. Ross, Prospect, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/528,900

(22) Filed: Oct. 30, 2014

(65) Prior Publication Data

US 2015/0064199 A1    Mar. 5, 2015

Related U.S. Application Data

(63) Continuation of application No. 10/526,185, filed as application No. PCT/US03/27975 on Sep. 4, 2003, now Pat. No. 8,883,760.

(60) Provisional application No. 60/408,126, filed on Sep. 4, 2002.

(51) Int. Cl.
| | | |
|---|---|---|
| *A61K 31/715* | (2006.01) | |
| *A61K 31/47* | (2006.01) | |
| *A61K 39/395* | (2006.01) | |
| *A61K 31/716* | (2006.01) | |
| *A61K 39/00* | (2006.01) | |

(52) U.S. Cl.
CPC ......... *A61K 39/39558* (2013.01); *A61K 31/47* (2013.01); *A61K 31/715* (2013.01); *A61K 31/716* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 3,903,297 A | 9/1975 | Robert | |
| 3,943,247 A | 3/1976 | Komatsu et al. | |
| 4,138,479 A | 2/1979 | Truscheit et al. | |
| 4,237,266 A | 12/1980 | Sugiura et al. | |
| 4,492,540 A | 1/1985 | Yamamoto | |
| 4,707,471 A | 11/1987 | Larm et al. | |
| 4,739,046 A | 4/1988 | DiLuzio et al. | |
| 4,761,402 A | 8/1988 | Williams et al. | |
| 4,810,646 A | 3/1989 | Jamas et al. | |
| 4,818,752 A | 4/1989 | Williams et al. | |
| 4,900,722 A | 2/1990 | Williams et al. | |
| 4,946,450 A | 8/1990 | Erwin | |
| 4,975,421 A | 12/1990 | Williams et al. | |
| 4,992,540 A | 2/1991 | Jamas et al. | |
| 5,028,703 A | 7/1991 | Jamas et al. | |
| 5,032,401 A | 7/1991 | Jamas et al. | |
| 5,037,972 A | 8/1991 | Jamas et al. | |
| 5,057,503 A | 10/1991 | Czop et al. | |
| 5,082,936 A | 1/1992 | Jamas et al. | |
| 5,130,127 A | 7/1992 | Herlyn | |
| 5,221,616 A | 6/1993 | Kolb et al. | |
| 5,223,409 A | 6/1993 | Ladner et al. | |
| 5,223,491 A | 6/1993 | Donzis | |
| 5,250,436 A | 10/1993 | Jamas et al. | |
| 5,320,849 A | 6/1994 | Hagiwara et al. | |
| 5,322,841 A | 6/1994 | Jamas et al. | |
| 5,397,773 A | 3/1995 | Donzis et al. | |
| 5,401,647 A | 3/1995 | Tanaka et al. | |
| 5,453,124 A | 9/1995 | Moslehi et al. | |
| 5,474,984 A | 12/1995 | Tanaka et al. | |
| 5,488,040 A * | 1/1996 | Jamas ................... | A61K 31/715 514/54 |
| 5,504,079 A | 4/1996 | Jamas et al. | |
| 5,506,124 A | 4/1996 | Jamas et al. | |
| 5,532,223 A | 7/1996 | Jamas et al. | |
| 5,576,015 A | 11/1996 | Donzis | |
| 5,607,677 A | 3/1997 | Jamas et al. | |
| 5,622,939 A | 4/1997 | Jamas et al. | |
| 5,622,940 A | 4/1997 | Ostroff | |
| 5,633,369 A | 5/1997 | Jamas et al. | |

(Continued)

FOREIGN PATENT DOCUMENTS

| | | |
|---|---|---|
| CA | 2434938 | 8/2002 |
| CN | 1082056 | 2/1994 |

(Continued)

OTHER PUBLICATIONS

"Principles of Cancer Therapy". Cecil's Textbook of Medicine (Twenty-first Edition, vol. 1). W.B. Saunders Company, 2000. pp. 1060-1074.
"What's the Difference of Th1 Cells and Th2 Cells Effect?" Http:llwww.madsci.org/posts/archives/mav99/926272023.Im.r.. html (May 8, 1999).
Biopolymer Engineering Presentation: Pioneering Carbohydrate Technology to Improve Human Health, Apr. 2003.
Blakeslee, Dennis, "The Two Faces of Immunity: Th1 and Th2," JAMA HIV/AIDS Resource Center, The Journal of the American Medical Association, Http:llwww.ama-assn.orgfsoeciaIlhiv/ newsline/briefingfth 1.htm (Aug. 12, 2002).

(Continued)

*Primary Examiner* — Craig Ricci
(74) *Attorney, Agent, or Firm* — Fish & Richardson P.C.

(57) ABSTRACT

The present invention relates to methods of using neutral soluble glucan and monoclonal antibodies for antitumor therapy. Neutral soluble Beta (1,3; 1,6) glucan (NSG) enhances the tumoricidal activity of the innate immune system by binding to the C3 complement protein receptor CR3. The glucan does not stimulate the induction of inflammatory cytokines. Also described are methods of using whole glucan particles (WGP) as an immunomodulator by inducing a shift from a Th2 response to the Th1 response, leading to an enhanced antitumor cytotoxic T-cell response.

3 Claims, 26 Drawing Sheets

(56) References Cited

U.S. PATENT DOCUMENTS

| | | | |
|---|---|---|---|
| 5,663,324 | A | 9/1997 | James et al. |
| 5,702,719 | A | 12/1997 | Donzis |
| 5,705,184 | A | 1/1998 | Donzis et al. |
| 5,741,495 | A | 4/1998 | Jamas et al. |
| 5,766,571 | A | 6/1998 | Ceriani et al. |
| 5,783,569 | A | 7/1998 | Jamas et al. |
| 5,811,542 | A | 9/1998 | Jamas et al. |
| 5,817,643 | A | 10/1998 | Jamas et al. |
| 5,849,720 | A | 12/1998 | Jamas et al. |
| 6,235,272 | B1 | 5/2001 | Greene |
| 6,355,625 | B1 | 3/2002 | Pavliak et al. |
| 6,369,216 | B1 | 4/2002 | Patchen et al. |
| 7,462,607 | B2 * | 12/2008 | Cheung ............... A61K 31/715 424/138.1 |
| 7,507,724 | B2 | 3/2009 | Cheung |
| 7,704,973 | B2 | 4/2010 | Cheung |
| 8,883,760 | B2 | 11/2014 | Ross |
| 2004/0014715 | A1 | 1/2004 | Ostroff |
| 2004/0116380 | A1 | 6/2004 | Jamas et al. |
| 2005/0245480 | A1 | 11/2005 | Ostroff et al. |
| 2006/0009419 | A1 | 1/2006 | Ross et al. |
| 2006/0165700 | A1 | 7/2006 | Ostroff et al. |
| 2008/0193456 | A1 | 8/2008 | Cheung |
| 2009/0163439 | A1 | 6/2009 | Ross et al. |
| 2009/0169557 | A1 | 7/2009 | Ross et al. |
| 2010/0166751 | A1 | 7/2010 | Ostroff et al. |
| 2010/0216743 | A1 | 8/2010 | Cheung |
| 2010/0273867 | A1 | 10/2010 | Cheung |

FOREIGN PATENT DOCUMENTS

| | | |
|---|---|---|
| CN | 1694715 | 11/2005 |
| CN | 1697659 | 11/2005 |
| CN | 1939335 | 4/2007 |
| CN | 1964722 | 5/2007 |
| EP | 0 416 343 | 3/1991 |
| EP | 9 302 063 | 2/1994 |
| EP | 1 536 820 | 6/2005 |
| EP | 1 539 194 | 6/2005 |
| EP | 1 545 208 | 6/2005 |
| EP | 2 181 711 | 5/2010 |
| JP | 63-500805 | 3/1988 |
| JP | 5-502018 | 4/1993 |
| JP | 11-501691 | 2/1999 |
| WO | WO 91/03495 | 3/1991 |
| WO | WO 94/03500 | 2/1994 |
| WO | WO 02/058711 | 8/2002 |
| WO | WO 2004/014320 | 2/2004 |
| WO | WO 2004/021994 | 3/2004 |
| WO | WO 2004/030613 | 4/2004 |
| WO | WO 2006/085895 | 8/2006 |

OTHER PUBLICATIONS

Bogwald et al., "The Cytotoxic Effect of Mouse Macrophages Stimulated in vitro by a beta-1,3,-DGlucan from yeast Cell Walls," Scand. J Immunol., 15: 297-304 (1982).
Bohn, J.A. et al., "(1→3)-β-D-Glucans as Biological Response Modifiers: A Review of Structure-Functional Activity Relationships," Carbohydrate Polymers, 28: 3-14 (1995).
Borchers, A.T. et al., "Minireview: Mushrooms, Tumors, and Immunity," Mushrooms and Immunity, 221(4): 281-293 (1999).
Byers, T. (CA Journal, vol. 49, No. 6, Nov./Dec. 1999).
Bystryn. Cancer and Metastasis Reviews, p. 81-91. 1990.
Cain et al, "Role of Complement Receptor Type Three and Serum Opsonins in the Neutrophil Response to Yeast," Complement, 4: 75-86 (1987).
Chen et al., Abstract from "Medicinal Importance of fungal f3-(1-3),(1-6)-glucans", Mycological Research III, (2007) p. 635-652.
Cheung et al., "Orally Administered B-glucans enhance anti-tumor effects of monoclonal antibodies," Cancer Immunol Immunother, vol. 51, pp. 557-564 (2002).
Cheung, N.V. et al., "Oral (1-+3), (1-+4)-J3-D-Glucan Synergizes with Antiganglioside GD2 Monoclonal Antibody 3F8 in the Therapy of Neuroblastoma," Clinical Cancer Research: An Official Journal of the American Associationg for Cancer Research, vol. 8(5): 1217-1223 (May 2002).
Chihara, et al., "Fractionation and Purification of the Polysaccharides with Marked Antitumor Activity, Especially Lentinan, from Lentinus edodes (Berk) Sing. (an Edible mushroom)," Cancer Research, 30: 2776-2781 (1970).
Coxon, A. et al., "A Novel Role for the Beta2 Integrin CD11b/CD18 in Neutrophil Apoptosis: A Homeostatic Mechanism in Inflammation," Immunity, 5: 653-666 (1996).
Czop et al., "Production and isolation of rabbit anti-idiotypic antibodies directed against the . . . ," J Immunol, 145: 995-1001 (1990).
Czop et al., "The Role of ~-Glucan Receptors on Blood and Tissue Leukocytes in Phagocytosis and Metabolic Activation," Pathology and Immunopathology Research, 5: 286-296 (1986).
Database DRUGU on STN (Columbus, OH, USA), AN 1990-03601, Srivastava, R. et al, "Bioactive Polysaccharides from Plants," Phytochemistry, vol. 28, No. 11, pp. 2877-2883, 1989, Abstract, see entire Abstract.
Database DRUGU on STN (Columbus, OH, USA), AN 1998: 11655, Coiffier, B. et al., "A Multicenter, Randomized Phase II Study of Rituximab (Chimeric Anti-CD20 rnA b) at Two Dosages in Patients with Relapsed or Refractory Intermediate or High-Grade NHL (IHG-NHL) or in Elderly Patients in First-Line Therapy," Blood (90, No. 10, Suppl. 1 Pt 1): 510A, 1997, Abstract, see entire Abstract.
Database HCAPLUS on STN (Columbus, OH, USA), No. 137:119657, Cheung, N., "Antitumor Antibody-Enhancing Glucan," W0200205871IA1, Aug. 1, 2002, abstract, see entire abstract.
Database Medline in STN. (Columbus, OH, USA) AN 2000285552, Yadomae, T., "Structure and Biological Activities of Fungal beta-1,3-glucans," J. Pharmaceutical Soc. Jap., 120(5): 413-431 (2000), Abstract Only.
Diller, et al., "The effect of yeast polysaccharides on mouse tumors," Institute for Cancer Research, vol. 23 (Feb. 1963).
Encyclopedia article titled "Lentinan", obtained from http://en.wikipedia.org/wiki/Lentinan on Dec. 10, 2010, last updated Nov. 30, 2010 as shown by chronological record of updates to the article which is included as part of the article.
Frazer, I. (Expert. Opin. Pharmacother. 2004; 5: 2427-2434).
Gelderman et al (Trends in Immunol 25:158-164, 2004).
Granziero et al. (Eur. J. Immunol. 1999,29:1127-1138).
Gura, Science 278: 1041-1042, 1997.
Harlow, E. and Lane, D., "Using antibodies: a laboratory manual," (NY: Cold Spring Harbor Laboratory Press) (1999).
Hassid et al., "The Molecular Constitution of an Insoluble Polysaccharide from Yeast, Saccharomyces cerevisiae," Journal of the American Chemical Society, 63: 295 (1941).
Heron Herbals: Feature Articles: "Balancing Cellular and Humoral Immunity," Http://www.healthcalls.net/hh_artlalt.html (Aug. 16, 2002).
Hortobagyi (Semin Oncol28:43-47, 2001) Abstract Only.
Hotta et al., "Augmentation of Protective Immune Responses Against Sendai Virus Infection by Fungal Polysaccharide Schizophyllan," Int. J Immunopharmacol., 15(1): 55-60 (1993).
Kaiser, A.B. et al., "Synergism Between Poly-(1-6)-Beta-D-Glucopyranosyl-(1,3)-Beta-DGlucopyranose Glucan and Cefazolin in Prophylaxis of Staphylococcal Wound Infection in a Guinea Pig Model," Antimicrob. Agents Chemother., 42(9): 2449-2451 (1998).
Kournikakis et al., "Anthrax-Protective Effects of Yeast Beta 1,3 Glucans," Medscape General Medicine, Mar. 21, 2003, 4 sheets.
Leyland-Jones, Brian. "Trastuzumab: hopes and realities" The Lancet Oncology vol. 3. Mar. 2002.
Li, B., et al., "Combined Yeast B-Glucan and Antitumor Monoclonal Antibody Therapy Requires C5a-Mediated Neutrophil Chemotaxis via Regulation of Decay-Accelerating Factor CD55," Cancer Research, 67(15): 7421-7430 (2007).

(56) References Cited

OTHER PUBLICATIONS

Li, B., et al., "Yeast β-Glucan Amplifies Phagocyte Killing of iC3b-Opsonized Tumor Cells via Complement Receptor 3-Syk-Phosphatidylinositol 3-Kinase Pathway!," The Journal of Immunology, 177: 1661-1669 (2006).
Maeda, et al., "Denaturation and Renaturation of a B-1,6; 1,3-Gluean, Lentinan, Associated with Expression of T-Cell-mediated Responses," Cancer Research, 48: 671-675 (1988).
Matsuo, T. et al., "Granulopoietic Effects of Lentinan in Mice: Effects on GM-CFC and 5-FUInduced Leukopenia," Jpn. J Cancer Chemotherapy, 14: 1310-1314 (1987) (English Abstract on Last Page).
Misaki, A., "Structure of Pestalotan, A Highly Branched (1→3)-β-D-Glucan Elaborated by Pestalotia sp. 815, and the Enhancement of its Antitumor Activity by Polyol Modification of the Side Chains," Carbohydr. Res., 129: 209-227 (Jan. 1984).
Mosby's GenRx, 1998, p. 488.
Muto, Satoshi et al., "CR3 (CD11b/CD118) Expressed by Cytotoxic T Cells and Natural Killer Cells is Upregulated in a Manner Similar to Neutrophil CR3 Following Stimulation with Various Activating Agents," Journal of Clinical Immunol., 13(3): 175-184 (1993).
Nanba et al., "Antitumor Action of Shiitake (Lentinus edodes) Fruit Bodies Orally Administered to Mice," Chem. Pharm. Bull, (Tokyo), 35(6): 2453-2458 (1987).
News Release from Biothera titled "DKSH to Distribute Biopolymer Engineering Beta 1,311,6 Glucan in Europe", published Dec. 16, 2003, obtained on Dec. 9, 2010 from http:www.biothera.comlpressI12-16-03%20DKSH.htm.
Onderdonk, A. et al., "Anti-Infection Effect of Poly-Beta 1-6-Glucotriosyl-Beta 1-3-Glucopyranose Glucan in vivo," Infect. Immun., 60(4): 1642-1647 (1992).
Patchen, M.L. et al., "Comparative Effects of Soluble and Particulate Glucans on Survival in Irradiated Mice," Journal of Biological Response Modifiers, 5(1): 45-60 (1986).
Patchen, M.L. et al., "Effects of Pre- and Post-Irradiation Glucan Treatment on Pluripotent Stem Cells, Granulocyte, Macrophage and Erythroid Progenitor Cells, and Hemopoietic Stromal Cells," Experientia, 40: 1240-1244 (1984).
Patchen, M.L. et al., "Glucan: Mechanisms Involved in its 'Radioprotective' Effect," Journal of Leukocyte Biology, 42: 95-105 (1987).
Patchen, M.L. et al., "Glucan-Induced Hemopoietic and Immune Stimulation: Therapeutic Effects in Sublethally and Lethally Irradiated Mice," Methods Find Exp. Clin. Pharmacol., 8(3): 151-155 (1986).
Patchen, M.L. et al., "In vitro and in vivo Hematopoietic Activities of Betafectin® PGG-Glucan," Exp. Hematol., 26: 1247-1254 (1998).
Patchen, M.L. et al., "Soluble Polyglycans Enhance Recovery from Cobalt-60-Induced Hemopoietic Injury," Journal of Biological Response Modifiers, 3: 627-633 (1984).
Patchen, M.L. et al., "Stimulated Hemopoiesis and Enhanced Survival Following Glucan Treatment in Sublethally and Lethally Irradiated Mice," J Int. Journal of Immunopharmacology, 7 (6): 923-932 (1985).
Patchen, M.L., "Immunomodulators and Hemopoiesis," Surv. Immunol Res., 2: 237-242 (1983).
Pedroso, M., "Application of Beta-1,3-Glucan to Prevent Shipping Fever in Imported Heifers," Archives of Medical Research, 25(2): 181 (1994).
Petruczenko, A., "Glucan Effect on the Survival of Mice After Radiation Exposure," Acta. Physiol. Pol., 35(3): 231-236 (1984).
Reddy, R.K. et al., "A Mixed Population of Immature and Mature Leucocytes in Umbilical Cord Blood Results in a Reduced Expression and Function of CR3 (CD11b/CD18)," Clin Exp Immunol, 114: 462-467 (1998).
Ross, G.D. et al, "Specificity of Membrane Complement Receptor Type Three (CR3) for β-Glucans," Complement. 4: 61-74 (1987).
Ross, G.D. et al., "Membrane Complement Receptor Type Three (CR3) has Lectin-Like Properties Analogous to Bovine Conglutinin and Functions as a Receptor for Zymosan and Rabbit Erythrocytes as well as a Receptor for iC3b," The Journal of Immunol, 134(5): 3307-3315, 1985.
Ross, G.D. et al., "Newly Identified Function for the Complement (C) System in Regulating Hematopoiesis and Bone Marrow Reconstitution After Radiation Injury," Experimental Hematology, 31(7, Suppl. 1): 235-236 (2003).
Ross, G.D. et al., "nCR3 (CD11b, CD18): A Phagocyte and NK Cell Membrane Receptor with Multiple Ligand Specificities and Functions," Clin Exp Immunol, 92: 181-184 (1993).
Ross, G.D., "Regulation of the Adhesion Versus Cytotoxic Functions of the Mac-1/CR3/$_{\gamma M_{f2}}$-Integrin Glycoprotein," Critical Reviews in Immunology, 20: 197-222 (2000).
Ross, G.D., "Role of the Lectin Domain of Mac-I/CR3 (CD11b/CD18) in Regulating Intercellular Adhesion," Immunologic Research, 25(3): 219-227 (2002).
Ross, Gordon D. et al., "Therapeutic Intervention with Complement and J3-Glucan in Cancer," Immunopharmacology, 42: 61-74 (1999).
Roubey et al, "Staurosporine Inhibits Neutrophil Phatocytosis but not iC3b Binding Mediated by CR3 (CD11b/CD18)," The Journal of Immunol., 146(10): 3557-3562 (1991).
Suzuki et al., "Biological Activities of Polysaccharides," Gann, 1969, vol. 60, No. 3, pp. 273-277—Abstract only provided.
Suzuki, 1. et al, "Inhibition of Experimental Pulmonary Metastais of Lewis Carcinoma by Orally Administered (3-Glucan in Mice," Chem. Pharm. Bull., 39(6): 1606-1608 (1991).
Sveinbjernsson, et al., "Macrophage Cytotoxicity Against Murine Meth A Sarcoma Involves Nitric Oxide-Mediated Apoptosis," Biochem. Biophys. Res. Commun., 223(3): 643-649 (1996).
The Merck Manual, 1992, p. 190.
Thornton, B.P. et al., "Analysis of the Sugar Specificity and Molecular Location of the y-Glucan-Binding Lectin Site of Complement Receptor Type 3 (CD11b/CD18)," J. Immunol., 156: 1235-1246 (1996).
Toi et al., "Randomized Adjuvant Trial to Evaluate the Addition of Tamoxifen and PSK to Chemotherapy in Patients with Primary Breast Cancer," Cancer, 70(10):2475-2483 (1992).
Turnbull, J.L. et al., "The Polysaccharide PGG-Glucan, Enhances Human Myelopoiesis by Direct Action Independent of an Additive to Early-Acting Cytokines," Acta. Haematol., 102: 66-71 (1999).
Vetvicka, V. et al., "Pilot Study: Orally Administered Yeast Beta 1,3-Glucan Prophylactically Protects Against Anthrax Infection and Cancer in Mice," J. A mer. Nutrit. Assoc., 5(2): 1-5 (2002).
Vetvicka, V. et al., "Regulation of CR3 (CD11b/CD18)-dependent Natural Killer (NK) Cell Cytotoxicity by Tumour Target Cell MHC Class I Molecules," Clin Exp Immunol, 115: 229-235 1(1999).
Vetvicka, V. et al., "Soluble (3-Glucan Polysaccharide Binding to the Lectin Site of Neutrophil or Natural Killer Cell Complement Receptor Type 3 (CD11b/CD18) Generates a Primed State of the Receptor Capable of Mediating Cytotoxicity of iC3b-Opsonized Target Cells," J. Clin. Invest., 98(1): 50-61 (1996).
Vetvicka, V. et al., "Targeting of Natural Killer Cells to Mammary Carcinoma via Naturally Occurring Tumor Cell-Bound iC3b and beta-glucan-primed CR3 (CD11b/CD18)," J. Immunol, 159(2): 599-605 (1997).
Wagnerova, J. et al., "The Effect of Two Gluean Carboxymethyl Derivatives with Various Substitution Degrees on Cyclophosphamide Immunosuppression in Mice," Immunopharmacol. and Immunotoxicol., 15(2&3): 227-242 (1993).
Wang, S.C., et al., "Targeting HER2: Recent Developments and Future Directions for Breast Cancer Patients," Semin. Oncai., 28(6): 21-29 (2001).
Wessels, M.R. et al., "Studies of Group B Stretococcal Infection in Mice Deficient in Complement Component C3 or C4 Demonstrate an Essential Role for Complement in Both Innate and Acquired Immunity," Proc. Natl. Acad. Sci. USA, 92: 11490-11494 (1995).
www.breastcancer.org (Accessed online at http://www.breastcancer.org/tips/immune/helping.jsp) Mar. 31, 2009.
www.cancerbackup.org (Accessed online at http://www.cancerbackup.org.uk/QAs/TreatmentsQAs/BiologicaltherapiesQAs/Monocionalantibodies/related_faqs/QAs/521) Mar. 31, 2009.

(56) References Cited

OTHER PUBLICATIONS

Xia, Y. et al., "Generation of Recombinant Fragments of CD11b Expressing the Functional γ-Glucan-Binding Lectin Site ofCR3 (CD11b/CD18)," J Immunology, 162(12):7285-7293 (1999).

Xia, Y. et al., "The β-Glucan-Binding Lectin Site of Mouse CR3 (CD11b/CD18) and Its Function in Generating a Primed State of the Receptor That Mediates Cytotoxic Activation in Response to iC3b-Opsonized Target Cells," J. Immunol., 162: 2281-2290 (1999).

Yadomae, T, "Structure and Biological Activities of Fungal Beta-1,3-glucans," J. Pharm. Soc. of Japan, 120(5): 413-431 (2000).

Yan et al., "Critical Role of Kupffer Cell CR3 (CD11b/CD18) in the Clearance of IgM-Opsonized Erythrocytes or Soluble B-Glucan," Immunopharmacol., 46: 39-54 (2000).

Yan, J. et al., "β-Glucan, a 'Specific' Biologic Response Modifier that uses Antibodies to Target Tumors for Cytotoxic Recognition by Leukocyte Complement Receptor Type 3 (CD11b/DC18)," Journal of Immunology, vol. 163(6): 3045-3052 (Sep. 1999).

Canadian Acknowledgement of Request for Examination, Mailed: Oct. 16, 2008 in Canadian Application No. 2,496,596.

Canadian Request for Examination, Filed: Aug. 28, 2008 in Canadian Application No. 2,496,596.

Chinese Decision on Request for Invalidation regarding Chinese Patent No. 038248965.6, mailed Jul. 8, 2009, 2 pages (English Translation Only).

Chinese First Notification of Office Action (English Translation), Mailed: Mar. 3, 2006 in Chinese Application No. 03824895.6.

Chinese Invention Patent Certificate for Chinese Application No. 03824895.6; Date of Mailing: Jan. 23, 2008 (English Translation Only).

Communication Pursuant to Article 94(3) EPC for European Application No. EP 0378 6508 "Cancer Therapy Using Beta Glucan and Antibodies"; Date Mailed: Mar. 3, 2011.

Communication Pursuant to Article 94(3) EPC for European Application No. EP 03 786508; Date Mailed: Nov. 11, 2009.

Communication Pursuant to Article 96(2) EPC for European Application No. EP 03 749452; Date Mailed: Oct. 10, 2007.

Communication Pursuant to Article 96(2) EPC for European Application No. EP 03 78 5229; Date Mailed: Dec. 5, 2006.

Communication Pursuant to Article 96(2) EPC for European Application No. EP 03 78 6508; Date Mailed: Sep. 7, 2007.

Decision of Final Rejection for Chinese Application No. 03824893. x; Date Mailed: Jul. 24, 2009 (English Translation Only).

Decision on Request for Invalidation for Chinese Application No. 03824895.6; Date Mailed: Jun. 24, 2009 (English Translation Only).

EP Communication Pursuant to Article 96(2) EPC, Mailed: Oct. 10, 2007 in European Application No. 03749452.3.

EP Proceeding Further with the European Patent Application Pursuant to Article 96(1) and Rule 51(1) EPC, Mailed: Jun. 11, 2007 in European Application No. 03749452.3.

EP Reply to EP Proceeding Further with the European Patent Application Pursuant to Article 96(1) and Rule 51(1) EPC, Filed: Aug. 10, 2007 in European Application No. 03749452.3.

EP Response, Filed: Jul. 3, 2008 in European Application No. 03749452.3.

EP Supplementary European Search Report, Mailed: May 23, 2007 in European Application No. 03749452.3.

European Search Report for European Application No. EP 1000 1786; Date Mailed: Mar. 16, 2010.

Final Office Action, Mailed Mar. 13, 2013 in U.S. Appl. No. 12/615,040 "Cancer Therapy Using Whole Glucan Particles and Antibodies".

First Notification of Office Action for Chinese Application No. 2006101362698; Date Mailed: Feb. 22, 2008 (English Translation Only).

First Notification of Office Action for Chinese Application No. 03824895.6; Date of Mailing: Mar. 3, 2006 (English Translation Only).

First Notification of Office Action for Chinese Application No. 03824893.X; Date Mailed: Mar. 24, 2006 (English Translation Only).

Fourth Office Action for Chinese Application No. 03824893.X; Date Mailed: Nov. 7, 2008 (English Translation Only).

International Preliminary Examination Report for Int'l Application No. PCT/US03/27841; Date Mailed: Dec. 6, 2004.

International Preliminary Examination Report for Int'l Application No. PCT/US2003/025237; Date Mailed: Jun. 24, 2005.

International Preliminary Examination Report for Int'l Application No. PCT/US2005/016229; Date Mailed: Nov. 14, 2006.

International Preliminary Examination Report for Int'l Application No. PCT/US03/27975; Date Mailed: Dec. 15, 2004.

International Search Report for Int'l Application No. PCT/US03/27975; Date Mailed: May 24, 2004.

International Search Report for Int'l Application No. PCT/US03127841 ; Date Mailed: Jun. 21, 2004.

International Search Report for Int'l Application No. PCT/US2005/016229; Date Mailed: Jul. 27, 2006.

International Search Report for Int'l Application No. PCTIUS2003/025237; Date Mailed: Jul. 9, 2004.

Japanese Request for Examination and Amendment, Filed: Aug. 31, 2006 in Japanese Application No. 2004-534637, 6 pages (with English translation).

Non-Final Office Action, Mailed Jun. 20, 2012 in U.S. Appl. No. 12/615,040 "Cancer Therapy Using Whole Glucan Particles and Antibodies".

Notice of Allowance, Mailed Jun. 20, 2013 in U.S. Appl. No. 12/217,701 "Methods of Using Beta Glucan As a Radioprotective Agent".

Notice of Opposition of European Patent No. 1536820 Cancer Therapy Using Whole Glucan Particles and Antibodies dated Feb. 8, 2011.

Notification of Acceptance of Request for Invalidation for Chinese Application No. 03824895.6; Date of Mailing: Jan. 25, 2009 (English Translation Only).

Notification of First Office Action for Chinese Application No. 200580018895.0; Date Mailed: Jan. 23, 2009 (With English Translation).

Notification of Oral Proceedings for Chinese Application No. 03824895.6; Date of Mailing: Mar. 9, 2009 (English Translation included).

Notification of Second Office Action for Chinese Application No. 200580018895.0; Date Mailed: Apr. 30, 2010 (With English Translation).

Office Action for Canadian Application No. 2,496,508 "Cancer Therapy Using Beta Glucan and Antibodies"; Date Mailed Nov. 29, 2010.

Office Action for Canadian Application No. 2,496,596 "Cancer Therapy Using Whole Glucan Particles and Antibodies"; Date Mailed: Dec. 2, 2010.

Office Action for Japanese Application No. JP 2004-528076; Date Mailed: Feb. 18, 2010, 6 pages (with English translation).

Office Action for Japanese Application No. JP 2004-534637; Date Mailed: Jan. 27, 2010, 7 pages (with English translation).

Oral Hearing Arguments in Written Form to the Board of Patent for Chinese Application No. 03824895.6; Date Mailed: May 7, 2009, 18 pages (with English translation).

PCT Notification of Transmittal of International Preliminary Examination Report, Mailed: Dec. 15, 2004 in International Application No. PCT/US03127841.

PCT Reply to First Written Opinion, Filed: Nov. 3, 2004 in International Application No. PCT/US03/27841.

PCT Written Opinion, Mailed: Sep. 3, 2004 in International Application No. PCT/US03127841.

Request for Re-examination for Chinese Application No. 03824893. X; Date Mailed: Nov. 9, 2009 (With English Translation).

Response to Communication Pursuant to Article 96(2) EPC for European Application No. 03749452.3 "Cancer Therapy Using Whole Glucan Particles and Antibodies"; Date Mailed: Jul. 3, 2008.

Response to First Office Action for Chinese Application No. 03824895.6; Date of Mailing: Jul. 18, 2006, 12 pages (with English translation).

Response to Notice of Opposition of European Patent No. 1536820 "Cancer Therapy Using Whole Glucan Particles and Antibodies" dated Aug. 2011.

(56) References Cited

OTHER PUBLICATIONS

Response to Second Office Action for Chinese Application No. 2006101362698; Date Mailed: Mar. 30, 2009, 8 pages. (with English translation).
Response to the First Office Action for Chinese Application No. 2006101362698; Date Mailed: Sep. 8, 2008, 10 pages (with English translation).
Response to the First Office Action for Chinese Application No. 03824893.x; Date Mailed: Oct. 8, 2006 (English Translation of Amended Claims Only).
Response to the First Office Action for Chinese Application No. 200580018895.0; Date Mailed: Aug. 7, 2009 (With English Translation of Claims).
Response to the Fourth Office Action for Chinese Application No. 03824893.x; Date Mailed: Mar. 23, 2009, 12 pages. (with English translation).
Response to the Notification of Acceptance of Request for Invalidation for Chinese Application No. 03824895.6; Date of Mailing: Mar. 6, 2009, 20 pages (with English translation).
Response to the Second Office Action for Chinese Application No. 03824893.x; Date Mailed: Jun. 21, 2007, 12 pages (with English translation).
Response to the Third Office Action for Chinese Application No. 03824893.X; Date Mailed: Dec. 24, 2007, 12 pages (with English translation).
Second Notification of Office Action for Chinese Application No. 2006101362698; Date Mailed: Nov. 14, 2008 (English Translation Only).
Second Notification of Office Action for Chinese Application No. 03824893.x; Date Mailed: Feb. 9, 2007 (English Translation Only).
Summary of Oral Proceedings for Chinese Application No. 03824895.6; Dated: Apr. 15, 2009 (English Translation Only).
Summons to Oral Proceedings for European Application 03786508.6 "Cancer Therapy Using Beta Glucan and Antibodies"; Dated: Sep. 26, 2012.
Supplementary European Search Report for European Application No. EP 03 749452; Date Mailed: Apr. 16, 2007.
Supplementary European Search Report for European Application No. EP 0378 5229; Date Mailed: Feb. 9, 2006.
Supplementary European Search Report for European Application No. EP 03 78 6508; Date Mailed: May 11, 2007.
Third Notification of Office Action for Chinese Application No. 2006101362698; Date Mailed: Jan. 8, 2010 (English Translation Only).
Third Office Action for Chinese Application No. 03824893.X; Date Mailed: Aug. 10, 2007 (English Translation Only).
U.S. Office Action—Final, Mailed Dec. 9, 2010 in U.S. Appl. No. 12/217,701 "Methods of Using Beta Glucan as a Radioprotective Agent".
U.S. Office Action—Final, Mailed: Aug. 7, 2008 in U.S. Appl. No. 10/526,175.
U.S. Office Action—Final, Mailed: Jan. 17, 2012 in U.S. Appl. No. 11/579,467 Whole Glucan Particles in Combination With Antibiotics, Vaccines and Viral Monoclonal Antibodies.
U.S. Office Action—Non-Final, Mailed Jun. 24, 2010 in U.S. Appl. No. 12/217,701 "Methods of Using Beta Glucan as a Radioprotective Agent".
U.S. Office Action—Non-Final, Mailed May 18, 2011 in U.S. Appl. No. 11/579,467 "Whole Glucan Particles in Combination With Antibiotics, Vaccines and Viral Monoclonal Antibodies".
U.S. Office Action—Non-Final, Mailed: Nov. 29, 2007 in U.S. Appl. No. 10/526,175.
U.S. Office Action—Restriction Requirement, Mailed: Aug. 22, 2007 in U.S. Appl. No. 10/526,175.
U.S. Office Action—Non-Final, Mailed: Nov. 29, 2007 in U.S. Appl. No. 10/526,175 "Cancer Therapy Using Whole Glucan Particles and Antibodies".
U.S. Reply to Office Action, Filed: May 29, 2008 in U.S. Appl. No. 10/526,175.
U.S. Reply to Restriction Requirement, Filed: Sep. 24, 2007 in U.S. Appl. No. 10/526,175.
Written Opinion for Int'l Application No. PCT/US2005/016229; Date Mailed: Jul. 27, 2006.

\* cited by examiner

FIG. 26A
FIG. 26B
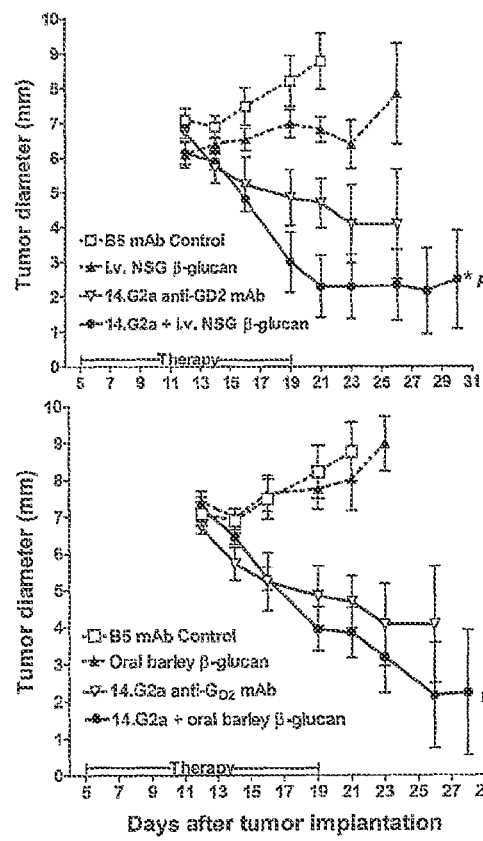
FIG. 26C
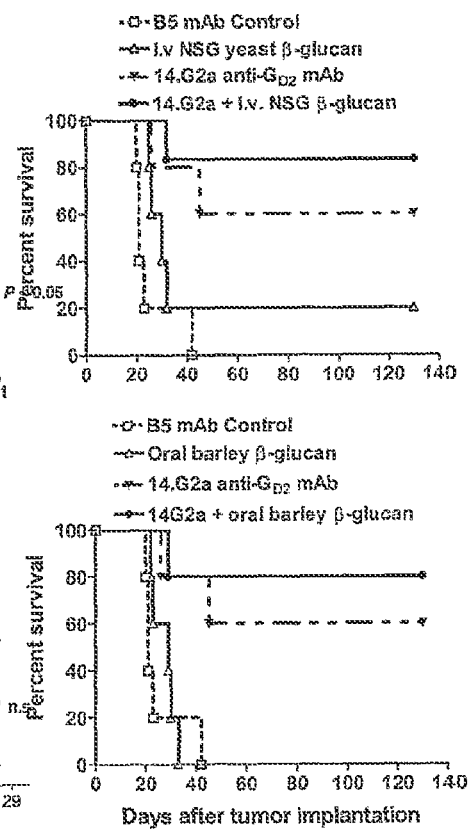
FIG. 26D

CANCER THERAPY USING BETA GLUCAN AND ANTIBODIES

RELATED APPLICATIONS

This application is a continuation of U.S. Ser. No. 10/526,185, filed Aug. 3, 2005, which is a National Stage application under 35 U.S.C. 371 of International Application No. PCT/US2003/027975, filed Sep. 4, 2003, which application claims the benefit of U.S. Provisional Application No. 60/408,126, filed Sep. 4, 2002. The entire teachings of the above applications are incorporated herein by reference.

GOVERNMENT SUPPORT

The invention was supported, in whole or in part, by grant RO1CA86412 from National Institute for Health/National Cancer Institute and grant BC010287 from the Department of Defense, U.S. Army. The Government has certain rights in the invention.

BACKGROUND OF THE INVENTION

Beta(β)-glucan is a complex carbohydrate, generally derived from several sources, including yeast, bacteria, fungi and cereal grains. Each type of β-glucan has a unique structure in which glucose is linked together in different ways, resulting in different physical and chemical properties. For example, β(1-3) glucan derived from bacterial and algae is linear, making it useful as a food thickener. The frequency of side chains, known as the degree of substitution or branching frequency, regulated secondary structure and solubility. Beta glucan derived from yeast is branched with β(1-3) and β(1-6) linkages, enhancing its ability to bind to and stimulate macrophages. β(1-3;1-6) glucan purified from baker's yeast (Saccharomyces cerevisiae) is a potent anti-infective beta-glucan immunomodulator.

The cell wall of S. cerevisiae is mainly composed of β-glucans, which are responsible for its shape and mechanical strength. While best known for its use as a food grade organism, yeast is also used as a source of zymosan, a crude insoluble extract used to stimulate a non-specific immune response. Yeast-derived beta (1,3;1,6) glucans stimulate the immune system, in part, by activating the innate anti-fungal immune mechanisms to fight a variety of targets. Baker's yeast β(1-3;1-6) glucan is a polysaccharide composed entirely of β(1-3)-linked sugar (glucose) molecules forming the polysaccharide backbone with periodic β(1-3) branches linked via β(1-6) linkages). It is more formally known as poly-(1-6)-β-D-glucopyranosyl-(1-3)-β-D-glucopyranose. Glucans are structurally and functionally different depending on the source and isolation methods.

Beta glucans possess a diverse range of activities. The ability of β-glucan to increase nonspecific immunity and resistance to infection is similar to that of endotoxin. Early studies on the effects of β(1,3) glucan on the immune system focused on mice. Subsequent studies demonstrated that β(1,3) glucan has strong immuno stimulating activity in a wide variety of other species, including earthworms, shrimp, fish, chicken, rats, rabbits, guinea pigs, sheep, pigs cattle and humans. Based on these studies, β(1,3) glucan represents a type of immunostimulant that is active across the evolutionary spectrum, likely representing an evolutionarily innate immune response directed against fungal pathogens. However, despite extensive investigation, no consensus has been achieved on the source, size, and form of β(1-3) glucan ideal for use as an immunostimulant.

The potential antitumor activity of β-glucans has been under investigation for about 30 years, as disclosed primarily in the Japanese pharmaceutical literature. Lentinan, for example, has been extensively investigated both in animal models at 1 mg/kg for 10 days and in clinical trials since the late 1970s for advanced or recurrent malignant lymphoma and colorectal, mammary, lung and gastric cancers. A recent review describes much of this work, which has focused on β-glucans isolated from mushrooms (Borchers, A T., et al., *Mushrooms and Immunity,* 221(4), 281 (1999)). This work indicates that the antitumor activity of polysaccharides isolated from mushrooms is largely mediated by T cells and macrophages, which are activated by β-glucan. Oral β-glucan isolated from crude yeast and cereal grain preparations has demonstrated antitumor activity as well. These studies used crude β(1,3) glucan preparations that are mixtures of β(1,3) glucan along with other polysaccharides such as β-glucans, mannans, chitin/chitosan, β(1,4) glucans, nucleic acids, proteins, and lipids. The β(1,3) glucan content of these preparations is typically less than 50% by weight. The effectiveness of various glucans differs in their ability to elicit various cellular responses, particularly cytokine expression and production, and in their activity against specific tumors. It has been proposed that the antitumor mechanism of action of β-glucans involves macrophage simulation and subsequent release of inflammatory mediators such as IL-1, TNF, and prostaglandin E2 (Sveinbjørnsson et al., *Biochem. Biophys. Res. Commun.* 223(3), 643 (1996)).

The immune system comprises two overall systems; the adaptive immune system and the innate immune system. β-glucans are considered to operate primarily through the relatively non-specific, innate immune system. The innate immune system includes complement proteins, macrophages, neutrophils, and natural killer (NK) cells, and serves as a rapid means of dealing with infection before the adaptive immune system can be brought to bear. Particulate β-glucan and high molecular weight soluble β-glucans such as lentinan and schizophyllan have been shown to be large enough to cross-link membrane CR3 of neutrophils and macrophages, triggering respiratory burst, degranulation, and cytokine release in the absence of target cells. (G. D. Ross, et al., *Immunopharmacology* 42, 61 (1999)). Neutral soluble β-glucan, on the other hand, does not simulate cytokine release, most likely because it is too small to cross-link membrane CR3.

The subtle changes associated with cancer development can lead to different expression of surface proteins, which can stimulate a weak response by the adaptive immune system. These changes in surface antigen expression also provide a target for treatment using selective monoclonal antibodies (mAbs) or antitumor vaccines. Monoclonal antibodies have been developed to target various proteins expressed in colon cancer, lymphoma, breast cancer, and acute leukemia, for example. The immune basis of the clinical tumor response to mAb includes direct cytotoxicity and induced immunity, in which antibody-dependent cell-mediated cytotoxicity and complement-mediated cytotoxicity are responsible for the direct killing of tumor cells. However, it has been noted that the increased complement activation mediated by natural or monoclonal antibodies often shows little effect on tumor growth due to the inherent resistance of tumors to complement-mediated cytotoxicity. This inherent resistance results in mAbs or vaccines to tumor antigens ineffective therapeutically. Monoclonal antibody (mAb) therapy is limited by effector mechanisms (e.g., antagonism of growth factor receptors, antibody-dependent cell-mediated cytotoxicity).

Tumor immunotherapy with humanized monoclonal antibodies (mAbs) such as Herceptin™ (trastuzumab) and Rituxan™ (rituximab) is now accepted clinical practice in patients with Her-2/neu+ metastatic mammary carcinoma and B cell lymphoma, respectively (Wang, S. C., et. al., Semin. Oncol., 28: 21-29, 2001; Leyland-Jones, B., Lancet Oncol., 3: 137-144, 2002; Ranson, M. and M. X Sliwkowski, Oncology, 63 Suppl 1: 17-24 (2002), Johnson, P. and M. Glennie, Semin. Oncol., 30: 3-8 (2003), Plosker, G. L. and D. P. Figgitt, Drugs, 63: 803-843 (2003) and Ross, J. S., et al., Am. J. Clin. Pathol., 119: 472-485 (2003)). Based on their record of success, several other humanized mAbs are being developed and some, such as Erbitux™ (cetuximab) are apparently close to achieving final FDA approval. Nevertheless, antibody therapy is not uniformly effective, even in patients whose tumors express a high surface density of the target tumor antigen. Effector mechanisms thought to cause tumor regression are variable and particularly include inhibition of growth factor activity, as well as antibody-dependent cell-mediated cytotoxicity (ADCC). Complement-dependent cytotoxicity (CDC) has less frequently been identified as an effector mechanism and it remains somewhat controversial whether CDC contributes significantly to tumor regression. In vitro studies have shown that CDC is limited by membrane regulators of the complement system, such as CD55 and CD59, that are occasionally overexpressed on tumors. Moreover, the major complement-mediated effector mechanism used against microbial pathogens, C3-receptor-dependent phagocytosis and cytotoxic degranulation, is completely inactive against cancer. With the antitumor human IgG1-based mAbs that activate complement such as trastuzumab, rituximab, or cetuximab, a coating of iC3b is deposited on tumor cells that can be recognized by the leukocyte iC3b-receptor CR3 (Mac-1; CD11b/CD18; $\alpha_M\beta_2$-integrin). However, the triggering of CR3-dependent leukocyte (neutrophil, monocyte, macrophage, NK cell) mediated cytotoxicity requires that CR3 bind to both iC3b and binding to the lectin site. Since tumor cells do not express CR3-activating polysaccharides, they escape this protective mechanism effective against microbial pathogens.

An increasing awareness exists determining that effective destruction of tumors by the immune system requires a combination of effector mechanisms. Thus, a single vaccine, cytokine, or biological response modifier is unlikely to be successful in a majority of patients. For example, vaccines may elicit immune cytotoxic T lymphocytes and/or humoral antibody responses, but each has shortcomings. Antibodies are frequently ineffective because normal host cell proteins such as DAF, MCP, and CD59 inhibit complement-mediated cytotoxicity. Further, iC3b-opsonization of tumors does not, solely, recruit phagocytes or NK cells. Antibody-dependent cell-mediated immunity is thought to fail because the IgG density achieved on tumors is too low and antibody Fc fragment-mediated cytotoxicity is suppressed by NK cell recognition of tumor cell MHC class I. Cell-mediated immunity utilizing cytotoxic T lymphocytes has disadvantages as well, since tumors, as part of the metastatic process, often lose the major histocompatability complex molecules required for antigen presentation. Therefore, a need exists for antitumor therapy that avoids the shortcomings discussed above.

SUMMARY OF THE INVENTION

The present invention relates to methods of using neutral soluble β(1,3) glucan (NSG) with a vaccine or monoclonal antibodies for antitumor therapy. Methods of using β-glucans as an adjuvant for mAb therapy of cancer to provide a leukocyte CR3-dependent mechanism of tumor killing that is additive to all other effector mechanisms is also described. In particular, the antitumor activity of a composition containing soluble beta-glucan and complement activating tumor specific antibodies are described. In certain embodiments, the antibodies are IgG subclass I or IgG subclass III. The soluble glucans described activate the immune system without the detrimental activation of inflammatory cytokines. Additionally, methods are directed to the single stranded conformation of neutral soluble glucan for activation of the innate immune system without induction of inflammatory cytokines. The antibodies are can also be induced in a patient by administering an appropriate vaccine or can be provided directly by administering monoclonal or polyclonal antibodies, such as by intraveneous administration of a monoclonal antibody.

Also described is the use of insoluble beta (1,3) glucan (whole glucan particles) as an immunomodulator by inducing a shift from a Th2 response to the Th1 response, stimulating an enhanced antitumor cytotoxic T-cell response.

A key part of the mechanism of antibody-mediated tumor cell killing involves recognition of the antibody-tumor antigen complex by C3 complement protein, forming the C3-antibody-tumor antigen complex. This complex is subsequently recognized by innate immune cells via CR3. Innate immune cells bear CR3 receptor and recognize the tumor cells as foreign through the specific interaction between CR3 and C3-antibody-tumor cell antigen complex. When CR3 binds to this complex, innate immune cells are stimulated to exert their tumoricidal activities. In the present invention, these innate immune cells also stimulated by compositions comprising neutral soluble glucan. Monocytes, macrophages, neutrophils and NK cells become activated upon NSG binding to CR3 on their cell surface. The activation of these cells by NSG-CR3 interactions enhances the C3-antibody-tumor cell antigen complex-targeted tumoricidal activities of these cells, resulting in enhanced tumor cell killing. In certain embodiments, the action is synergistic.

A novel aspect of this invention is the anti-tumor activity of NSG from any β(1,3)-glucan source with complement activating antibodies. Beta glucan in the form of NSG has the advantage of being readily prepared in high purity from any source of β glucan. The use of neutral soluble glucan as an antitumor agent has a number of important aspects. First, the use of highly pure neutral soluble glucan leads to higher activity with fewer side effects. Second, the glucan can bind to the lectin binding domain of CR3, thereby activating the tumoricidal activities of innate immune cells. By utilizing the targeted activation creating by complement depostion, β glucan leads to enhanced tumor clearance by the immune system, both through direct cytotoxic effects and by localized cytokine-mediated recruitment of immune cells. Finally, the single stranded conformation of neutral soluble glucan allows for activation of the innate immune system without induction of inflammatory cytokines.

Methods of suppressing or eliminating tumor cells, comprising administering to a subject in need of treatment a therapeutically effective amount of neutral soluble glucan and at least one complement activating anti-tumor antibody, wherein the glucan does not induce inflammatory cytokines and the glucan and antibody suppresses or eliminates tumor cells are described.

The antibody can be introduced via direct administration of monoclonal or polyclonal antibodies or produced by the body via cancer vaccine. In certain embodiments, the antibody is selected from the group consisting of: trastuzumab, rituximab, cetuximab and combinations thereof. In other embodiments, the soluble beta glucan is administered parenterally In certain embodiments, the neutral soluble glucan is in a single helix conformation, a triple helix conformation or combinations thereof.

Also described are methods of treating a neoplastic cell, comprising administering to the cell a therapeutically effective dose of a neutral soluble glucan and a complement activating antibody specific to the neoplastic cell; wherein the glucan does not induce inflammatory cytokines. In certain embodiments, the glucan and antibody retard the rate of growth of the neoplastic cell and/or inhibit the growth of the neoplastic cell and/or extend the survival time of a host of the neoplastic cell.

Also described are methods of immunomodulation in which a shift from a Th2 response to a Th1 response is induced by administering a therapeutically effective amount of whole glucan particles. The immunomodulation for the treatment of cancer in which a shift from a Th2 response to a Th1 response is induced by administering a therapeutically effective amount of whole glucan particles. In certain embodiments, the immunomodulation increases the effectiveness of anti-tumor therapy.

Also described is the use of a composition comprising neutral soluble glucan and complement activating antibody for the manufacture of a medicament for use in treating a neoplastic cell, wherein the composition retards the growth of the cell and the glucan does not induce inflammatory cytokines.

In other embodiments, methods of suppressing or eliminating tumor cells, comprising administering to a subject in need of treatment a therapeutically effective amount of a composition comprising, neutral soluble barley glucan and at least one complement activating anti-tumor antibody, wherein the composition suppresses or eliminates tumor cells.

BRIEF DESCRIPTION OF THE DRAWINGS

The foregoing and other objects, features and advantages of the invention will be apparent from the following more particular description of preferred embodiments of the invention, as illustrated in the accompanying drawings.

FIG. 5A is a graph of anti mouse-IgG-PE vers Mlg-FITC. FIG. 5B is a graph of anti-MUC1-PE verses anti-IgM-FITC. FIG. 5C is a graph of anti-MUC1-PE verses anti-IgG-FITC. FIG. 5D is a graph of anti-MUC1 verses anti-C3-FITC.

FIG. 14A is a graph showing blood from normal mice with no tumor. FIG. 14B is a graph showing T cells are making Il-4. FIG. 14C is a graph showing blood from two mice 12 days after implantation of tumors. FIG. 14D is a graph showing T cells have stopped making Il-4. FIG. 14E is a graph showing blood from two mice after impanation and 2 days after starting WGP therapy.

FIG. 17A is a graph showing Pta64 therapy with 11Cl anti-MMTV mAb combined with glucan. FIG. 17B is a graph showing RMA-S-MUC1 therapy with i.v. 14 G2a anti-GD2 mab combined with glucan. FIG. 17C is a graph showing RMA-S-MUC1 therapy with i.v. BCP8 anti-MUC1 mab combined with glucan. After tumor cells were implanted, small tumors were allowed to form over 5-9 days before immunotherapy was carried out for a total period of 14 days. Tumor measurements were taken over a 3-week period and then survival was monitored (survival data shown in FIG. 18A-18C). Panel A shows therapy of Ptas64 mammary carcinoma in BALB/c mice using a combination of 11C1 IgG2a anti-MMTV with or without simultaneous administration of NSG β-glucan. Some tumor regression occurred with either 11C1 mAb or NSG β-glucan (300 μg per day) alone, but the combined use of NSG β-glucan plus 11C1 mAb produced significantly more tumor regression than did treatment with 11C1 mAb alone (P<0.05). In graphs B and C, C57B1/6 mice were implanted s.c. with RMA-S-MUC1 tumor cells and then 5 days later treated with either 14.G2a anti-$G_{D2}$ ganglioside and/or NSG β-glucan (300 μg per day) or BCP8 IgG2b anti-MLTC1 and/or NSG β-glucan (300 pig per day). With either mAb, the combined administration of NSG β-glucan resulted in significantly more tumor regression than with mAb therapy alone. Mean values and standard errors (SE) of the mean are shown.

FIG. 18A is a graph showing Pta64 therapy with 11CI anti-MMTV mAb combined with glucan. FIG. 18B is a graph showing RMA-S-MUC1 therapy with i.v. 14 G2a anti-GD2 mab combined with glucan FIG. 18C is a graph showing RMA-S-MUC1 therapy with i.v. BCP8 anti-MUC1 mab combined with glucan. These data represent the survival curves for the tumor therapy protocols described in the legend for FIG. 17A-17C.

FIG. 19A is a graph showing the tumor diameter vs. therapy of wild type mice. FIG. 19B is a graph showing the tumor diameter vs. therapy of CR3 deficient mice. Comparable groups of CR3-deficient C57Bl/6 mice and their wild-type littermates were implanted s.c. with RMA-S-MUC1 tumor cells (2×10$^6$) and tumors of 5-6 mm diameter were allowed to form over 10 days before carrying out immunotherapy for a total period of 21 days. Tumor measurements were made at the indicated times (FIGS. 19A-19B) and then survival was monitored (FIGS. 20A-20B). Mice received 14.G2a anti-$G_{D2}$ ganglioside mAb (100 μg every 3rd day) and/or NSG β-glucan (400 μg daily). There was no difference in the rate of tumor regression produced by mAb therapy alone in the CR3-deficient versus wild-type mice and there was no β-glucan enhancement of mAb-mediated tumor regression in the CR3-deficient mice. Even though the enhancement of mAb-mediated regression induced by β-glucan was not significant (n.s.), β-glucan did significantly enhance mAb-mediated survival (FIG. 20A). Mean values±SE of the mean are shown.

FIG. 21A shows the tumor diameter vs. therapy of wild type mice. FIG. 21B shows the tumor diameter vs. therapy of CR3 deficient mice. C3-deficient (C3$^{-/-}$) mice and their wild-type littermates on a C57BL/6 background were implanted s.c. with 1×10$^6$ Lewis Lung carcinoma tumor cells transfected with human MUC1 (LL/2-MUC1). After allowing 7 days for development of small tumors, mice were treated with BCP8 IgG2b anti-MUC1 mAb (200 μg every 3rd day) and/or NSG β-glucan (400 μg daily) for a total therapy period of 3 weeks. Therapy with BCP8 mAb alone did not produce significant tumor regression in either wild-type or C3-deficient mice, whereas the combination of BCP8 mAb and soluble β-glucan produced significant tumor regression in wild-type but not in C3-deficient mice. Mean values±SE of the mean are shown.

FIG. 22A shows the tumor diameter vs. therapy of wild type mice. FIG. 22B shows the tumor diameter vs. therapy of CR3 deficient mice. These data represent the survival curves for the tumor therapy protocol described in FIGS. 21a-21b.

FIGS. 26A-26D are a series of graphs showing orally administered barley β-glucan elicits tumor regression (FIG. 26C) and survival (FIG. 26D) that is similar to tumor regression (FIG. 26A) and survival (FIG. 26B) shown with i.v. yeast β-glucan.

DETAILED DESCRIPTION OF THE INVENTION

Figure 1:
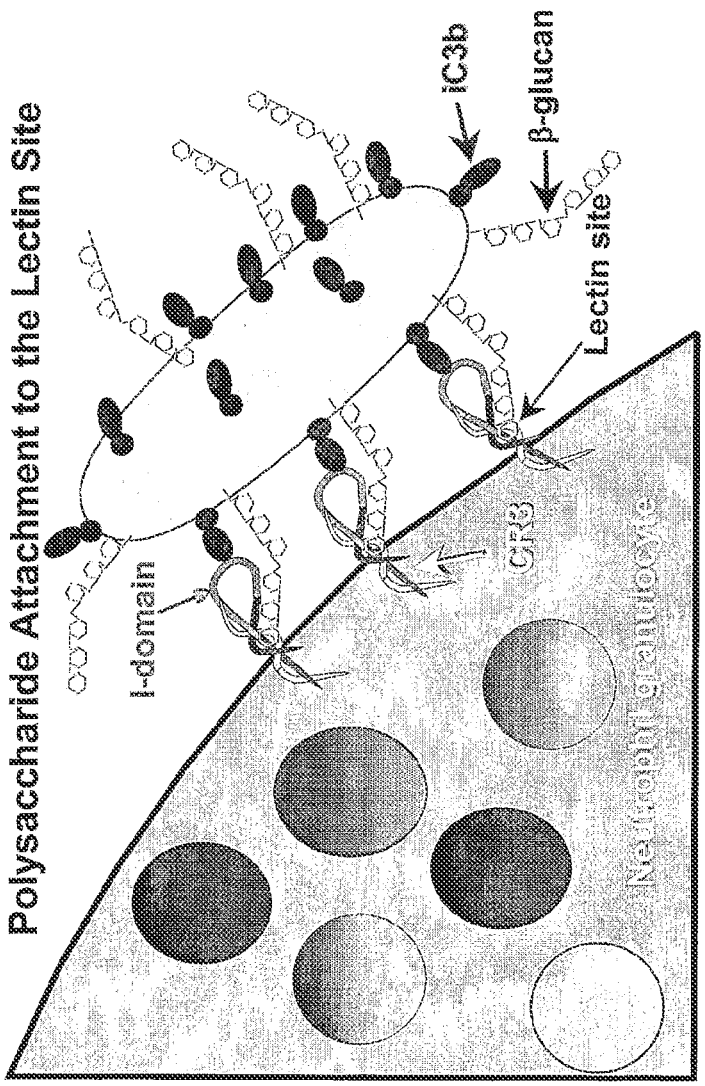
FIG. 1 is a drawing showing that activation of CR3 by C3-opsonized yeast requires both iC3b ligation and β-glucan attachment to the lectin site.

A description of preferred embodiments of the invention follows.

The present application discloses methods of antitumor therapy in which NSG is used with complement activating antibodies directed to tumor antigens to provide an antitumor effect. As used herein the neutral soluble glucan is a neutral soluble glucan composition comprised primarily of 1,3 glucose from any glucan source. In certain embodiments, the NSG is comprised of beta 1,3;1,6 glucan from yeast sources. In other embodiments, the NSG is produced from cereal grains and comprises 1,3; 1,4 linkages.

In a certain embodiment, the method harnesses the activity of both the innate and adaptive immune system and provides a synergistic effect. This synergism derives, in part, from the ability of the antibody to selectively target tumor cells while NSG amplifies the normally weak humoral response by using the C3 deposition induced by the antibodies to target tumor cells for recognition by innate immune cells bearing β-glucan primed CR3. Additional synergism is obtained by administering β-glucans that specifically stimulate either the innate or adaptive immune system in order to fully engage both systems.

The present application discloses that the anti-cancer immune activities stimulated by tumor antigen-directed monoclonal antibody therapy and anti-tumor vaccines are augmented by highly purified soluble glucan. Cell surface monoclonal antibodies and tumor vaccines stimulate a complex anti-tumor immune response involving non-specific and specific immune responses. The non-specific immune responses involve innate immune cell factors (e.g. the complement system) and cells (dendritic, monocyte, macrophage, neutrophil and NK cells). Tumor antigen-directed monoclonal antibodies and antibodies stimulated by tumor vaccines bind to the surface of tumor cells target these cells for direct complement action and complement-mediated cytotoxicity.

A key part of the mechanism of antibody-mediated tumor cell killing involves recognition of the antibody-tumor antigen complex by C3 complement protein, forming the C3-antibody-tumor antigen complex. This complex is subsequently recognized by innate immune cells via CR3. Innate immune cells bear CR3 receptor and recognize the tumor cells as foreign through the specific interaction between CR3 and C3-antibody-tumor cell antigen complex. When CR3 binds to this complex, innate immune cells are stimulated to exert their tumoricidal activities. In the present invention, these innate immune cells are also stimulated by neutral soluble glucan therapies. Monocytes, macrophages, neutrophils and NK cells become activated upon soluble β(1,3; 1,6)-glucan binding to CR3 on their cell surface. The activation of these cells by soluble β(1,3; 1,6)glucan-CR3 interactions enhances the C3-antibody-tumor cell antigen complex-targeted tumoricidal activities of these cells, resulting in synergistically enhanced tumor cell killing.

In addition to the NSG-CR3-mediated enhancement of the tumoricidal activities of the innate immune system, β glucan therapy using a particulate glucan (WPG) induces a Th2 to Th1 shift in the acquired immune system response. Typically an acquired immune response against a tumor is unable to undergo a shift from a Th2 (humoral/antibody response) to a Th1 response (cell-mediated killer T-cell response). As a result, the full strength of the acquired immune system is not available to fight against the cancer. However, WGP induces a rapid Th2 to Th1 shift in circulating monocyte/macrophages and T-cells, demonstrated by the effect of WPG on the cytokine profiles of these key immune cells. This shift to the cytotoxic T-cell response against the tumor leads to an enhanced anti-tumor response by the acquired immune system, as tumor cells are refractory to complement-mediated cytotoxicity but susceptible to the cytotoxic killer T-cell response.

Another aspect of the present invention is the action of oral WGP to induce an acquired immune cytotoxic T-cell anti-tumor immune response while systemic NSG leads to an enhancement of the anti-tumor activity of cell surface monoclonal antibodies and/or tumor vaccine therapy via the innate immune cell response. While not intending to be bound by theory, WGP and NSG, due to their different structures, act on different cell populations. WGP acts on gut-associated lymphoid tissue (GALT) and lymphoid cells, while NSG acts on circulating innate immune cells. The enhancement of the innate and acquired immune responses are synergistic and lead to significantly increased anti-tumor activity.

The present application also discloses a method of immunomodulation in which a shift from a Th2 response to a Th1 response is induced by administering a therapeutically effective amount of whole glucan particles. While this immunomodulation may have application outside of antitumor therapy, capacity of the immunomodulation to increase the effectiveness of antitumor therapy is of particular interest. The method of immunomodulation involves administering to a subject in need of treatment a therapeutically effective amount of whole glucan particles; and providing antibodies targeted to antigens of said tumor cells; where the antibodies are induced in a subject or individual by administering an appropriate vaccine to the subject or monoclonal or polyclonal antibodies can be directly administered to the individual. Again, the whole glucan particle used may be administered orally, parenterally, or by other methods known in the art. The glucan and complement activating antibody can be administered sequentially, co-administered, or administered at different times.

The adaptive immune system is so called because it adapts to infection by providing a tailored response to antigens present on the surface of foreign material. One of the difficulties cancer poses for the immune system is that cancer cells are not truly foreign, but are instead native cells in which various genes have been inappropriately activated or inactivated. Thus, it is generally believed that the adaptive immune system is ill-suited to dealing with cancer, which is instead generally dealt with by macrophages, neutrophils, and NK cells from the innate immune system. The adaptive immune system contains a further division into the Th1 and Th2 systems, named after the two classes of T helper (Th) cells involved. While simpler in the mouse, where this division was initially discovered, the Th1/Th2 distinction is also present in humans. Th1 helper cells produce cytokines that stimulate strong cellular immunity, but only weak and transient antibody responses. Th2 helper cells, on the other hand, make an array of cytokines that evoke a strong antibody response but only weak cellular activity. Although Th1 and Th2 represent two different types of immune response, the response of an individual to pathogens usually involves both, with one or the other predominating. Interestingly, Th1 and Th2 responses are antagonistic to one another; i.e., a strong Th1 response will tend to suppress the Th2 response, and vice versa.

Yeast-derived NSG glucans work, in part, by stimulating innate anti-fungal immune mechanisms to fight a range of pathogenic challenges from bacteria, fungi, parasites, viruses, and cancer. The molecular mechanism of action of NSG appears to involve specific β-glucan receptor binding sites on the cell membranes of immune cells such as neutrophils and macrophages. Recent data suggests that CR3, the receptor for C3 complement protein, serves as a major receptor for β-glucans. Mannans, galactans, α(1-4)-linked glucose polymers and β(1-4)-linked glucose polymers have no avidity for this receptor. First, the iC3b-receptor CR3 (also known as Mac-1, CD11b/CD18, or $\alpha_M\beta_2$-integrin) was shown to have a β-glucan-binding lectin site that functioned in the phagocytosis of yeast cell walls by neutrophils, monocytes, and macrophages (Ross, G. D., et al., *Complement Inflamm.* 4:61-74 (1987) and Xia, Y. V. et al., *J. Immunol.* 162:2281-2290 (1999)). Mac-1/CR3 functions as both an adhesion molecule mediating the diapedesis of leukocytes across the endothelium and a receptor for the iC3b fragment of complement responsible for phagocytic/degranulation responses to microorganisms. Mac-1/CR3 has many functional characteristics shared with other integrins, including bidirectional signaling via conformational changes that originate in either the cytoplasmic domain or extracellular region. Another key to its functions is its ability to form membrane complexes with glycosylphosphatidylinositol (GPI)-anchored receptors such as Fc gammaRIIIB (CD16b) or uPAR (CD87), providing a transmembrane signaling mechanism for these outer membrane bound receptors that allows them to mediate cytoskeleton-dependent adhesion or phagocytosis and degranulation. Many functions appear to depend upon a membrane-proximal lectin site responsible for recognition of either microbial surface polysaccharides or GPI-linked signaling partners. Because of the importance of Mac-1/CR3 in promoting neutrophil inflammatory responses, therapeutic strategies to antagonize its functions have shown promise in treating both autoimmune diseases and ischemia/reperfusion injury. Conversely, soluble beta-glucan polysaccharides that bind to its lectin site prime the Mac-1/CR3 of circulating phagocytes and natural killer (NK) cells, permitting cytotoxic degranulation in response to iC3b-opsonized tumor cells that otherwise escape from this mechanism of cell-mediated cytotoxicity. CR3 binds soluble fungal β-glucan with high affinity ($5 \times 10^{-8}$M) and this primes the receptor of phagocytes or NK cells for cytotoxic degranulation in response to iC3b-coated tumor cells. The tumoricidal response promoted by soluble β-glucan in mice was shown to be absent in mice deficient in either serum C3 (complement 3) or leukocyte CR3, highlighting the requirement for iC3b on tumors and CR3 on leukocytes in the tumoricidal function of β-glucans (Vetvicka, V., et al., *J. Clin. Invest.* 98:50-61 (1996) and Yan, J. V., et al., *J. Immunol.* 163:3045-3052 (1999)). Ligand binding to the β-glucan receptor results in complement activation, phagocytosis, lysosomal enzyme release, and prostaglandin, thromboxane and leukotriene generation. Most β-glucan preparations described in the prior art stimulate production of cytokines such as IL-1 and TNF, which are known to have antitumor activity. Neutral soluble β-glucan, on the other hand, does not simulate cytokine release, most likely because it is too small to cross-link membrane CR3.

Dectin-1 represents the second membrane receptor for β-glucan involved with glucan particle phagocytosis. Dectin-1 is expressed at high levels on thioglycolate-elicited peritoneal macrophages and its activity predominates over that of CR3 in the phagocytosis of yeast via β-glucan binding by these activated cells. However, yeast phagocytosis by neutrophils and resident peritoneal macrophages is blocked by anti-CR3 and does not occur with CR3-deficient (CD1 neutrophils or resident macrophages. Moreover, dectin-1 is not expressed by NK cells that use CR3 to mediate tumoricidal activity against iC3b-opsonized mammary carcinoma cells following priming with β-glucan. Thus the role of dectin-1 in mediating β-glucan activities appears to be limited to activated peritoneal macrophages and perhaps also the intestinal CR3$^{-/-}$ macrophages.

Sources of Glucan

As used herein β-glucans refer to glucose polymers that are derived from cell wall that comprises beta 1,3 and 1,6 linkages. Various forms of particulate and soluble β-glucans have been prepared.

One example of a suitable glucan source for use in the invention described herein is whole glucan particle (WGP), which is a purified, yeast cell wall preparation. Whole glucan particles are produced by removing the mannan protein outer layer and exposing the β-glucan while retaining glucan's in vivo morphology. In certain embodiments, whole glucan particles have a particle size of 1 micron or greater. Whole glucan particles are the remnants of the yeast cell wall prepared by separating growing yeast from its growth medium and subjecting the intact cell walls of the yeast to alkali, thus removing unwanted proteins and nucleic acid material.

In certain embodiments, whole glucan particles for use in the methods described herein are oral bioavailable formulations. "Bioavailable", as used herein, means the whole glucan particle is able to reach the target of action. In other words, whole glucan particles have enough β(1,3;1,6) glucan exposed for Peyer's patch uptake of the glucan. The glucan is taken up in the Peyer's patch and engulfed and degraded by macrophages, transported to the bone marrow where the degraded fragments are released. The degraded fragments bind to neutrophils in the bone marrow and through chemotaxis migrate to and bind to antibody coated tumors where complement has been activated via iC3b deposited on tumors. For example, the WGP is able to reach and act on tumor cells in combination with the antibody. At the site of action, the glucan acts to stimulate cells as a result of the binding or association of the glucan to the CR3 receptor that in turn primes or promotes the CR3 for action. The bioavailability of oral WGP is mediated by the transport of WGP to the bone marrow by gastrointestinal macrophages that degrade the particle. The degraded particles then function at the bone marrow as stimulators of neutrophils via CR3 activation when the neutrophils migrate to tumor cells and bind to iC3b on tumors.

Another example of a suitable glucan source for use in the invention described herein is microparticulate glucan particles. Microparticulate glucan particles are defined herein to be portions of whole glucan particles that result from finely grinding yeast cell wall β(1-3;1-6) glucan down to a particle size of about 1 micron or less. In certain embodiments, the whole glucan particles are used as starting material for producing soluble glucan microparticulate glucan particles, which can be formed by finely grinding yeast cell wall β(1-3;1-6) glucan down to a particle size of about 1 micron or less. Beta glucan in this form has been applied to use as a nutritional supplement and skin restorer, such as disclosed in U.S. Pat. No. 5,702,719, by Donzis. Other suitable glucan for use in the methods described herein are WGP™ Beta Glucan and BetaRight™ obtained from Biopolymer Engineering, Inc., Eagan, Minn. The preparation and methods of use of these compounds in combination with antibody for the treatment of neoplastic cells is described below.

Microparticulate β-glucan particles have also been shown to enhance the host's immune system. See U.S. Pat. Nos.

5,223,491 and 5,576,015, the teachings of which are incorporated herein by reference in their entirety.

Another form of glucan suitable for use in the methods described herein is neutral soluble β-glucans. Neutral soluble glucans are prepared through a series of acid, alkaline and neutral treatment steps to yield a conformationally pure neutral soluble glucan preparation. The neutral soluble glucan preparation enhances a host's immune system but does not induce the production of IL-1 and TNF and thus do not cause inflammation. See U.S. Pat. No. 5,783,569, the teachings of which are incorporated herein by reference in its entirety.

Preparation of WGP Glucan

Briefly, the process for producing whole glucan particles involves the extraction and purification of the alkali-insoluble whole glucan particles from the yeast or fungal cell walls. This process yields a product, which maintains the morphological and structural properties of the glucan as, found in vivo, as is referred to as a whole glucan, or whole glucan particles.

The structure-function properties of the whole glucan preparation depend directly on the source from which it is obtained and also from the purity of the final product. The source of whole glucan can be yeast or other fungi, or any other source containing glucan having the properties described herein. In certain embodiments, yeast cells are a preferred source of glucans. The yeast strains employed in the present process can be any strain of yeast, including, for example, *S. cerevisiae, S. delbrueckii, S. rosei, S. microellipsodes, S. carlsbergensis, S. bisporus, S. fermentati, S. rouxii, Schizosaccharomyces pombe, Kluyveromyces polysporus, Candida albicans, C. cloacae, C. tropicalis, C. utilis, Hansenula wingei, H. arni, H. henricii, H. americana, H. canadiensis, H. capsulata, H. polymorpha, Pichia kluyveri, P. pastoris, P. polymorpha, P. rhodanensis, P ohmeri, Torulopsis bovin*, and *T. glabrata*.

Generally, the above procedure can be used to prepare and isolate other mutant yeast strains with other parent strains as starting material. Additionally, mutagens can be employed to induce the mutations, for example, chemical mutagens, irradiation, or other DNA and recombinant manipulations. Other selection or screening techniques may be similarly employed.

The yeast cells may be produced by methods known in the art. Typical growth media comprise, for example, glucose, peptone and yeast extract. The yeast cells may be harvested and separated from the growth medium by methods typically applied to separate the biomass from the liquid medium. Such methods typically employ a solid-liquid separation process such as filtration or centrifugation. In the present process, the cells are preferably harvested in the mid-to late logarithmic phase of growth, to minimize the amount of glycogen and chitin in the yeast cells. In certain embodiments, glycogen, chitin and protein are undesirable contaminants that affect the biological and hydrodynamic properties of the whole glucan particles. In other embodiments, the glucan content of preparations are greater than 50% glucan. In certain embodiments, the remainder can be comprised of intracellular lipids and/or glycogen.

Preparation of whole glucan particles involves treating the yeast with an aqueous alkaline solution at a suitable concentration to solubilize a portion of the yeast and form an alkali-hydroxide insoluble whole glucan particles having primarily β(1-6) and β(1-3) linkages. The alkali generally employed is an alkali-metal hydroxide, such as sodium or potassium hydroxide or an equivalent. The starting material can comprise yeast separated from the growth medium. It is more difficult to control consumption of the aqueous hydroxide reactants and the concentration of reactants in the preferred ranges when starting with yeast compositions that are less concentrated. The yeast should have intact, unruptured cell walls since the preferred properties of the instant whole glucan particles depend upon an intact cell wall.

The yeast are treated in the aqueous hydroxide solution. The intracellular components and mannoprotein portion of the yeast cells are solubilized in the aqueous hydroxide solution, leaving insoluble cell wall material which is substantially devoid of protein and having a substantially unaltered three dimensional matrix of β(1-6) and β(1-3) linked glucan. The preferred conditions of performing this step result in the mannan component of the cell wall being dissolved in the aqueous hydroxide solution. The intracellular constituents are hydrolyzed and released into the soluble phase. The conditions of digestion are such that at least in a major portion of the cells, the three dimensional matrix structure of the cell walls is not destroyed. In particular circumstances, substantially all the cell wall glucan remains unaltered and intact.

In certain embodiments, the aqueous hydroxide digestion step is carried out in a hydroxide solution having initial normality of from about 0.1 to about 10.0. Typical hydroxide solutions include hydroxides of the alkali metal group and alkaline earth metals of the Periodic Table. The preferred aqueous hydroxide solutions are of sodium and potassium, due to their availability. The digestion can be carried out at a temperature of from about 20° C. to about 121° C. with lower temperatures requiring longer digestion times. When sodium hydroxide is used as the aqueous hydroxide, the temperature can be from about 80° C. to about 100° C. and the solution has an initial normality of from about 0.75 to about 1.5. The hydroxide added is in excess of the amount required, thus, no subsequent additions are necessary.

Generally from about 10 to about 500 grams of dry yeast per liter of hydroxide solution is used. In certain embodiments, the aqueous hydroxide digestion step is carried out by a series of contacting steps so that the amount of residual contaminants such as proteins are less than if only one contacting step is utilized. In certain embodiments, it is desirable to remove substantially all of the protein material from the cell. Such removal is carried out to such an extent that less than one percent of the protein remains with the insoluble cell wall glucan particles. Additional extraction steps are preferably carried out in a mild acid solution having a pH of from about 2.0 to about 6.0. Typical mild acid solutions include hydrochloric acid, sodium chloride adjusted to the required pH with hydrochloric acid and acetate buffers. Other typical mild acid solutions are in sulfuric acid and acetic acid in a suitable buffer. This extraction step is preferably carried out at a temperature of from about 20° C. to about 100° C. The digested glucan particles can be, if necessary or desired, subjected to further washings and extraction to reduce the protein and contaminant levels. After processing the product pH can be adjusted to a range of about 6.0 to about 7.8.

By conducting this process without a step of disrupting the cell walls, the extraction can be conducted at more severe conditions of pH and temperature than was possible with the prior art procedure that included a step of disrupting the cell walls. That is, the process of this invention avoids product degradation while employing these severe extraction conditions which permits elimination of time-consuming multiple extraction steps.

After the above aqueous hydroxide treatment step, the final whole glucan product comprises about 5 to about 30 percent of the initial weight of the yeast cell, preferably the product is from about 7 to about 15 percent by weight.

The aqueous hydroxide insoluble whole glucan particles produced is as set forth in the summary of the invention. The whole glucan particles can be further processed and/or further purified, as desired. For example, the glucan can be dried to a fine powder (e.g., by drying in an oven); or can be treated with organic solvents (e.g., alcohols, ether, acetone, methyl ethyl ketone, chloroform) to remove any traces or organic-soluble material, or retreated with hydroxide solution, to remove additional proteins or other impurities that may be present.

In certain embodiments, the whole glucan particles obtained from the present process are comprised of pure glucan, which consists essentially of β(1-6) and β(1-3) linked glucan. The whole glucan particles contain very little contamination from protein and glycogen. In certain embodiments, the whole glucan particles are spherical in shape with a diameter of about 2 to about 10 microns and contain greater than about 85% by weight hexose sugars, (or in other embodiments greater than about 60% hexose sugars), approximately 1% by weight protein and less that 1% of detectable amount of mannan, as determined monosaccharide analysis or other appropriate analysis. Glucans obtained by prior processes contain substantially higher quantities of chitin and glycogen than the present glucans.

The second step as set forth above, involves the modification of the whole glucan particles, as produced above, by chemical treatment to change the properties of the glucan. It is contemplated that whole glucan particles derived from any yeast strain may be used, in addition to those particular strains described herein. As mentioned above, a very broad spectrum of yeast or mutant yeast strains may be used. The processing conditions described above are also applicable to glucan extraction from fungi in general. The properties of these glucans also will depend on the sources from which they are derived.

According to a first chemical treatment, the whole glucan particles can be treated with an acid to decrease the amount of β(1-6) linkages and thus, change the hydrodynamic properties of said glucans as evidenced by an increase in the viscosity of aqueous solutions of these modified glucans.

A process for preparing an altered whole glucan particles by treating the glucan particles with an acid, for a suitable period of time to alter the β(1-6) linkages can also be used. Acetic acid is preferred, due to its mild acidity, ease of handling, low toxicity, low cost and availability, but other acids may be used. Generally these acids should be mild enough to limit hydrolysis of the β(1-3) linkages. The treatment is carried out under conditions to substantially only affect the β(1-6) linked glucans. In certain embodiments, the acid treatment is carried out with a liquid consisting essentially of acetic acid, or any dilutions thereof (typical diluents can be organic solvents or inorganic acid solutions). The treatment is carried out at a temperature of from about 20° C. to about 100° C. In certain embodiments, the treatment is carried out to such an extent to remove from about 3 to about 20 percent by weight of acid soluble material based on total weight of the whole glucan particles before treatment. In other embodiments, the extent of removal is from about 3 to about 4 percent by weight. Certain compositions formed demonstrate altered hydrodynamic properties and an enhancement in viscosity after treatment.

According to a second chemical treatment, the whole glucan particles are treated with an enzyme or an acid, to change the amount of β(1-3) linkages. For whole glucan particles derived from some yeast strains, enzyme treatment causes a decrease in the viscosity, and for others, it causes an increase in viscosity, but in general, alters the chemical and hydrodynamic properties of the resulting glucans. The treatment is with a β(1-3) glucanase enzyme, such as laminarinase, for altering the β(1-3) linkages to alter the hydrodynamic properties of the whole glucan particles in aqueous suspensions.

The enzyme treatment can be carried out in an aqueous solution having a concentration of glucan of from about 0.1 to about 10.0 grams per liter. Any hydrolytic glucanase enzyme can be used, such as laminarinase, which is effective and readily available. The time of incubation may vary depending on the concentration of whole glucan particles and glucanase enzyme. The 3(1-3) linkages are resistant to hydrolysis by mild acids such as acetic acid. Treatment with strong or concentrated acids, such as hydrochloric acid (HCl), sulfuric acid ($H_2SO_4$) or formic acid, hydrolyzes the β(1-3) linkages thereby reducing the amount of β(1-3) linkages. The acid treatment can be carried out in an aqueous solution having a concentration of glucan from about 0.1 to about 10.0 grams per liter. The time of acid treatment may vary depending upon the concentration of whole glucan particles and acid. Acid hydrolysis can be carried out at a temperature of from about 20° C. to about 100° C. The preferred compositions formed demonstrate altered hydrodynamic properties.

By controlling the incubation time, it is possible to control the chemical and hydrodynamic properties of the resulting product. For example, the product viscosity can be precisely controlled for particular usage, as, for example, with a variety of food products.

A hydrodynamic parameter ($K_1$) of the final treated product having altered linkages is dependent on the treatment time according to the final formula:

$$K_1 = -0.0021(\text{time}) + 0.26$$

where time is in minutes; and
where time is less than one hour.

The parameter $K_1$ is directly related (proportional) to the relative viscosity.

In the case of aqueous suspensions the relative viscosity is equal to the actual viscosity when the latter is measured in centipoise.

A process for preparing aqueous slurry of a glucan having a predetermined desired viscosity is provided. The slurry comprises glucan at a concentration that is a function of the predetermined desired viscosity according to the following approximate formula:

$$1/\text{concentration} = K_1 \times (1/\log(\text{relative viscosity})) + K_2$$

Where,
$K_1$ = (shape factor)×(hydrodynamic volume); and
$K_2$ = (hydrodynamic volume)/(maximum packing fraction).

The shape factor is an empirically determined value that describes the shape of the glucan matrix in its aqueous environment. The shape factor is a function of the length: width ratio of a particle and can be determined microscopically. The hydrodynamic volume is a measure of the volume a particle occupies when in suspension. This is an important parameter for glucan suspensions in that it indicates the high water holding capacity of glucan matrices. The maximum packing fraction can be described as the highest attainable volume fraction of glucans that can be packed into a unit volume of suspension.

Preparation of microparticulate β-glucan particles

Beta (1,3) glucan starting material can be isolated from yeast cell walls by conventional methods known by those of ordinary skill in the art. The general method for the production of glucan from yeast involves extraction with alkali followed by extraction with acid (Hassid et al., *Journal of the American Chemical Society,* 63:295-298, 1941). Improved methods for isolating a purified water insoluble beta (1,3) glucan extract are disclosed in U.S. Pat. No. 5,223,491, which is incorporated herein by reference in its entirety. Methods for preparing microparticulate β-glucan particles are disclosed in U.S. Pat. No. 5,702,719, the disclosure of which is incorporated herein by reference in its entirety. Microparticulate glucan product can also be obtained with the average particle size of about 1.0 microns or less or about 0.20 microns or less.

Beta glucan particles can be reduced in size by mechanical means such as by, using a blender, microfluidizer, or ball mill, for example. For example, particle size can be reduced using a blender having blunt blades, wherein the glucan mixture is blended for a sufficient amount of time, preferably several minutes, to completely grind the particles to the desired size without overheating the mixture. Another grinding method comprises grinding the glucan mixture in a ball mill with 10 mm stainless steel grinding balls. This latter grinding method is particularly preferred when a particle size of about 0.20 microns or less is desired.

Prior to grinding, the glucan mixture is preferably passed through a series of sieves, each successive sieve having a smaller mesh size than the former, with the final mesh size being about 80. The purpose of sieving the mixture is to separate the much larger and more course glucan particles from smaller particles (the pore size of an 80 mesh sieve is about 0.007 inches or 0.178 mm). The separated larger particles are then ground down as described above and re-sieved to a final mesh size of 80. The process of sieving and grinding is repeated until a final mesh size of 80 is obtained. The sieved particles are combined and ground down further, preferably for at least an hour, until the desired particle size is obtained, preferably about 1.0 micron or less, more preferably about 0.20 microns or less. Periodic samples of the fine grind glucan are taken during the grinding process and measured using a micrometer on a microscope.

Soluble Glucan

Another, more processed form of β(1,3;1,6)glucan is neutral soluble β-glucan (NSG). Generally, neutral underivatized β(1,3;1,6) glucans are not soluble in physiological media due to their tendency to form tightly associated triple helix fibrils which resist hydration. Neutral soluble β-glucan is prepared from whole glucan particles through a series of acid, alkaline and neutral treatment steps to yield a conformationally pure, soluble glucan preparation that can be maintained in a clear solution. Methods of producing NSG are known in the art and are disclosed in U.S. Pat. No. 5,322,841, the contents of which is incorporated herein by reference. The soluble glucans produced by this process are branched polymers of glucose, containing β(1-3) and β(1-6) linkages in varying ratios depending on the source organism and the exact processing conditions used. The average molecular weight of NSGs is generally about 5,000 to 500,000 daltons. NSG enhances a host's immune system in a variety of ways. However, NSG does not stimulate production of cytokines such as interleukin-1 (IL-1) and tumor necrosis factor (TNF) and thus does not cause inflammation. See U.S. Pat. No. 5,783,569, the teachings of which are incorporated herein by reference. WGP can be further broken down into various components, each with differing affinities for binding to subsets of receptors found on innate immune cells. These various conformational forms are, in increasing order of complexity, random coil, single helix, triple helix, and triple helical multimer. In certain embodiments, the triple helix conformation is about 150,000 molecular weight. The higher molecular weight conformers of neutral soluble glucan do not bind CR3 but can be phagocytosed and degraded to smaller fragments that are able to bind to CR3. WGP has shown a variety of biological activities, including use as a vaccine adjuvant (U.S. Pat. No. 5,741,495), an anti-infective agent (Pedroso M., *Arch. Med. Res.* 25(2), 181 (1994)), and an antitumor agent (Borchers, A. T., et al., *Proc. Soc. Exp. Biol. Med.,* 221(4), 281 (1999)). Each conformational form possesses different activities as is demonstrated by the different specificities observed for glucan receptors.

Preparation of Neutral Soluble Glucan

The preparation of neutral soluble glucan (NSG) is described in U.S. Pat. No. 5,322,841, the disclosure of which is incorporated herein by reference. Briefly, this method involves treating whole glucan particles with a series of acid and alkaline treatments to produce soluble glucan that forms a clear solution at a neutral pH. The whole glucan particles utilized in this present invention can be in the form of a dried powder, prepared by the process described above. For the purpose of this present invention it is not necessary to conduct the final organic extraction and wash steps.

In the present process, whole glucan particles are suspended in an acid solution under conditions sufficient to dissolve the acid-soluble glucan portion. For most glucans, an acid solution having a pH of from about 1 to about 5 and a temperature of from about 20° to about 100° C. is sufficient. Preferably, the acid used is an organic acid capable of dissolving the acid-soluble glucan portion. Acetic acid, at concentrations of from about 0.1 to about 5M or formic acid at concentrations of from about 50% to 98% (w/v) are useful for this purpose. Additionally, sulphuric acid can be utilized. The treatment is preferably carried out at about 90° C. The treatment time may vary from about 1 hour to about 20 hours depending on the acid concentration, temperature and source of whole glucan particles. For example, modified glucans having more β(1-6) branching than naturally-occurring, or wild-type glucans, require more stringent conditions, i.e., longer exposure times and higher temperatures. This acid-treatment step can be repeated under similar or variable conditions. In one embodiment of the present method, modified whole glucan particles from the strain, *S. cerevisiae* R4, which have a higher level of β(1-6) branching than naturally-occuring glucans, are used, and treatment is carried out twice: first with 0.5M acetic acid at 90° C. for 3 hours and second with 0.5M acetic acid at 90° C. for 20 hours.

The acid-insoluble glucan particles are then separated from the solution by an appropriate separation technique, for example, by centrifugation or filtration. The pH of the resulting slurry is adjusted with an alkaline compound such as sodium hydroxide, to a pH of about 7 to about 14. The slurry is then resuspended in hot alkali having a concentration and temperature sufficient to solubilize the glucan polymers. Alkaline compounds which can be used in this step include alkali-metal or alkali-earth metal hydroxides, such as sodium hydroxide or potassium hydroxide, having a concentration of from about 0.1 to about 10N. This step can be conducted at a temperature of from about 4° C. to about 121° C., preferably from about 20° C. to about 100° C. In one embodiment of the process, the conditions utilized are a 1N solution of sodium hydroxide at a temperature of about 80°-100° C. and a contact time of approximately 1-2 hours. The resulting mixture contains solubilized glucan molecules and particulate glucan residue and generally has a dark brown color due to oxidation of contaminating proteins and sugars. The particulate residue is removed from the mixture by an appropriate separation technique, e.g., centrifugation and/or filtration.

The resulting solution contains soluble glucan molecules. This solution can, optionally, be concentrated to effect a 5 to 10 fold concentration of the retentate soluble glucan fraction to obtain a soluble glucan concentration in the range of about 1 to 5 mg/ml. This step can be carried out by an appropriate concentration technique, for example, by ultrafiltration, utilizing membranes with nominal molecular weight levels (NMWL) or cut-offs in the range of about 1,000 to 100,000 daltons. A membrane cut-off of about 10,000 daltons is particularly useful for this step.

The concentrated fraction obtained after this step is enriched in the soluble, biologically active glucan, also referred to as, PGG. To obtain a pharmacologically acceptable solution, the glucan concentrate is further purified, for example, by diafiltration. In one embodiment, diafiltration is carried out using approximately 10 volumes of alkali in the range of about 0.2 to 0.4N. The preferred concentration of the soluble glucan after this step is from about 2 to about 5 mg/ml. The pH of the solution is adjusted in the range of about 7-9 with an acid, such as hydrochloric acid. Traces of proteinaceous material which may be present can be removed by contacting the resulting solution with a positively charged medium such as DEAE-cellulose, QAE-cellulose or Q-Sepharose. Proteinaceous material is detrimental to the quality of the glucan product, may produce a discoloration of the solution and aids in the formation of gel networks, thus limiting the solubility of the neutral glucan polymers. A clear solution is obtained after this step.

The highly purified, clear glucan solution can be further purified, for example, by diafiltration, using a pharmaceutically acceptable medium (e.g., sterile water for injection, phosphate-buffered saline (PBS), isotonic saline, dextrose) suitable for parenteral administration. The preferred membrane for this diafiltration step has a nominal molecular weight cut-off of about 10,000 daltons. The final concentration of the glucan solution is adjusted in the range of about 0.5 to 5 mg/ml. In accordance with pharmaceutical manufacturing standards for parenteral products, the solution can be terminally sterilized by filtration through a 0.22 μm filter. The soluble glucan preparation obtained by this process is sterile, non-antigenic, and essentially pyrogen-free, and can be stored at room temperature for extended periods of time without degradation.

Complement Activating Antibodies

Complement activating antibodies (both naturally found or produced by methods known in the art) are antibodies directed to the tumor or tumor antigens that are able to activate one or more members of the complement cascade. In other words, an antibody that activates complement sufficiently to deposit iC3b on the tumor cells is needed. In certain embodiments, the antibodies are IgG subclass I or IgG subclass III.

The present invention discloses the use of NSG with antibodies from essentially any source, including antibodies generated naturally in response to infection, antibodies generated in response to administration of a vaccine, and monoclonal antibodies directly administered as part of a therapy including the use of β-glucan. Any antibody having complement activating features can be used in the methods described herein to enhance beta-glucan on tumorcidal activity. Murine antibodies can be raised against any antigen associated with neoplastic (tumor) cells using techniques known in the art. In this regard, tumor cells express increased numbers of various receptors for molecules which can augment their proliferation, many of which are the products of oncogenes. Thus, a number of monoclonal antibodies have been prepared which are directed against receptors for proteins such as transferring, IL-2, and epidermal growth factor. Any antibody which can selectively label antigen and can activate complement can have its activity enhanced through concurrent administration with β-glucan. This includes antibodies of the various classes, such as IgA, IgD, IgE, and IgM, as well as antibody fragments such as Fab.

The term "antibody" as used herein refers to immunoglobulin molecules and imnunologically active portions of immunoglobulin molecules, i.e., molecules that contain an antigen binding site that specifically binds a tumor antigen. A molecule that specifically binds to tumor is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The term "monoclonal antibody" or "monoclonal antibody composition", as used herein, refers to a population of antibody molecules that contain only one species of an antigen binding site capable of immunoreacting with a particular epitope of a target tumor. A monoclonal antibody composition thus typically displays a single binding affinity for a particular polypeptide of the invention with which it immunoreacts.

Polyclonal antibodies can be prepared as described above by immunizing a suitable subject with a desired immunogen, e.g., polypeptide of the invention or fragment thereof. The antibody titer in the immunized subject can be monitored over time by standard techniques, such as with an enzyme linked immunosorbent assay (ELISA) using immobilized polypeptide. If desired, the antibody molecules directed against the polypeptide can be isolated from the mammal (e.g., from the blood) and further purified by well-known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature,* 256:495-497, the human B cell hybridoma technique (Kozbor et al. (1983) *Immunol. Today,* 4:72), the EBV-hybridoma technique (Cole et al. (1985), *Monoclonal Antibodies and Cancer Therapy*, Alan R. Liss, Inc., pp. 77-96) or trioma techniques. The technology for producing hybridomas is well known (see generally *Current Protocols in Immunology* (1994) Coligan et al. (eds.) John Wiley & Sons, Inc., New York, N.Y.). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds a polypeptide of the invention.

Any of the many well known protocols used for fusing lymphocytes and immortalized cell lines can be applied for the purpose of generating a monoclonal antibody to a polypeptide of the invention (see, e.g., *Current Protocols in*

Immunology, supra; Galfre et al. (1977) *Nature,* 266:55052; R. H. Kenneth, in *Monoclonal Antibodies: A New Dimension In Biological Analyses,* Plenum Publishing Corp., New York, N.Y. (1980); and Lerner (1981) *Yale J. Biol. Med.,* 54:387-402. Moreover, the ordinarily skilled worker will appreciate that there are many variations of such methods that also would be useful.

Alternative to preparing monoclonal antibody-secreting hybridomas, a monoclonal antibody to a polypeptide of the invention can be identified and isolated by screening a recombinant combinatorial immunoglobulin library (e.g., an antibody phage display library) with the polypeptide to thereby isolate immunoglobulin library members that bind the polypeptide. Kits for generating and screening phage display libraries are commercially available (e.g., the Pharmacia *Recombinant Phage Antibody System,* Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology,* 9:1370-1372; Hay et al. (1992) *Hum. Antibod. Hybridomas,* 3:81-85; Huse et al. (1989) *Science,* 246:1275-1281; Griffiths et al. (1993) *EMBO J.,* 12:725-734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art.

As illustrative of the inventive concept, β-glucans such as NSG could be administered to act synergistically with Herceptin™, a monoclonal antibody sold by Genentech for use in immunotherapy of breast cancer. Herceptin™ is a mAb that recognizes the her2 cell surface antigen which is present on 20% of breast cancer cell types. Clinical trials have demonstrated that Herceptin™ is saving lives, but its effectiveness could be significantly enhanced through concurrent administration of β-glucan. NSG therapy along with Herceptin™ therapy could result in a significant increase in the proportion of women responding to Herceptin™ therapy with long lasting remission of their breast cancer. Currently, only 15% of women receiving Herceptin™ therapy show long lasting remission.

Another mAb whose activity is enhanced by β-glucan is rituximab, a monoclonal antibody used to treat a type of non-Hodkin's lymphoma (NHL), a cancer of the immune system. Rituximab is effective for patients with low-grade B-cell NHL who have not responded to standard treatments. It targets and destroys white blood cells (B-cells) which have been transformed, resulting in cancerous growth. Rituximab is a genetically engineered version of a mouse antibody that contains both human and mouse components. In the main clinical study of 166 patients with advanced low-grade or slow-growing NHL, which represents about 50% of the 240,000 NHL patients in the United States, tumors shrunk by at least one half in 48% of the patients who completed treatment with rituximab, with 6% having complete remission. Beta-glucan can be expected to significantly increase the effectiveness of this treatment, by enhancing the destruction of antibody-marked tumor cells.

Formulation and Administration

The administration of the neutral soluble glucan and complement activating antibodies can be administered sequentially, co-administered or in multiple dosing. Further, the order of administration is interchangeable and the antibody can be naturally existing.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g., PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein in its entirety. Techniques and compositions for making dosage forms useful in the present invention are described in the following references: 7 Modem Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

All publications cited are incorporated by reference in their entirety. The present invention is now illustrated by the following Exemplification, which is not intended to be limiting in any way.

EXEMPLIFICATION

CR3 plays a very important role in the antitumor activity of β-glucan. The role of CR3 in mediating the response to β-glucan was shown by research into the mechanisms of neutrophil phagocytosis of iC3b-opsonized yeast. When complement C3b has attached itself to a surface, it may be clipped by a serum protein to produce a smaller fragment, iC3b. While iC3b has been "inactivated" and cannot function to form a membrane attack complex, it remains attached to the surface where it serves to attract neutrophils and macrophages which can phagocytize or otherwise destroy the marked ("opsonized") cell. On the surface of neutrophils and macrophages are complement receptors (CR3) that bind to iC3b. The process by which yeast is eliminated by the immune system is illustrated in FIG. 1.

Figure 2:
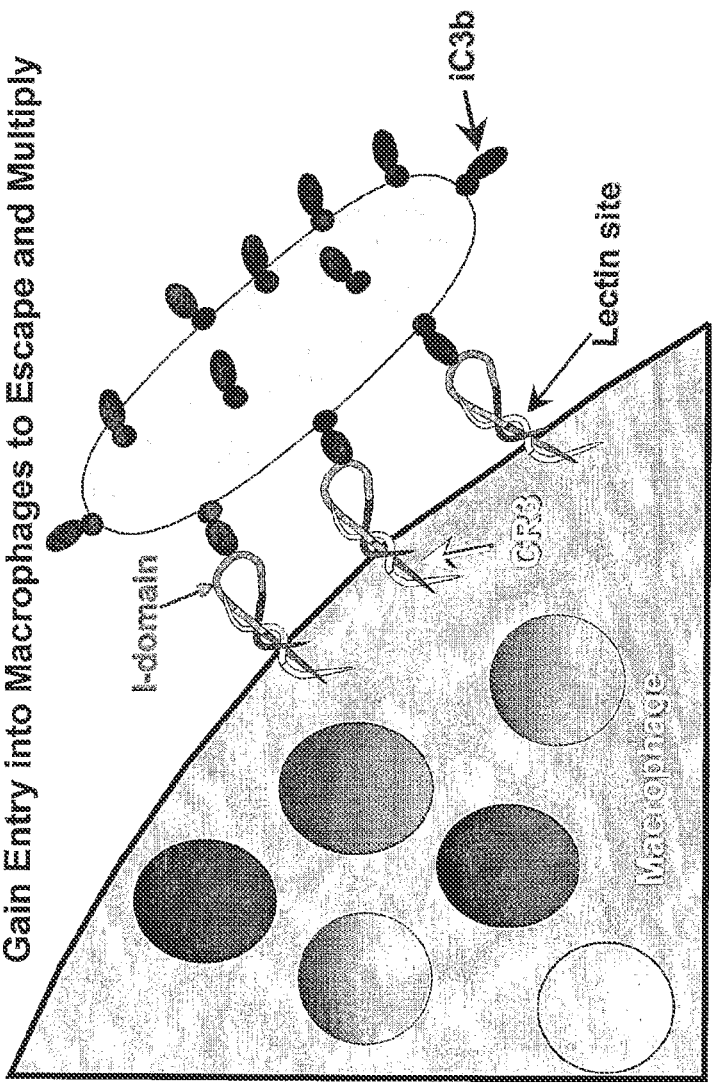
FIG. 2 is a drawing showing that bacteria lacking β-glucans do not trigger phagocytosis or degranulation via CR3.
Figure 3:
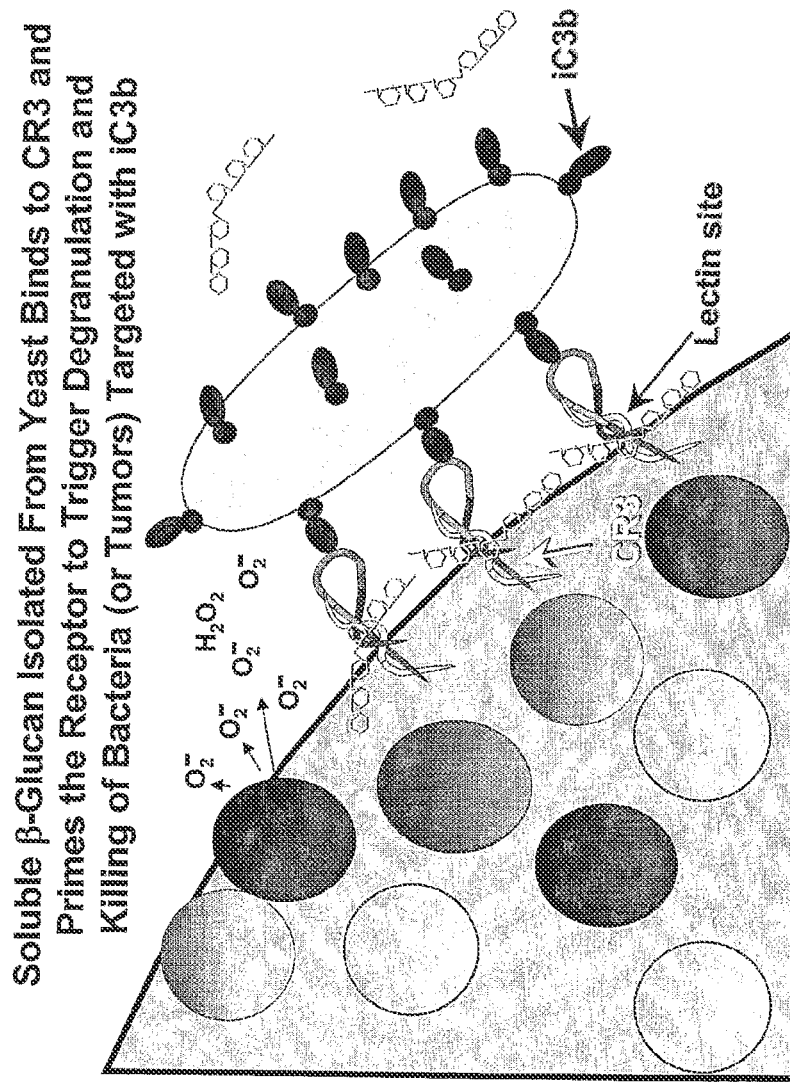
FIG. 3 is a drawing showing that soluble β-glucan binds to CR3 and primes the receptor to trigger degranulation and destruction of bacteria or tumor cells targeted with iC3b.

Stimulation of CR3-dependent phagocytosis or degranulation requires the simultaneous ligation of two distinct sites within CR3; one specific for iC3b and a second site specific for yeast cell wall b-glucan. As illustrated in FIG. 2, because they lack cell-surface CR3-binding β-glucan, bacterial opsonized with iC3b are bound to neutrophils via CR3 but do not stimulate phagocytosis or degranulation. However, as illustrated in FIG. 3, addition of β-glucans can bind to the lectin site of CR3 to activate immune cells bearing the receptor to trigger degranulation and or phagocytosis of the foreign material. Soluble zymosan-derived polysaccharides rich in mannans and β-glucans have been shown to bind to CR3 with high affinity, inducing a primed receptor state.

Figure 4:
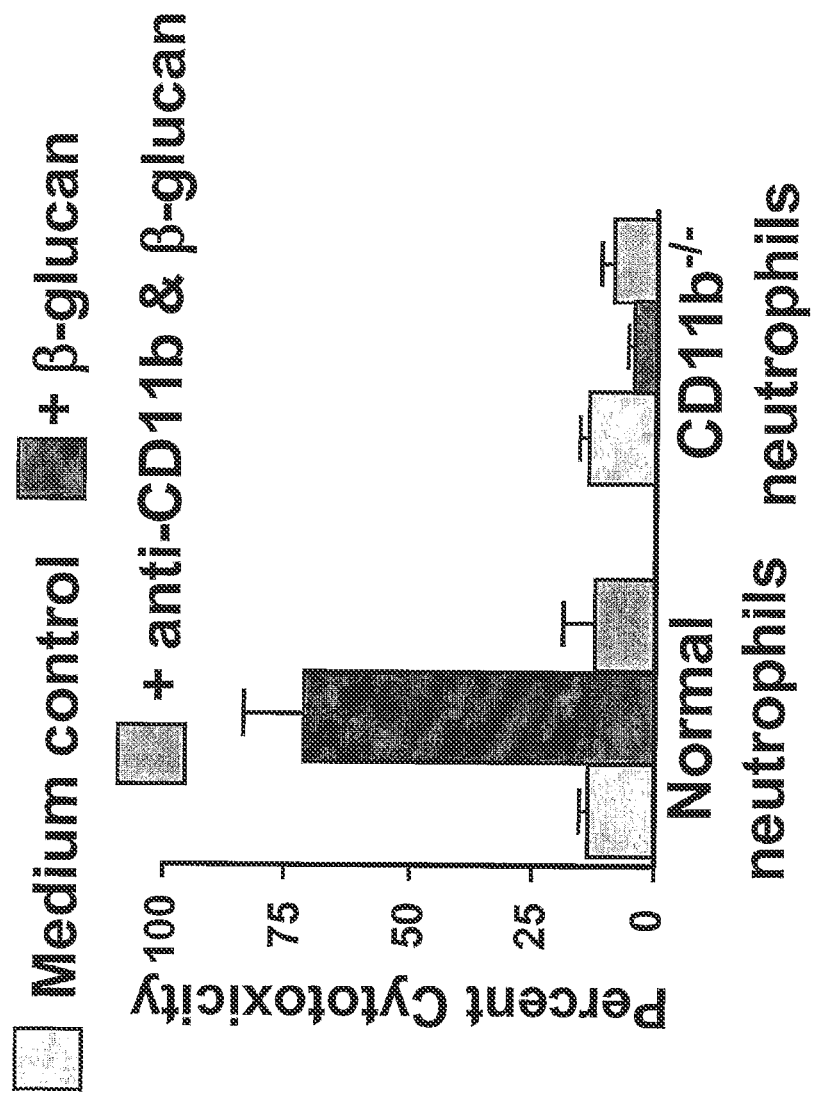
FIG. 4 is a graph showing that β-glucan priming of murine neutrophil CR3 allows subsequent cytotoxic triggering by iC3b-opsonized breast tumor cells.

The effect of β glucan priming of murine neutrophil CR3 on subsequent cytotoxic triggering by iC3b-opsonized breast tumor cells is shown in FIG. 4. When normal neutrophils are used, addition of β-glucan creates a high level of cytotoxicity towards iC3b-opsonized breast tumor cells. This activity disappears, however, when antibody to the CD11b (murineCR3 equivalent) is added, interfering with the receptor's ability to bind to iC3b. On the right side of the graph, it is demonstrated that neutrophils from CD11b-deficient mice are unable to mediate cytotoxicity of iC3b-opsonized mice even when stimulated with β-glucan, again demonstrating the crucial importance of this receptor. Adding antibody against CD11b had little effect on CD11b-deficient neutrophils, as expected.

Figure 5:
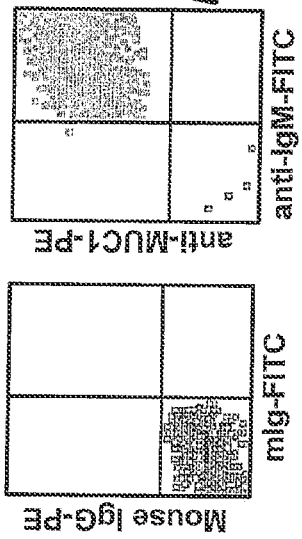
FIGS. 5A-5D are a series of graphs showing the flow cytometric analysis of tumor cells from a patient with mammary carcinoma for IgM, IgG, or C3.

FIG. 5 illustrates that tumor cells are coated with IgG, IgM, and C3. This is interesting because it shows that a weak adaptive immune response is occurring against these tumor cells, and that if this labeling could be used to trigger a cytotoxic response tumor growth could be inhibited or eliminated. Flow cytometry was used to distinguish breast tumor cells from normal breast epithelial cells, and then to show that most tumor cells bear IgG, IgM, and C3. Single cell suspensions of freshly excised tumors from two patients were analyzed. FIG. 5 shows the results obtained with the tumor from one of the patients. Malignant cells were distinguished from normal breast epithelial cells by staining with biotinylated anti-mucin (MUC1)-biotin mAb BrE-3 followed by streptavidin phycoerythrin. Two-color analysis was then used to determine the presence of IgG, IgM, and C3 on malignant MUC1-positive cells by double staining with antibodies coupled to fluorescein isothiocyanate (FITC). As can be seen, most of the MUC1-positive cells bore IgG, IgM, and C3. Only a small proportion of the MUC1-positive cells appeared to be negative for opsonization with C3. Little, if any, C3 or Ig staining was detected on MUC1-negative cells, which represent normal breast epithelial cells.

In the present invention, β-glucan in different forms is disclosed as having different, synergistic affects on the immune system. Immune cells respond to both soluble and particulate β-glucan via CR3. However, the response differs to these two different forms of β-glucan. CR3 is expressed on neutrophils, monocytes, macrophages, eosinophils, NK cells, dendritic cells, and some T cells. Soluble β-glucan (e.g., NSG) binds to CR3 and primes the iC3b-receptor in such a way that it is able to trigger leukocytes to kill tumor cells or microorganisms coating with the CR3 target ligand iC3b. Particulate β-glucan (e.g., WPG), on the other hand, binds to CR3, stimulating neutrophil degranulation and stimulating macrophages to secrete several cytokines that promote a Th1-type T cell response and long-lasting immunity to tumors or microorganisms. Particular β-glucan can also prime CR3 for cytotoxicity in vitro or in vivo.

Figure 6:
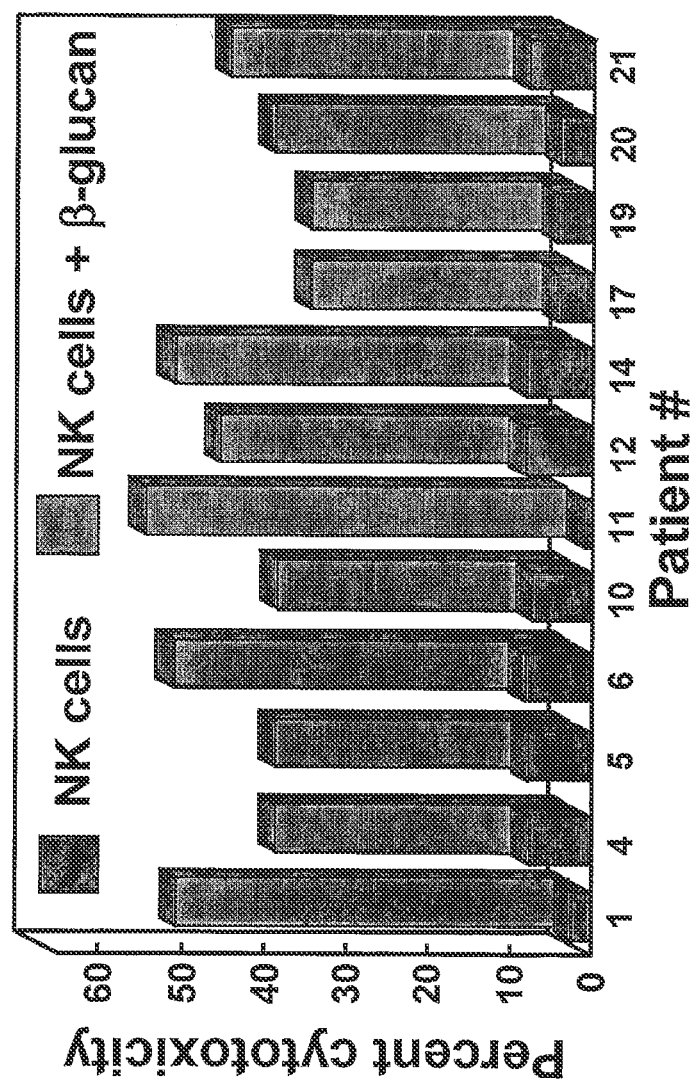
FIG. 6 is a graph showing that suspensions of freshly excised primary mammary tumor cells bear sufficient C3 for cytotoxic recognition by allogeneic NK cells bearing β-glucan primed CR3.

NK cells are an important component of the innate immune system, and can kill tumor cells by stimulating apoptosis through the Fas ligand or through formation of a MAC complex and insertion of apoptosis-inducing enzymes. NK cells complement the activity of macrophages by targeting cells which have lost their MHC proteins through tumor or viral action. Target cell-bound C3 is also required for NK cell CR3-dependent cytotoxicity. FIG. 6, tests were conducted with freshly excised tumors from 12 patients to determine whether the tumor cells bore sufficient amounts of C3 for recognition and cytotoxicity by NK cells bearing soluble zymosan polysaccharide (SZP)-primed CR3. Fresh and viable tumor cell suspensions were labeled with $^{51}$Cr and tested for susceptibility to the cytotoxicity of NK cells isolated from a normal, unrelated donor during a 4 hour incubation period at 37° C. It also demonstrates the powerful enhancement of NK cell activity by addition of β-glucan in the form of SZP. Although no significant cytotoxicity was observed with unstimulated NK cells, priming the cells with 2.0 µg/ml of SZP resulted in 32 to 54% cytotoxicity. The presence of C3-negative normal breast epithelial cells that were surgically removed along with the tumor probably prevented higher levels of cytotoxicity from being shown.

Figure 7:
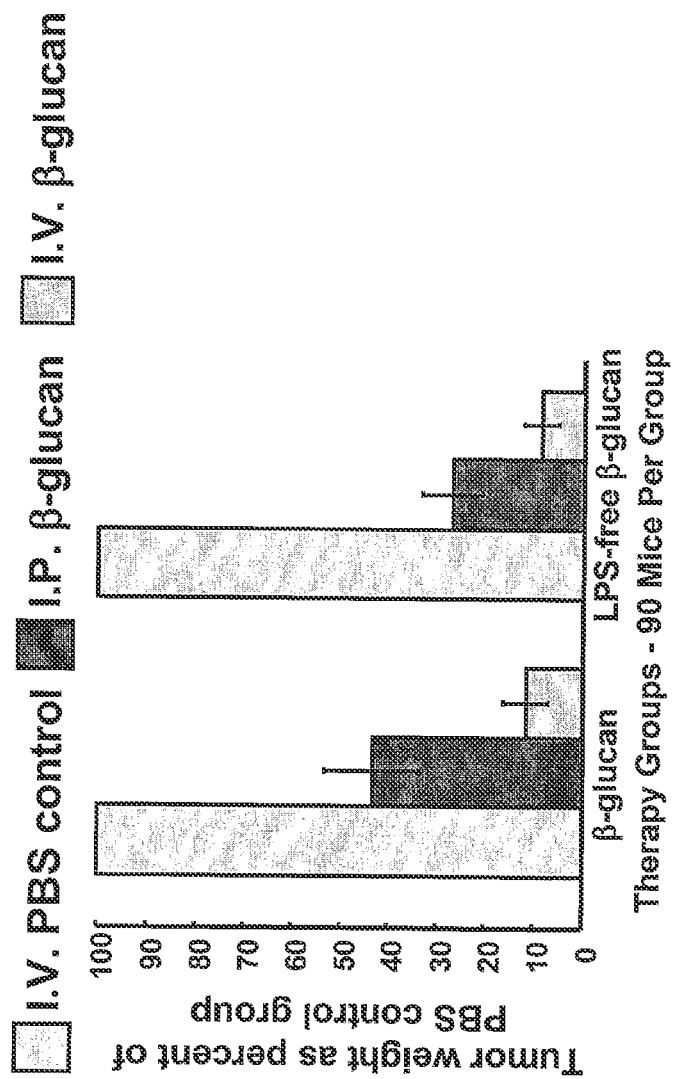
FIG. 7 is a graph showing the results of β-glucan therapy of Ptas64 mammary carcinoma in Balb/c Mice.

The efficacy of β-glucan therapy is demonstrated in FIG. 7, which shows the results of β-glucan therapy of Ptas64 mammary carcinoma in Balb/c mice. $SZP_m$ (soluble zymosan polysaccharide rich in β-mannans) was used as the β-glucan source in this experiment. Ptas64 mammary carcinoma was implanted in Balb/c mice. For each of six experiments, two groups of 6 mice were given daily i.p. or i.v. injections of 200 µg of $SZP_m$. A control group of 6 mice received daily i.v. phosphate buffered saline (PBS). Three experiments with 30 mice were carried out with $SZP_m$, and then the same experiment was done 3 more times with another 90 mice using LPS-free $SZP_m$. For each experiment, the average tumor weight for the therapy groups was determined and compared to the average weight of tumors removed from the PBS control group. Each bar in FIG. 7 represents the mean±SD for each therapy group. As can be seen, tumor weight was dramatically reduced to 40 and 10% for i.p. and i.v. administration of β-glucan, respectively. Furthermore, the experiments with LPS-free $SZP_m$ demonstrate that this activity is not due to LPS, which is a well known immunostimulant.

Figure 8:
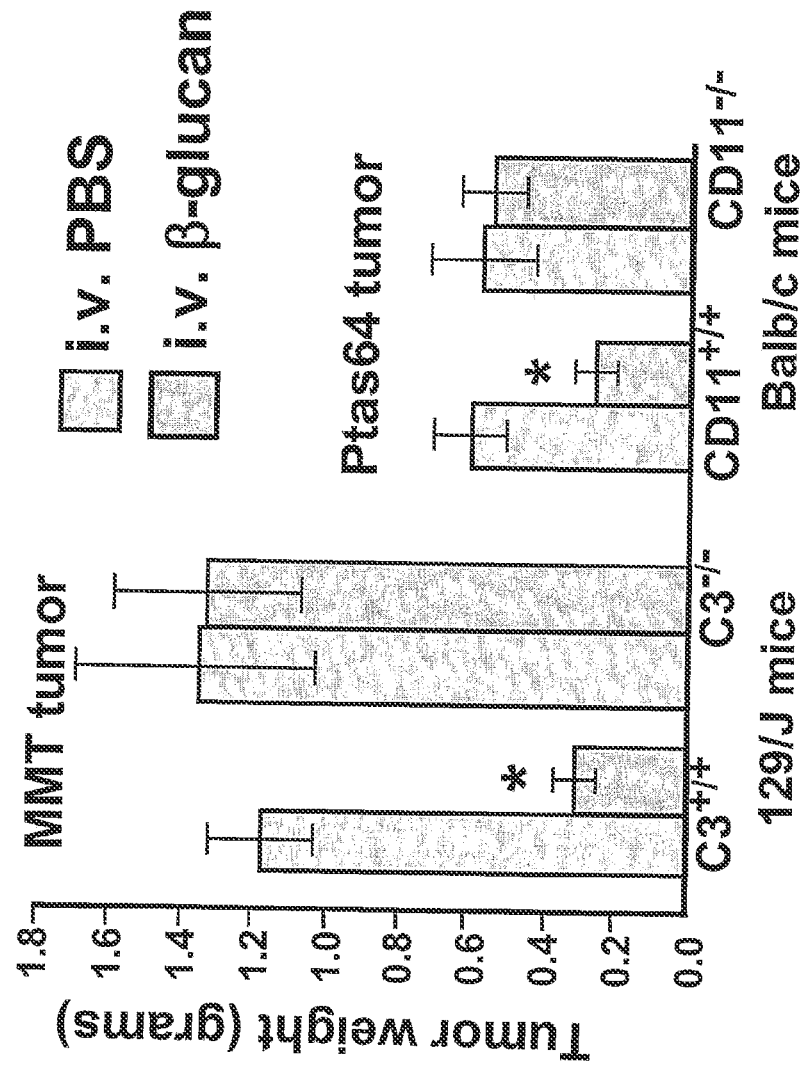
FIG. 8 is a graph showing the failure of β-glucan tumor therapy in mice deficient in serum C3 or leukocyte CR3.

FIG. 8 demonstrates that β-glucan therapy requires both C3 on tumor cells and CR3 on leukocytes. The requirement for C3 in β-glucan therapy was confirmed in experiments with C3-deficient 129/J mice implanted with the MMT mammary carcinoma. Twelve normal (C3+/+) and 12 C3-deficient (C3−/−) 129/J mice were implanted with the MMT mammary carcinoma tumor cell line and palpable tumors were allowed to form before beginning daily i.v. therapy of groups of 6 mice each with PBS or β-glucan. A similar protocol was used with normal (CD+/+) and CR3-deficient (CD11b-knockout; Cd11b−/−) BALB/c mice implanted with Ptas64 mammary tumors. Beta-glucan therapy of normal 129/J mice resulted in a 79% tumor reduction, as shown in the FIG., similar to that of normal BALB/c mice. Flow cytometry of the tumors showed an abundant deposition of C3 on >80% of cells. By contrast, in C3-deficient 129/J mice, there was no significant tumor reduction and no C3 present on the tumors. The relative amount of IgG present on the tumors, as demonstrated by staining, did not differ between normal and C3-deficient mice.

Figure 9:
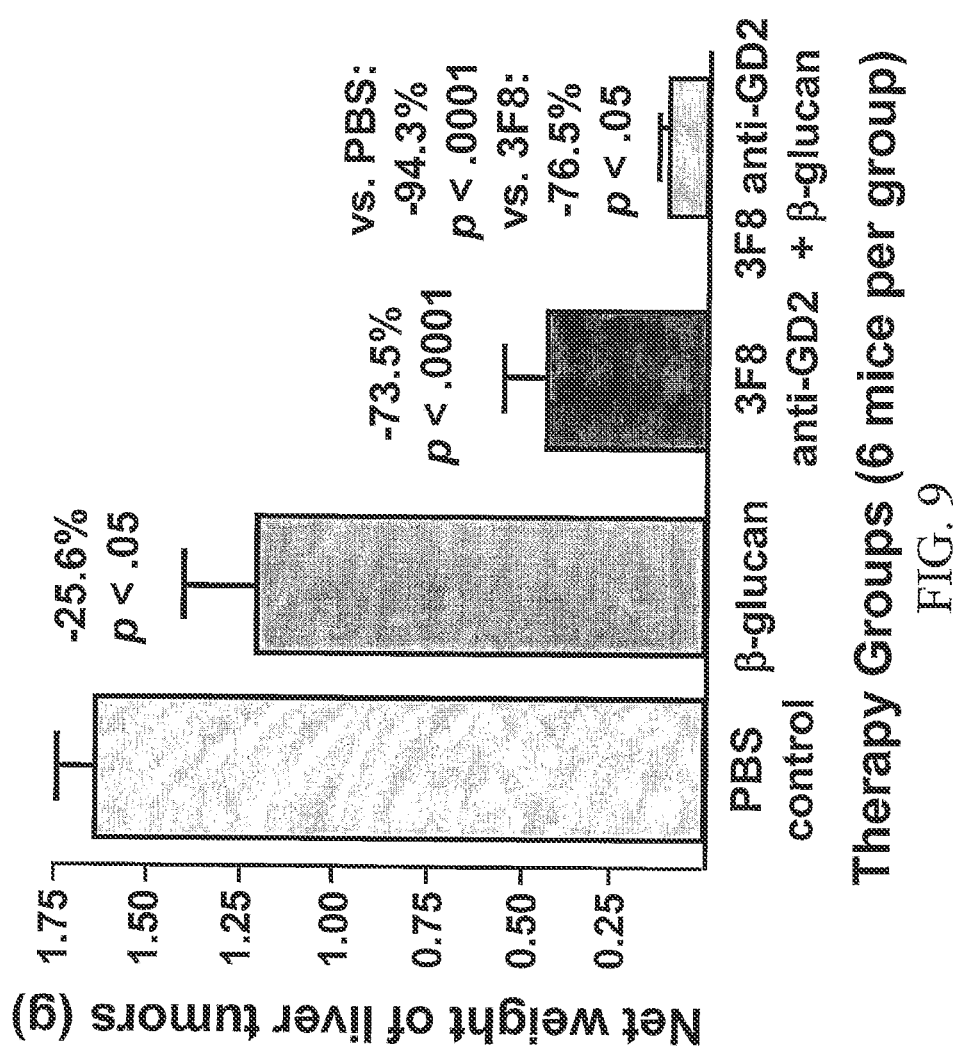
FIG. 9 is a graph showing the enhancement of anti-tumor mAb therapy of hepatic EL-4 lymphoma with β-glucan.

The next step was to demonstrate that β-glucan could be used to enhance mAb therapy. The results of these experiments are shown in FIG. 9, which shows the enhancement of anti-tumor mAb therapy of hepatic EL-4 lymphoma with β-glucan. The EL-4 lymphoma was tested for a response to b-glucan therapy because, unlike other tumors, the syngeneic host (C57BL/6) did not express natural Abs that opsonized the tumor cells with C3. Mice were injected with the EL-4 cells i.v., a protocol known to result in liver metastases. Ten days later, the mice were given daily i.v. doses of β-glucan alone, 3F8 mAb to GD2 ganglioside (a prominent tumor antigen of EL-4 cells), or 3-glucan plus 3F8 mAb. The 3F8 mAb is IgG3 and is a potent activator of complement and also mediates ADCC. As other had shown, 3F8 alone caused a significant reduction (73.5%) in EL-4 liver tumors. As expected, the β-glucan had little effect on its own since the tumors bore little or no iC3b. However, the combination of β-glucan with 3F8 produced a significantly greater reduction in liver tumor compared to 3F8 alone.

Figure 10:
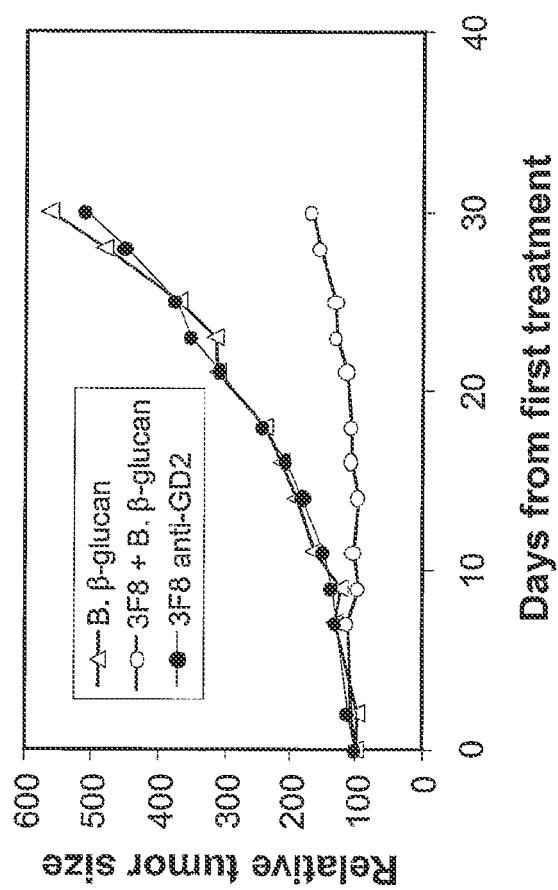
FIG. 10 is a graph showing the synergy of oral barley β-glucan therapy with antibody against human LAN-1 neuroblastoma in nude mice.

FIG. 10 demonstrates that β-glucan from barley (which produces the unusual (1,3),(1,4)-β-D-glucan) can also enhance the antitumor activity of mAbs. Neuroblastoma cells were xenografted subcutaneously in athymic BALB/c mice. Treatment started in groups of 5 mice, 2 weeks after tumor implantation when visible tumors reached 0.7-0.8 cm in diameter. The β-glucan groups was treated with 400 g daily by gavage for a total of 21-29 days. Monoclonal antibodies (3F8) were administered i.v. at a dose of 200 g twice weekly. Tumor size was measured from the first day of treatment, and the product of the largest diameter was expressed as a percentage of the size on day zero. As can be seen, neither β-glucan or mAb alone showed much effect. However, when the two are combined, tumor growth is clearly suppressed.

TABLE 1

Sugar and CR3 specificity of neutrophil fluorescence staining by FITC-labeled polysaccharides

| Type of FITC-Labeled Polysaccharide | Polysaccharide-FITC Concentration Required for Maximum Specific Fluorescence Staining (Saturation of Receptor Binding Sites) (µg/ml) | Specific Fluorescence Mean Channel at Saturation (Total-Nonspecific Fluorescence Obtained in the Presence of Excess of Unlabeled Polysaccharide) | % inhibition of Specific Fluorescence by SZP (50 µg/ml) | MN-41 anti-CR3 (50 µg/ml) |
|---|---|---|---|---|
| Dextran-FITC | No specific staining | 0 | ND | ND |
| α-Mannan-FITC | No specific staining | 0 | ND | ND |
| Barley β-glucan-FITC | 10 | 12.8 | 92.3 | 94.5 |
| CM β-glucan-FITC | 5 | 22.2 | 87.8 | 78.9 |
| Laminarin-FITC | 10 | 38.2 | 91.5 | 89.9 |
| Lentinan-FITC | 5 | 21.5 | 96.3 | 81.0 |
| MP β-glucan-FITC | 2 | 50.9 | 100 | 96.1 |
| SZP-FITC | 2 | 175 | 99.8 | 77.4 |

Table 1 shows the sugar specificity of β-glucan from various sources and also shows the results of flow cytometry with various pure β-glucan-FITC preparations. No specific staining was obtained with dextran-FITC or α-mannan-FITC. Even though each polysaccharide-FITC preparation produced a lower intensity of neutrophil staining than did SZP-FITC, the fluorescence of each polysaccharide-FITC was similarly inhibited by excess unlabeled homologous β-glucan, unlabeled SZP, or anti-CR3. Comparison of polysaccharide concentrations required for maximum staining suggested that SZP or MP β-glucan (a soluble β-glucan obtained from Molecular Probes) had the highest affinity, since saturation with either required 2 µg hexose/ml. Fluorescence intensity values obtained with individual polysaccharide-FITC conjugates cannot be compared, since the molar ratio of FITC to polysaccharide is likely to differ and cannot be readily calculated.

Comparison of the concentrations of β-glucans required for 50% inhibition of SZP-FITC staining suggested that CR3 had a somewhat higher affinity for SZP than for β-glucan. Neutrophils were incubated at 4° C. with graded concentrations of β-glucans (SZP, laminarin, MP β-glucan, barley β-glucan, and lentinan), α-mannan or dextran for 15 minutes and then stained by addition of 1.0 mg/ml of SZP-FITC and incubated for an additional 15 minutes at 4° C. Percentage inhibition was then compared with polysaccharide concentration. Whereas 50% of inhibition of SZP-FITC staining required 0.2 µg of hexose/ml of unlabeled SZP, 50% inhibition of SZP-FITC by unlabeled β-glucans required 5 mg of hexose/ml (MP β-glucan or laminarin) to 75 ug hexose/ml (lentinan). Similar results were obtained when the same unlabeled polysaccharides were examined for inhibition of laminarin β-glucan-FITC staining. The rank order for inhibiting activity for both experiments was SZP>laminarin>MP β-glucan. However, CM β-glucan (carboxymethyl β-glucan from yeast), barley β-glucan, and lentinan inhibited laminarin-FITC staining more efficiently than they inhibited SZP-FITC staining. Overall, these results demonstrate that barley β-glucan has a relatively low affinity for CR3 than did soluble yeast MP β-glucan or SZP.

Figures 11A, 11B:
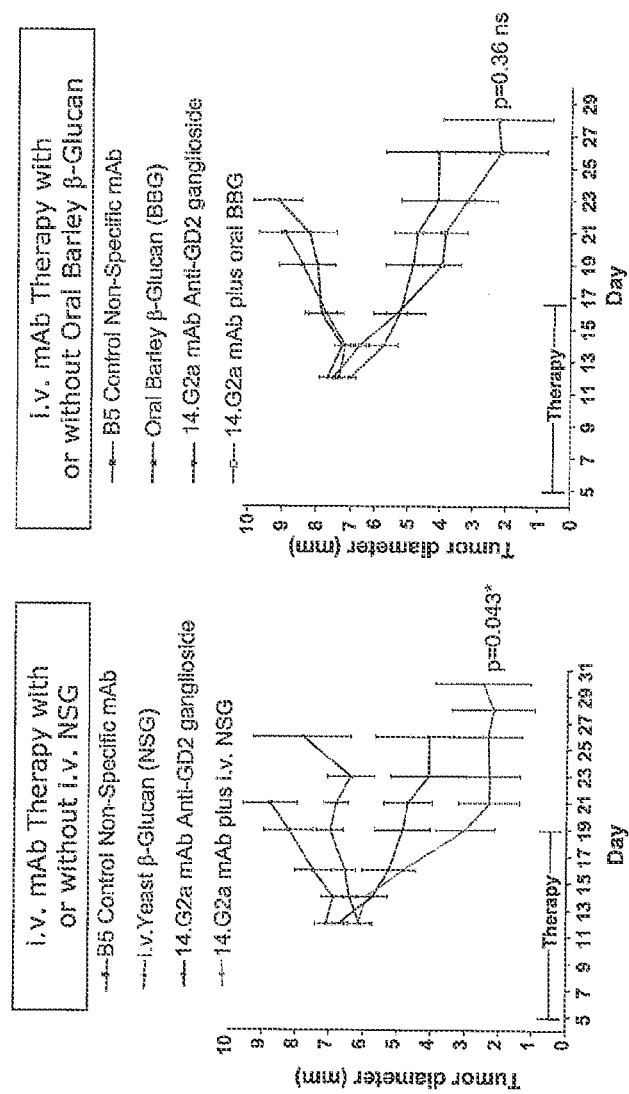
FIGS. 11A and 11B are graphs comparing mAb therapy of RMA-S lymphoma with i.v. soluble yeast β-glucan (NSG) (FIG. 11A) vs. oral barley β-glucan (FIG. 11B).

As was seen in Table 1, β-glucan from barley exhibits a lower affinity for CR3 than yeast β-glucan. FIG. 11 compares the antitumor effectiveness of yeast β-glucan with barley β-glucan when used alone or in conjunction with mAb against GD2 ganglioside, a tumor antigen expressed by RMA-S lymphoma. NSG was provided at a dose of 10 mg/Kg, while Barley β-glucan (BBG) was provided at a dose of 60 mg/Kg. The results demonstrated that NSG alone was more effective than BBG alone NSG was significantly more effective on a per-weight basis. When administered with mAb, NSG also produced a more rapid suppression of tumor weight, reducing tumor down to 2 mm diameter 5 days earlier than BBG. Visual inspection of mice treated with anti-GD2 mAb plus NSG 3-glucan also revealed dramatic differences between control mice receiving B5 non-specific mAb. Whereas the control mice developed large and necrotic tumors which were uniformly fatal, mice treated with mAb along with NSG showed only a very small or no tumor, and 50% were long-term survivors. Taken together, these results show a clear superiority of NSG relative to BBG.

Figure 12:
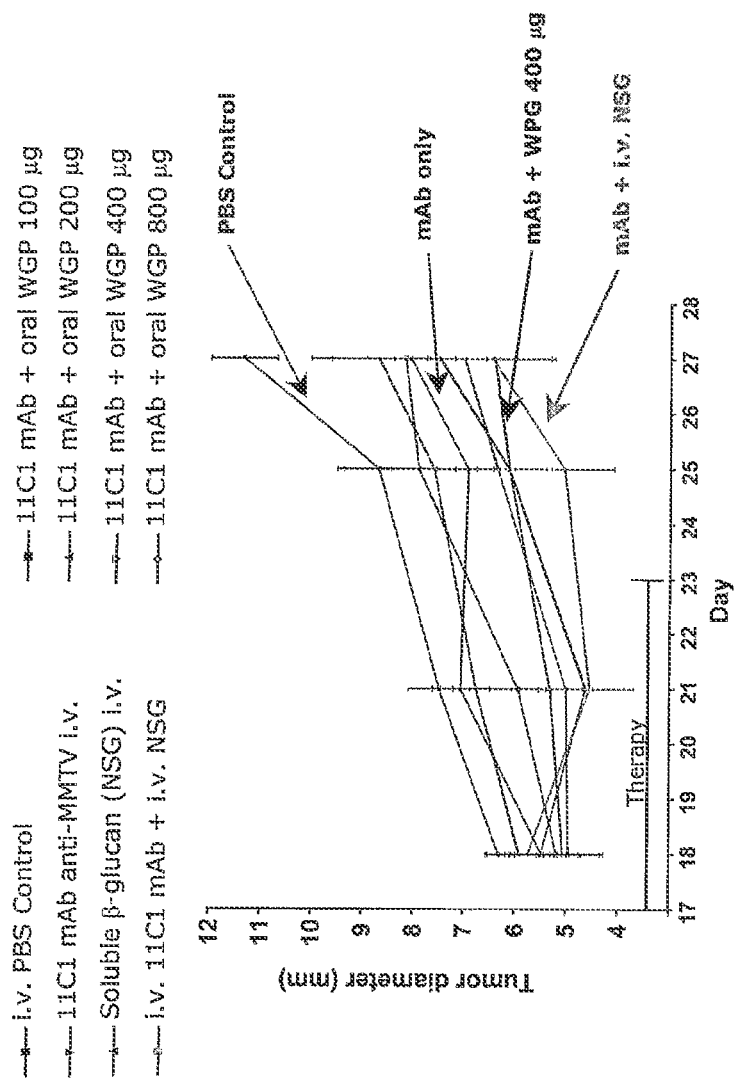
FIG. 12 is a graph showing the results of therapy of Balb/c mammary carcinoma with i.v. mAb plus oral yeast β-glucan particles (WGP).

Balb/c mammary carcinoma was then treated with i.v. mAb and oral WGP at various concentrations or i.v. NSG to determine the relative in vivo activity of these combinations, as shown in FIG. 12. This demonstrated the effectiveness of both the NSG and WPG forms of β-glucan, as well as the oral and intravenous administration routes. The NSG and WPG forms demonstrated comparable effectiveness, with 400 µg of oral WGP providing the strongest activity relative to other doses of WGP. Visual inspection of mice again confirmed these results. Mice in the control group receiving i.v. mAb 11C1 only showed tumors of about 9 mm in diameter. In mice receiving i.v. mAb 11C1 plus i.v. soluble β-glucan (NSG), 4 out of 5 mice showed no visible tumor. In mice receiving i.v. mAb 11C1 plus oral WPG at 200 µg/day, tumors were 20% the size of controls, and 2 out of 5 mice had only barely visible tumors.

Figure 13:
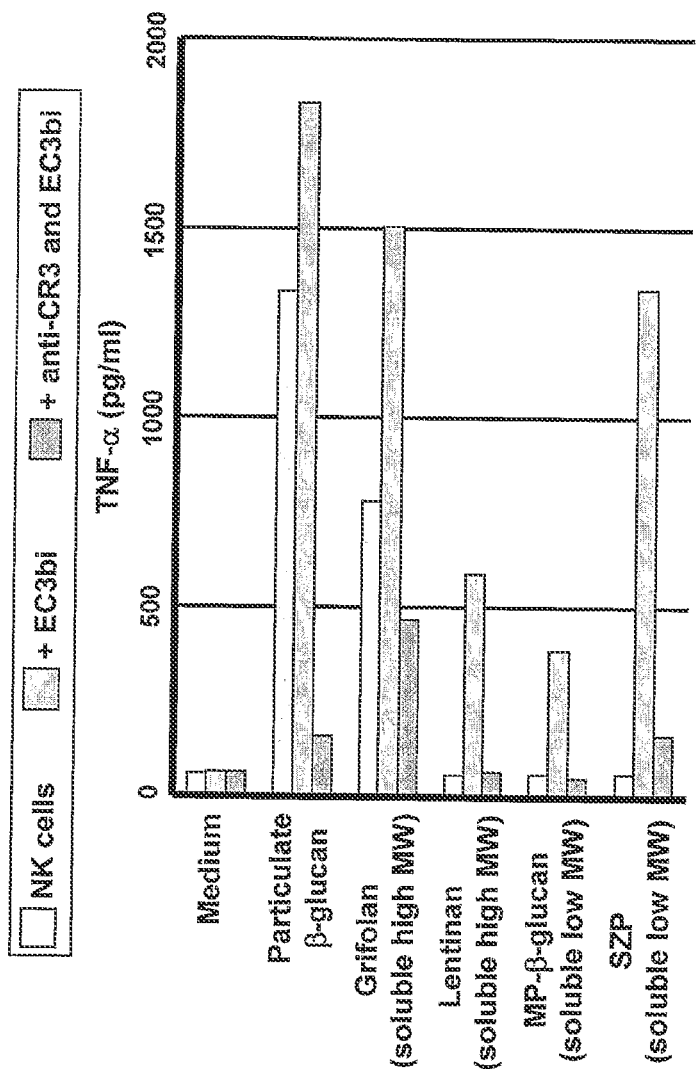
FIG. 13 is a graph showing β-glucan and CR3-dependent stimulation of NK cell secretion of TNF-α

The function of NK cells in mediating host defense includes both direct cytotoxicity of tumor cells and the secretion of cytokines such as TNF-α and IFN-γ that can potentially regulate immune responses and recruit tumoricidal macrophages. Although direct cytotoxicity of tumors by NK cells has been shown to be mediated by the activation of CR3, additional studies have shown that this same CR3 activation event might also trigger cytokine secretion. Experiments were conducted to confirm this point, the results of which are shown in FIG. 13. This figure shows β-glucan CR3-dependent stimulation of TNF-α secretion by NK cells. Human NK cells were cultured with either particulate yeast β-glucan or soluble CR3-binding polysaccharides for 18 hours at 37° C. Culture supernatants were then analyzed for TNF-α by ELISA. Particulate yeast β-glucan (2 g/ml) and grifolan (500 kDa soluble β-glucan from *Grifola Frondosa*, 2 g/ml) are able to bind and crosslink the lectin sites of surface CR3 molecules, causing cellular activation and the secretion of both TNF-α and IL-6 (not shown). By contrast, the small (20 kDa) soluble yeast β-glucan (MP β-glucan; 2.0 µg/ml) and SZP (soluble zymosan polysaccharide preparation containing β-oligomannan and/or β-glucan; 2.0 µg/ml) bind only to individual CR3 molecules and do not trigger cytokine release in the absence of target cells. As with NK cell CR3-dependent cytotoxicity, binding of small β-glucans to CR3 resulted in receptor priming for subsequent cytokine release triggered by ligation to an iC3b-opsonized target cell (sheep erythrocytes opsonized with iC3b—"+EC3b"). The EC3bi targets did not trigger NK cell cytokine release in the absence of such polysaccharide priming, as shown in the medium control. After polysaccharide priming of CR3, ligation to an iC3b-target cell resulted in secretion of TNF-α, IFN-γ, IFN-α, and IL-6. Addition of 5 mg/ml of an anti-CD11b mAb (OKM1) blocked the secretion of all four cytokines from NK cells. Anti-CR3 blocks both β-glucan binding to CR3, as well as the binding of primed CR3 to iC3b on the EC3bi target cells.

The results shown in FIG. 3 show that NK cell secretion of cytokines occurred in parallel to CR3 activation for cytotoxicity. Particulate β-glucan, that triggers a vigorous CR3-dependent neutrophil superoxide burst, likewise triggered NK cell CR3-dependent release of cytokines. Cytokine secretion did not occur with the initial CR3 priming step that occurs with the binding of small soluble β-glucans to CR3, and occurred only secondarily with the CR3 activation step triggered by cross-linking of the β-glucan primed CR3 to an iC3b-opsonized target cell. Incubation of NK cells with EC3bi in medium alone, that does not stimulate NK cell lysis of the EC3bi, also did not trigger cytokine secretion. However, when EC3bi was added after priming of NK cell CR3 with soluble (or particulate) β-glucan, then the secretion of TNF-α, IFN-α, IFN-γ, and IL-6 was detected by ELISA. Such cytokine release was CR3-dependent because it was blocked when an anti-CD121b mAb was added at the same time as the target EC3bi.

This data suggests a further explanation for the successful use of β-glucans in cancer immunotherapy. In addition to the cytotoxicity triggered when a β-glucan primed NK cell enters a tumor opsonized with iC3b, the same localized cytotoxicity stimulated by the iC3b-opsonized tumor cells would be accompanied by a local, rather than systemic, release of cytokines. This localized release of cytokines within tumors may be responsible for the adjuvant effect of β-glucans in promoting recognition of cellular antigens by T cells. While not intending to be bound by theory, this could also explain the synergistic effect of administration of NSG and WGP which may stimulate different aspects of immune cell behavior. As noted earlier, larger β-glucans are required to cause crosslinking and subsequent cytokine release, whereas smaller β-glucans are more effective at activating cell mediated cytotoxicity via CR3 binding. Synergistic results are often obtained when two different systems are effected simultaneously, as is the case here, whereas additive results are more commonly the result when two agents simply act on the same system.

Figure 14:
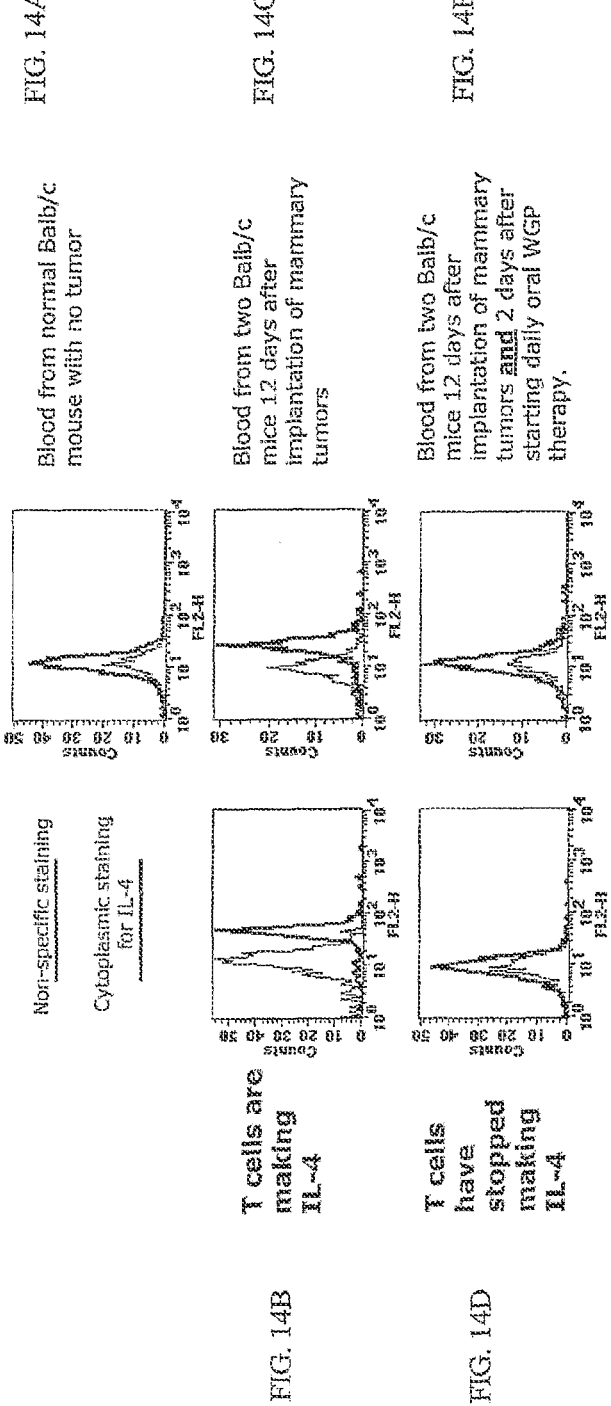
FIGS. 14A-14E are a series of graphs showing that oral WGP therapy of mice with mammary carcinoma converts a tumor-elicited Th2 response into a Th1 response.

Another important aspect of the present invention is the ability of oral β(1,3)-glucan therapy using WPG to induce a Th2 to Th1 shift in the acquired immune system response. FIG. 14 demonstrates this, showing that oral WGP therapy of mice with mammary carcinoma converts a tumor-elicited Th2 response into a Th1 response. The Th1 and Th2 subsets of helper cells release different cytokines when stimulated, with Th1 releasing IL-2, IFN-γ, and TNF, while Th2 releases IL-4, IL-5, and IL-10. IL-2 is a growth factor for Th1 cells, while IL-4 is a growth factor for Th2 cells. The first part of FIG. 14 shows cells in their natural state, when not activated by a tumor. Here, fluorescent staining demonstrates an absence of CD4$^+$ T cells with cytoplasmic IL-4. Mice were then implanted with mammary tumors, and blood samples were taken 12 days after implantation. Blood from these mice showed the presence of T cells making IL-4, indicating the presence of a Th2 immune response. Mice were then administered oral WGP, and after 2 days, another blood sample was taken. This blood sample revealed the disappearance of IL-4, indicating a shift away from Th2 towards a Th1 immune response. The shift to the Th1 response against the tumor leads to an enhanced anti-tumor response by the acquired immune system, as tumor cells are refractive to complement-mediated cytotoxicity but susceptible to the cytotoxic killer T-cell response.

Example 2

Materials and Methods

Antibodies and Other Reagents.

The hybridoma producing 11C1 IgG2a anti-MMTV (Raychaudhuri, S., et. al., *J. Immunol.*, 137: 1743-1749 (1986)) was generously provided by Dr. Hiroshi Fugi (Department of Molecular Immunology, Roswell Park Cancer Institute, Buffalo, N.Y.). The 3F8 IgG3 anti-$G_{D2}$ ganglioside mAb (Saito, M., Yu, R. K., and Cheung, N.-K. V., *Biochem. Biophys. Res. Commun.*, 127: 1-7, 1985; Cheung, N.-K. V., *J. Nucl. Med.*, 28: 1577-1583 (1987), purified and in sterile citrate-buffered saline, was generously provided by Dr. Nai-Kong V. Cheung (Memorial Sloan-Kettering Cancer Center, New York, N.Y.). Purified 14.G2a IgG2a anti-$G_{D2}$ mAb (Hank, J. A., et al., *Cancer Res.*, 50: 5234-5239, 1990; Uttenreuther-Fischer, M. M., Huang et al., *Cancer Immunol. Immunother.*, 41: 29-36, 1995.), as well as the hybridoma, was generously provided by Dr. Ralph A. Reisfeld (Research Institute of Scripps Clinic, La Jolla, Calif.). The BCP8 hybridoma producing IgG2b anti-human MUC1 mAb (Xing, P. X., et al., *Cancer Res.*, 52: 2310-2317 (1992) was kindly provided by Dr. Ian F. C. McKenzie (Austin Research Institute, Heidleberg, Australia). The hybridoma producing the rat anti-mouse granulocyte mAb RB6-8C5 (Ly-6G; anti-Gr-1) (Hestdal, K., et al., *J. Immunol.*, 147: 22-28, (1991) was kindly provided by Dr. Emil Unanue (Washington University School of Medicine, St. Louis, Mo.). The B5 hybridoma secreting mouse IgG2a mAb specific for the human high molecular weight melanoma antigen was obtained from the ATCC (Manassas, Va.) and the isolated IgG was used as a "non-specific" mAb control for mouse tumor therapy protocols. Each hybridoma was adapted to grow in 1-2% FCS and BD Hybridoma medium, and then grown in bioreactor flasks (BD Biosciences, San Jose, Calif.) to generate a spent medium rich in mAb that was subsequently purified using sequential steps of ammonium sulfate precipitation, Mono-Q FPLC chromatography, and Mono-S FPLC chromatography (28). Purified mAbs were sterilized by ultrafiltration and any detectable LPS was removed by extraction with Triton X-114 (Aida, Y. and Pabst, M. J., et al., *J. Immunol. Methods*, 132: 191-195 (1990)).

Goat anti-mouse antibodies to IgM, IgG, and C3 labeled with fluorescein isothiocyanate (FITC) were purchased from ICN Biomedicals/Cappell (Aurora, Calif.) and used for analysis of Ig and C3 opsonization of tumor cell suspensions using flow cytometry (BD FACScan, BD Biosciences Immunocytometry Systems, San Jose, Calif.). Anti-mouse CD45-PerCP-Cy5.5, anti-mouse CD80-FITC, and anti-Gr-1-PE, anti-mouse CD11c-FITC, as well as appropriately labeled isotype controls, were purchased from BD Biosciences Phamingen. Rat anti-mouse F4/80-FITC and an isotype control were obtained from Caltag Laboratories (Burlingame, Calif.).

Therapeutic β-glucans

A preparation of soluble β-glucan known as "soluble zymosan polysaccharide" (SZP) that was ~6 kD in size was generated from zymosan by formic acid extraction followed by Mono-Q FPLC as previously described (Xia, Y., et al., *J. Immunol.*, 162: 2281-2290 (1999), Thornton, B. P., et al., *J. Immunol.*, 156: 1235-1246(1996)). SZP was used for tumor immunotherapy where indicated in figure legends. For the remaining protocols, a soluble β-glucan known as NSG™ β-glucan (neutral soluble glucan) that was estimated to be ~10 kD in size was obtained from Biopolymer Engineering, Inc., Eagan, Minn. NSG was derived from baker's yeast and came from a batch of material that had been generated several years ago by Alpha Beta Technology, Inc. (Worcester, Mass.), and is similar to the product that they had marketed as soluble yeast β-glucan through Molecular Probes, Inc. (Eugene, Oreg.) approximately 7 years ago. The ability of this latter material to bind to and prime human and murine CR3 for toxicity of iC3b-opsonized tumor cells was described in previous publications (Vetvicka, V. et al., *J. Clin. Invest.*, 98: 50-61 (1996), Xia, Y., et al., *J. Immunol.*, 162: 2281-2290 (1999) Thornton, B. P., et al., *J. Immunol.*, 156: 1235-1246(1996)).

Mice and Tumor Models

Normal BALB/c and C57Bl/6 mice were purchased from the Jackson Laboratory (Bar Harbor, Me.) or NCI-Frederick (Frederick, Md.). Heterozygous C3-deficient (C3$^{+/-}$) mice (31) were purchased from The Jackson Laboratory and used to establish a breeding colony from which were derived both homozygous deficient (C3$^{-/-}$) and their wild-type (C3$^{+/+}$) C57Bl/6 littermates. A breeding colony of C57Bl/6 CR3-deficient (CD11b$^{-/-}$) mice (Coxon, A., Rieu, et al., *Immunity*, 5: 653-666, 1996) and their wild-type (CD11b$^{+/+}$) C57Bl/6 littermates was obtained from Dr. Tanya Mayadas-Norton (Brigham & Women's Hospital and Harvard Medical School, Boston, Mass.). The phenotypes of the C3$^{-/-}$ and CR3$^{-/-}$ mice and their littermates were confirmed by assays for serum C3 using quantitative radial immunodiffusion and for blood neutrophil CD11b expression using immunofluorescence staining and flow cytometry analysis, respectively.

The BALB/c mammary carcinoma known as Ptas64 (or 64PT) was obtained from Dr. Wei-Zen Wei (Karmonos Cancer Center and Wayne State University, Detroit, Mich.). This tumor line expresses a MMTV (murine mammary tumor virus) membrane antigen detectable with the 11C1 mAb. Previous studies showed that normal BALB/c serum contained naturally-occurring antibodies reactive with Ptas64 that opsonized the tumor cells growing in vivo with IgM, IgG, and C3, and that additional i.v. injections of 11C1 mAb produced increased surface uptake of IgG and C3 (Yan, J., et al., *J. Immunol.*, 163: 3045-3052 (1999). Four groups of 6-8 mice were injected s.c. with 0.5 to $1.0 \times 10^6$ cells in a mammary fat pad and a tumor was allowed to form over a 7 to 10 day period. When tumor diameters reached 3-4 mm as measured by calipers as an average across the tumor length and width, therapy was initiated. The four groups included: 1) control group receiving i.v. PBS or i.v. non-specific mAb; 2) 100 µl 11C1 mAb in saline (2 mg/ml) i.v. every 3rd day; 3) 100 µl β-glucan (NSG, 3 mg/ml) i.v. daily; and 4) a combination 11C1 mAb every $3^{rd}$ day and daily injections of β-glucan. Tumor diameter was measured every 3rd day, and mice were sacrificed when tumor diameters reached 15 mm.

The C57B1/6 lymphoma EL-4, that highly expresses membrane $G_{D2}$ ganglioside, was provided by Dr. Nai-Kong V. Cheung. Normal C57B1/6 mice were injected with $3 \times 10^5$ EL-4 cells i.v. to generate liver tumors (Zhang, H., et al., *Cancer Res.*, 58: 2844-2849 (1998)). Ten days later, 4 groups of 6 mice were given i.v. 100 µl doses of: a) PBS (control group), b) SZP β-glucan (4 mg/ml) repeated daily, c) 3F8 mAb to $G_{D2}$ ganglioside (2 mg/ml) repeated every $3^{rd}$ day, or d) both daily β-glucan and 3F8 mAb every $3^{rd}$ day. After 2 weeks of therapy, the mice were sacrificed and their livers were removed and weighed in comparison to the livers of a group of normal tumor-free mice. The net weight of liver tumors was calculated by subtracting the weight of a normal liver (1.0 g) from the weights of the livers from tumor-bearing mice. A similar liver tumor model was carried out using the C57B1/6 lymphoma RMA-S that similarly expresses $G_{D2}$ ganglioside but is defective in peptide loading of MHC class I (kindly provided by Dr. Olivera J. Finn, Pittsburgh Cancer Institute, Pittsburgh, Pa.) in combination with 14.G2a mAb to $G_{D2}$ ganglioside (100 µg, given i.v. every $3^{rd}$ day). Mice were similarly divided into 4 groups that were treated beginning 5 days after i.v. injection of $3 \times 10^5$ cells with: 1) i.v. PBS (control), 2) i.v. NSG β-glucan (400 µg per day), 3) 14.G2a mAb, or 4) both NSG β-glucan and 14.G2a mAb. Therapy was continued for a period of 3 weeks and the mice were then observed for long-term tumor-free survival.

RMA-S cells transfected with human MUC1 were also provided by Dr. Finn (Soares, M. M., et al., *J. Immunol.*, 166: 6555-6563 (2001)), and $1 \times 10^6$ cell were implanted s.c. in C57B1/6 mice in or near a mammary fat pad. After 8-10 days when tumors of 3-4 mm appeared, therapy was initiated with either 14.G2a anti-$G_{D2}$ or BCP8 anti-MUC1 mAb, with or without NSG β-glucan using 4 groups of mice: a) 200 µg of B5 non-specific control mAb given i.v. every $3^{rd}$ day; b) 400 µg of NSG β-glucan given i.v. daily; c) 100 µg of 14.G2a anti-$G_{D2}$ mAb or 200 µg of BCP8 anti-MUC1 mAb given i.v. every $3^{rd}$ day; d) combined treatment with both mAb and β-glucan. Therapy was continued for 2 or 3 weeks (as indicated), with tumor measurements made as before, and mice were sacrificed if tumors reached 15 mm in diameter. Mice were observed for tumor-free survival over a total period 90-120 days.

Lewis lung carcinoma cells (LL/2, CRL-1642) originally derived from C57B1/6 mice were obtained from the ATCC and transfected with a plasmid containing cDNA for human MUC1 that was provided by Dr. Olivera Finn (Soares, M. M., et al., *J. Immunol.*, 166: 6555-6563, 2001.). A LL/2 line expressing a uniformly high surface density of MUC1 was selected by FACS sorting of cells stained with BCP8-FITC mAb (MoFlo High Speed Cell Sorter, Dako-Cytomation, Fort Collins, Colo.). A further selection was made by passaging the cell line two times in C57B1/6 mice given the cells s.c. A tumor line was selected that both expressed uniformly high levels of surface MUC1 and was capable of generating s.c. tumors in C57B1/6 injected with as few as $5 \times 10^5$ cells. Therapy of mice bearing these s.c. tumors was initiated after 7 days when tumors were only 1-2 mm in diameter. Four groups of six C3-deficient or their wild-type littermate C57B1/6 mice were treated with: a) i.v. PBS every $3^{rd}$ day (control); b) 400 µg of NSG β-glucan given i.v. daily; c) 200 µg of BCP8 anti-MUC1 mAb given i.v. every $3^{rd}$ day; d) combined therapy with BCP8 mAb and NSG β-glucan. Therapy was given for 3 weeks with measurement of tumor diameters every $3^{rd}$ day, and mice were sacrificed when tumors reached 15 mm diameter. Mice were observed over a total period of 90 days for tumor-free survival.

Analysis of Mice with Mammary Tumors for Leukocytosis

Two groups of 6 BALB/c mice were compared for peripheral blood leukocyte counts following mammary fat pad implantation of $1 \times 10^6$ Ptas64 mammary adenocarcinoma cells in one of the groups of mice. After tumors appeared on day 8, peripheral blood was collected every other day for analysis. Absolute leukocyte counts were performed using BD Tru-Count tubes (BD Biosciences, San Jose, Calif.) according to the instructions from the manufacturer. Briefly, 50 µl of whole blood was stained in Tru-Count tubes containing a known number of beads with 1.0 µl of PerCP-Cy5.5-conjugated rat anti-mouse CD45 mAb. After 20 min on ice, erythrocytes were lysed by adding 450 µl of FACS Lysing Solution (BD Biosciences, San Jose, Calif.) and samples were immediately analyzed by BD FACScan. During data acquisition, a threshold of FL-3 was established that allowed analysis of beads and CD45$^+$ cells only. Absolute leukocyte counts were calculated according to the formula:

$$\frac{\text{\# of events in region containing leukocytes}}{\text{\# of events in absolute count bead region}} \times \frac{\text{\# beads per test}}{\text{test volume}} =$$

Absolute Count of leukocytes

Tumor Therapy with Granulocyte-Depleted Mice

The Ptas64 mammary tumor model in BALB/c mice was carried out as above with some therapy groups added in which the mice were depleted of granulocytes using a previously reported method that involves treatment with the rat anti-mouse granulocyte mAb RB6-8C5, also known as anti-Gr-1 (Wipke, B. T. and Allen, P. M., *J. Immunol.*, 167: 1601-1608 (2001)). To prevent infections in the granulocyte-depleted mice, all therapy groups of the mice were maintained in laminar flow hoods and tetracycline antibiotic was added to their drinking water (500 mg tetracycline and 50 g sucrose per liter of water). Because effective tumor regression requires serum complement to opsonize tumors with iC3b, pilot studies were carried out to determine conditions of chronic granulocyte depletion that would give time for repletion of serum complement function prior to initiating tumor therapy. Mice were injected with 300 g of RB6-8C5 mAb i.p. 3 days prior to beginning therapeutic treatment of the tumors with 11C1 mAb and NSG β-glucan. After the initial depletion of granulocytes, additional i.v. injections of 300 μg of RB6-8C5 were given at 3-day intervals by mixing together the RB6-8C5 mAb with the 11C1 mAb so that both mAbs were given in a single i.v. injection at the same time. Tests of sera from mice treated with the RB6-8C5 showed that complement activity had returned to normal levels by day 3, whereas peripheral blood smears stained with Wright-Giemsa showed virtually no remaining neutrophils or eosinophils. Continued i.v. injections of RB6-8C5 did not affect serum complement levels significantly because granulocyte numbers were too low to require significant complement consumption for cytotoxicity. There was also no evidence for depletion of complement during the tumor therapy period by tests of sera from RB6-8C5-treated mice for their ability to opsonize 11C1-opsonized Ptas64 tumor cells with C3 in vitro as determined by staining with anti-C3-FITC and flow cytometry. To confirm that the RB6-8C5 mAb depleted only granulocytes that express high surface levels of Gr-1 and not monocytes, macrophages, and dendritic cells that express lower surface densities of Gr-1, additional tests were carried out on mice undergoing the RB6-8C5 depletion protocol to check for the presence and number of these other myeloid cell types in bone marrow, spleen, and peripheral blood. Monocytes were identified in blood samples using flow cytometry and double-staining with anti-Gr-1-PE and anti-CD80-FITC, macrophages were identified with anti-Gr-1-PE and F4/80-FITC, and dendritic cells were identified with anti-Gr-1-PE and anti-CD11c-FITC.

Graphing and Statistical Analysis of Data.

All data from mouse tumor therapy protocols was entered into Prism 3.0 (Graph Pad Software, San Diego, Calif.) to generate graphs of tumor regression or survival. Student's T test was next employed within Prism 3.0 to determine the significance of different data sets.

Results

Therapy with β-Glucan Requires Anti-Tumor Antibody.

Figure 15:
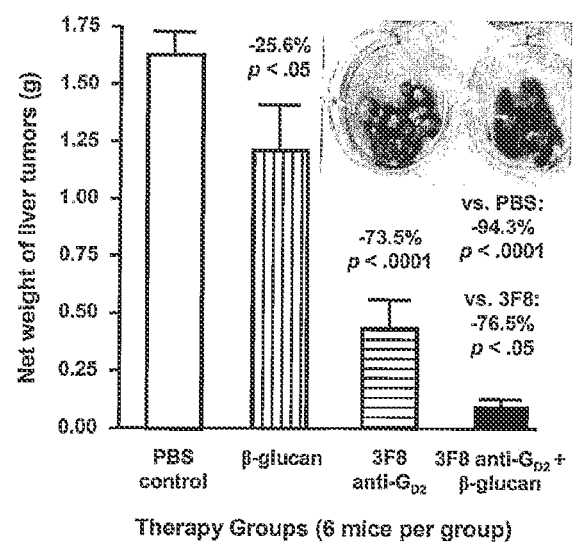
FIG. 15 is a graph showing β-glucan enhances regression of EL-4 hepatic lymphoma when combined with 3F8 IgG3 anti-$G_{D2}$ ganglioside mAb. As described in the Materials and Methods Section herein, mice were injected with EL-4 cells i.v. to generate liver tumors and after ten days were treated with mAb and/or β-glucan. After 2 weeks of therapy, the mice were sacrificed and the livers were removed and weighed in comparison to the livers of normal tumor-free mice. The mean values±SD are shown.

Previous research had shown that the therapeutic effect of β-glucans required the presence of naturally-occurring anti-tumor antibodies that functioned to target the tumor cells with iC3b (28). It was hypothesized that EL-4 lymphoma was resistant to β-glucan therapy (Takahashi, K., et al., *J. Pharmacobiodyn.*, 11: 472-478, 1988, Kano, Y., et al., *Biotherapy*, 9: 241-247 (1996)) because serum from the syngeneic C57B1/6 host lacked detectable naturally-occurring antibodies reactive with EL-4 (28). When injected i.v., EL-4 forms hepatic tumors (FIG. 15). Analysis of isolated hepatic tumor cells 2 weeks after implantation demonstrated little or no surface staining for IgM, IgG, or C3 detectable by flow cytometry (data not shown). Treatment of mice with i.v. β-glucan alone produced only a 25.6% reduction in liver tumor net weight (FIG. 15). EL-4 cells express a high surface density of $G_{D2}$ ganglioside that can be targeted with the IgG3 mAb 3F8 that both activates complement and mediates significant ADCC (Zhang, H., et al., *Cancer Res.*, 58: 2844-2849 (1998)). With a small tumor burden and early mAb administration (≤3 days after tumor implantation), 3F8 therapy completely eradicates liver tumors (Zhang, H., et al., *Cancer Res.*, 58: 2844-2849 (1998)). However, when 3F8 was given over a 2-week period starting 10 days after tumor implantation, tumors were not eradicated, although there was a 73.5% reduction in net tumor weight (FIG. 15). Flow cytometry analysis of tumor cells from mice treated with 3F8 exhibited abundant staining for both IgG and C3 (not shown). Finally, the co-administration of both i.v. 3F8 and β-glucan resulted in a 94.3% reduction in tumor weight compared to untreated controls and a 76.5% reduction in tumor weight as compared to mice receiving the 3F8 mAb only.

Figure 16:
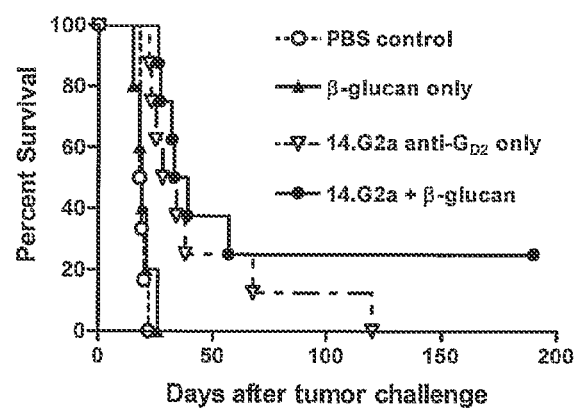
FIG. 16 is a graph showing enhanced survival of mice with RMA-S hepatic lymphomas treated with 14.G2a IgG2a anti-$G_{D2}$ ganglioside in combination with β-glucan. As described in the Materials and Methods Section, mice were injected with RMA-S tumor cells i.v. to generate tumors in the liver and after five days later were given i.v. therapy with mAb and/or β-glucan. Therapy was administered for 3 weeks and then the survival of mice was recorded.

Tumor-free survival was examined in a similar liver tumor model incorporating the RMA-S lymphoma, the C57B1/6 syngeneic host, and the 14.G2a IgG2a mAb to $G_{D2}$ ganglioside (FIG. 16). Unlike EL-4, the RMA-S tumor is defective in its ability to load peptides in MHC class I and therefore resistant to recognition and killing by cytotoxic T lymphocytes (CTL). Therapy with β-glucan alone had no therapeutic benefit, whereas therapy with 14.G2a alone did extend survival. However, combined therapy with both 14.G2a and β-glucan not only extended survival but also 25% of mice were long-term survivors.

Combined Therapy with β-Glucan Significantly Enhances Tumor Regression and Survival Elicited with MAb Alone.

Figure 17A:
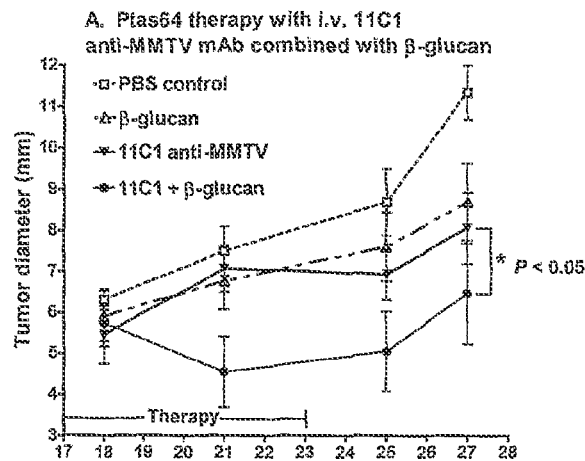
FIGS. 17A-17C are a series of graphs showing combined use of yeast β-glucan significantly enhances the regression of mammary or s.c. tumors produced by treatment with anti-tumor mAb alone. Three different tumor therapy protocols are shown.
Figure 17B:
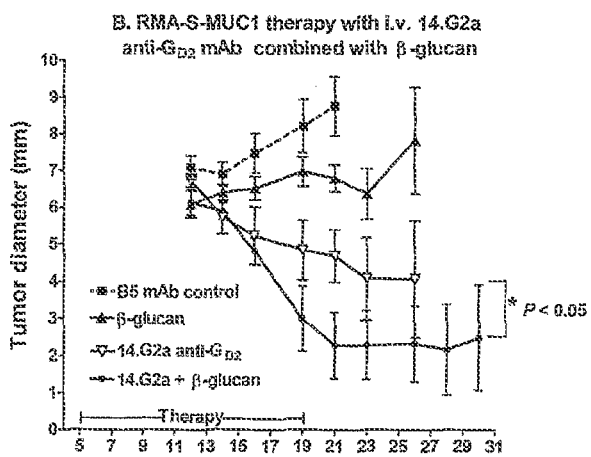
Figure 17C:
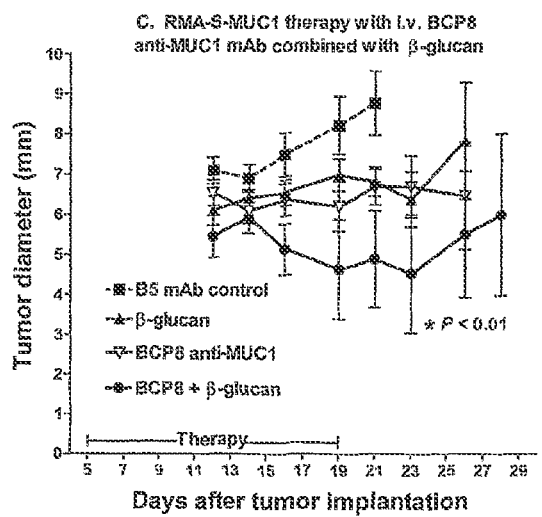

Three mAbs were examined with two mouse tumors, one, Ptas64, a mammary carcinoma in syngeneic BALB/c mice and the other, RMA-S lymphoma transfected with human MUC1 (RMA-S-MUC1) implanted s.c. in C57B1/6 mice (FIG. 17). Ptas64 is latently infected with MMTV and expresses a membrane surface MMTV tumor antigen detectable with the 11C1 IgG2a mAb. Pilot studies demonstrated that a 200 μg i.v. dose of the 11C1 given at 3-day intervals produced a maximal coating of IgG and C3 on individual mammary tumor cells following surgical removal of tumors and flow cytometry analysis (not shown). The RMA-S-MUC1 cells express a high surface density of $G_{D2}$ ganglioside but are much more resistant to CDC than are EL-4 cells (not shown). Pilot studies with 14.G2a demonstrated maximal IgG and C3 uptake by s.c. tumors with a dose of 100 μg of mAb given at 3-day intervals (not shown). Transfection of the RMA-S cells with human MUC1 allowed them to be alternatively targeted with BCP8 IgG2b anti-MUC1. A dose of 200 μg of BCP8 given at 3-day intervals was shown to produce a maximal coating of IgG and C3 on s.c. tumors (not shown).

Figure 18A:
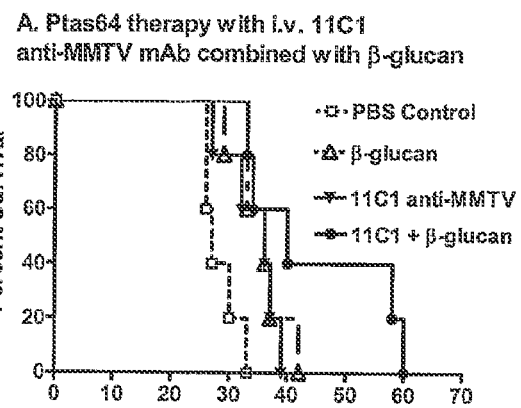
FIGS. 18A-18C are a series of graphs showing combined administration of soluble β-glucan enhances the survival of mice treated with anti-tumor mAbs.
Figure 18B:
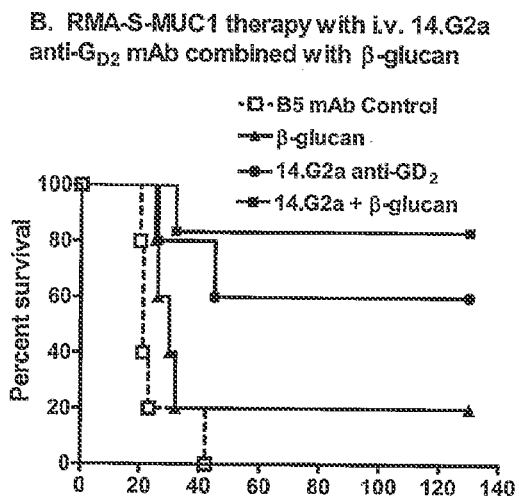
Figure 18C:
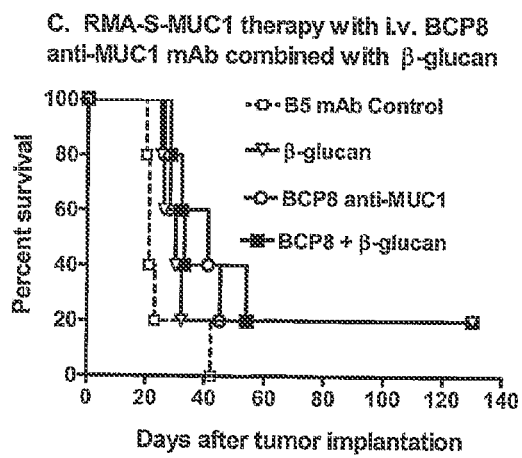

With both Ptas64 (28) and RMA-S (not shown), the syngeneic BALB/c and C57B1/6 host sera contain measurable levels of naturally-occurring anti-tumor antibodies that opsonize solid tumors in vivo with IgM, IgG, and C3. Thus, as expected there was some tumor regression noted when mice with each tumor type were treated with i.v. β-glucan alone (FIG. 17). Likewise, each of the three mAbs had some ability to mediate tumor regression, with the 14.G2a being most effective, probably because of the high $G_{D2}$ antigen density of RMA-S cells. When the RMA-S-MUC1 cells were targeted with BCP8 anti-MUC1 instead of 14.G2a, the lower expression of MUC1 antigen was presumably responsible for a lower rate of tumor regression. Notably, the co-administration of β-glucan in all 3 tumor models resulted in significantly more tumor regression than was observed with mAb therapy alone (FIG. 17). At the end of the 2-week therapy period, mice were observed for tumor-free survival for a 4-month period (FIG. 18). Despite enhanced survival in the Ptas64 tumor model, all of the mice succumbed to tumor within 60 days. Analysis of tumors from these mice showed that many tumor cells no longer reacted with the 11C1 mAb and were not targeted with iC3b in vivo. In another series of experiments, the Ptas64 tumor cells were sorted for high MMTV antigen expression three times over a 4 week period to generate a variant line with much higher MMTV expression than the parent cells (not shown). With these cells expressing a high level of MMTV tumor antigen, combined therapy with 11C1 mAb and β-glucan resulted in survival of 40% of the mice for >90 days (not shown).

With the RMA-S-MUC1 tumors treated with 14.G2a anti-$G_{D2}$ with or without β-glucan, 60% of the mice treated with mAb alone survived, whereas 80% of the mice survived that were treated with a combination of mAb plus β-glucan (difference not significant). The greater success of the therapy with this model is probably due to the high and stable expression of the $G_{D2}$ antigen. When the same tumor cells were targeted with BCP8 anti-MUC1, there was no enhancement of survival with the mAb alone, but both the β-glucan and combined mAb plus β-glucan groups exhibited a comparable 20% survival. Examination of the tumors removed from these mice showed that <25% of the tumor cells continued to express MUC1, suggesting that tumor escape had probably occurred because the tumor cells with MUC1 had been killed selectively by the therapy. Prior to implantation, the RMA-S-MUC1 cells had been sorted by FACS and a line had been selected for tumor implantation that uniformly expressed MUC1.

β-Glucan Adjuvant Function Requires Leukocyte CR3 and Serum C3.

Figure 19A:
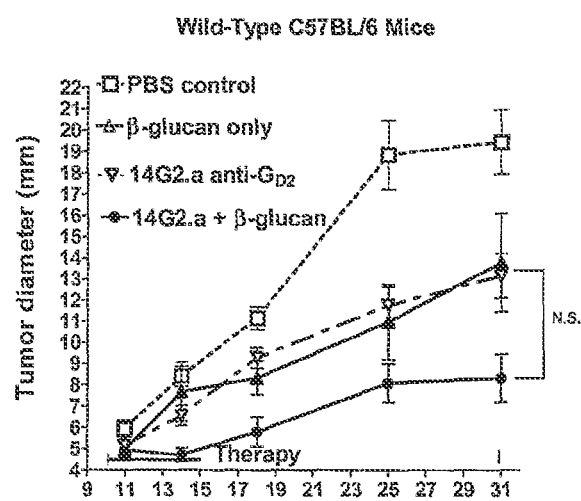
FIGS. 19A-19B are graphs showing the enhancement of tumor regression mediated by NSG β-glucan requires leukocyte CR3 and fails in CR3-deficient (CD11b$^{-/-}$) mice.
Figure 19B:
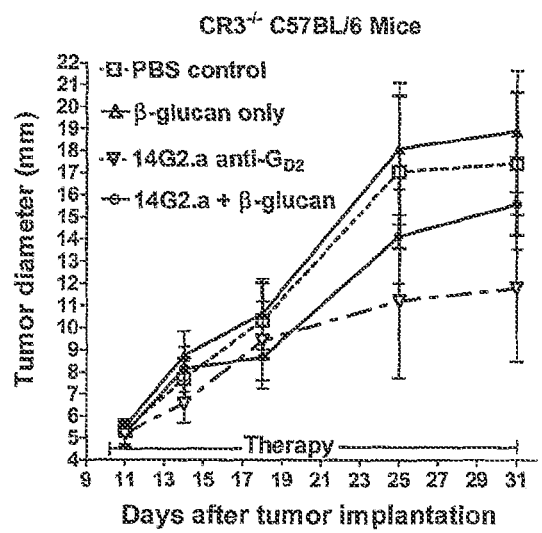
Figure 20A:
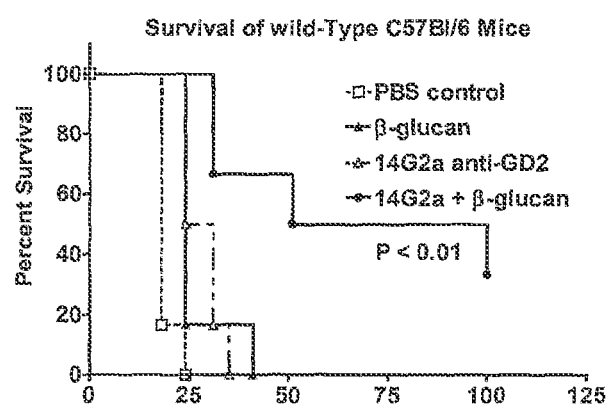
FIGS. 20A-20B are graphs showing NSG β-glucan combined with anti-tumor mAb therapy enhances survival of wild-type (FIG. 20A) but not CR3-deficient mice (FIG. 20B). These data represent the survival curves for the protocol described in FIGS. 19A-19B.
Figure 20B:
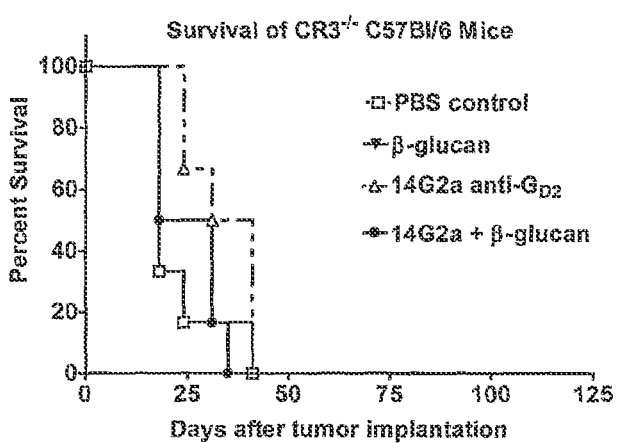

Previous studies had shown that the function of β-glucan alone in tumor regression did not occur in either BALB/c CR3-deficient or 129/J C3-deficient mice (28). The current study examined CR3- or C3-deficient C57Bl/6 mice with RMA-S-MUC1 or LL/2-MUC1 subcutaneous tumors, respectively. With the RMA-S-MUC1 tumors in wild-type mice, regression mediated by either mAb alone or β-glucan alone was comparable, and this was enhanced when mAb was combined with β-glucan (FIG. 19). Although the enhancement of mAb-mediated regression elicited by the use of β-glucan was not significant, the combination of mAb plus β-glucan did produce significantly enhanced survival, with 40% of the mice remaining tumor-free (FIG. 20). In comparison, there were no survivors in the groups treated with mAb alone or β-glucan alone. Finally, in the CR3-deficient mice, there was no regression with β-glucan alone and, although there was good regression with mAb alone, there was no enhancement of mAb regression by combination with β-glucan and none of the therapy groups exhibited long-term survival.

Figure 21A:
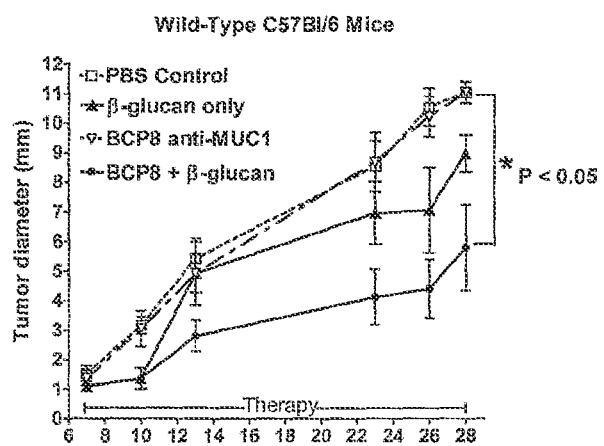
FIGS. 21A-21B are graphs showing the enhanced tumor regression mediated by NSG β-glucan when combined with anti-tumor mAb requires plasma C3 and does not occur in C3-deficient mice.
Figure 21B:
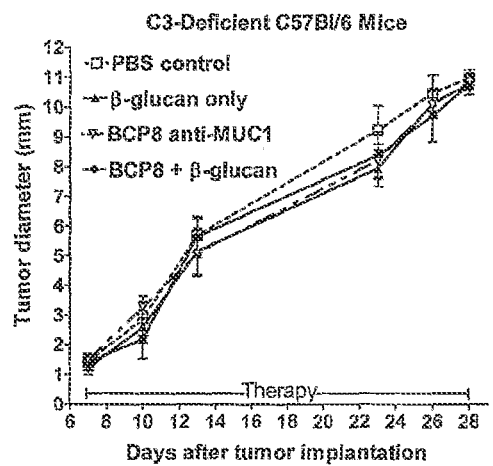
Figure 22A:
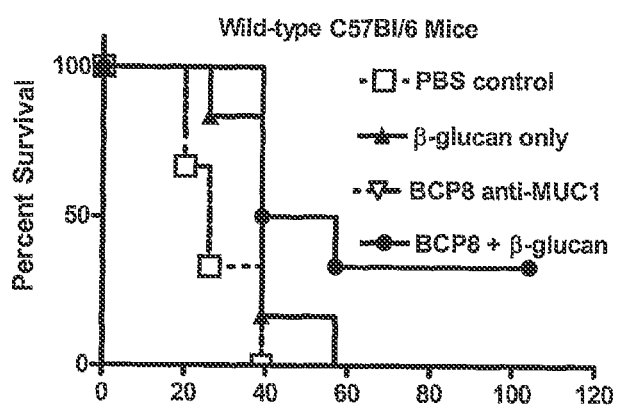
FIGS. 22A-22B are graphs showing the enhanced survival induced by the combination of soluble β-glucan with anti-tumor mAb requires C3 and does not occur in C3-deficient mice.
Figure 22B:
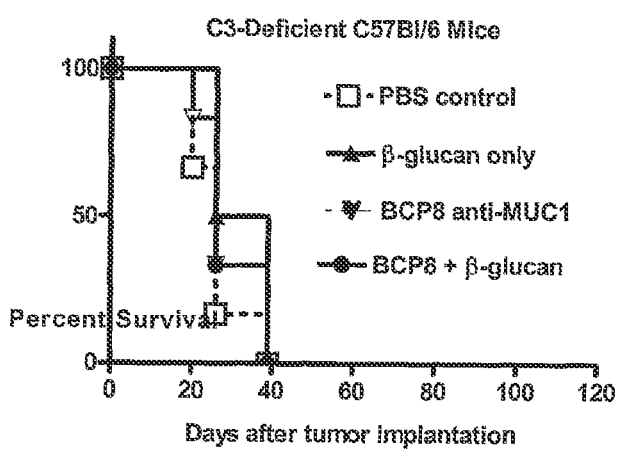

Another tumor model was investigated in wild-type versus C3-deficient C57Bl/6 mice. Lewis lung carcinoma transfected with human MUC1(LL/2-MUC1) was implanted s.c. and treated with BCP8 anti-MUC1 mAb with or without β-glucan. In wild-type mice, there was no tumor regression following treatment with the BCP8 mAb alone, but the regression elicited by combining the BCP8 with β-glucan was significant (P<0.05; FIG. 21). A low level of naturally occurring antibody against the LL/2 tumor cells probably explained the lower level of regression observed in the groups receiving therapy with β-glucan alone. Likewise, both therapy with β-glucan alone or mAb plus β-glucan exhibited a survival advantage compared to mAb alone (FIG. 22). By contrast, neither mAb nor β-glucan, separately or combined, elicited any regression (FIG. 21) or enhanced survival (FIG. 22) in C3-deficient mice.

β-Glucan-Mediated Tumor Regression is Granulocyte Dependent.

Figure 23:
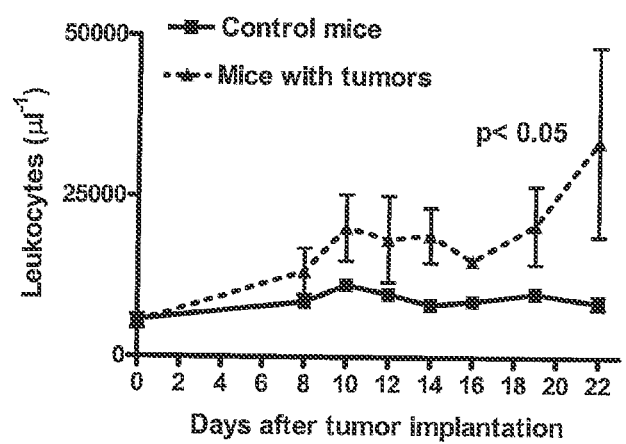
FIG. 23 is a graph showing mammary tumor development elicits significant leukocytosis. Peripheral blood was collected from either BALB/c control mice or mice implanted in a mammary fat pad with 1×10$^6$ Ptas64. Absolute leukocyte counts were performed by flow cytometry as described in the Materials and Methods. Palpable tumors were detected 8 days after implantation. After the 8th day, a significant leukocytosis was observed in tumor-bearing mice whereas control mice had normal leukocyte counts. Mean values±SE of the mean are shown.

Previous in vitro studies had demonstrated that human and mouse monocyte/macrophages, neutrophils, and NK cells could each carry out β-glucan-mediated CR3-dependent cellular cytotoxicity against iC3b-opsonized tumor cells (10, 11, 20). However, attempts to identify the specific effector cell(s) required for this response in mouse tumor models had been unsuccessful. One mechanism that was likely to be involved in the recruitment of leukocytes was complement activation at the tumor site mediated by anti-tumor antibody, and this was recognized to occur in most tumor models via naturally-occurring antibody, even in PBS control group tumors. Indeed, it was shown that there was a significant increase in peripheral blood granulocyte counts (leukocytosis) in mice with Ptas64 mammary tumors that was independent of mAb and/or β-glucan therapy (FIG. 23). Complement activation releases C3a and C5a that function to recruit eosinophils, mast cells (C3a), neutrophils and macrophages (C5a). Thus, recruitment might be equivalent in therapy versus PBS control group tumors, but only in tumors from mice receiving β-glucan would there be leukocytes with primed CR3 able to kill iC3b-opsonized tumor cells.

Figure 24A:
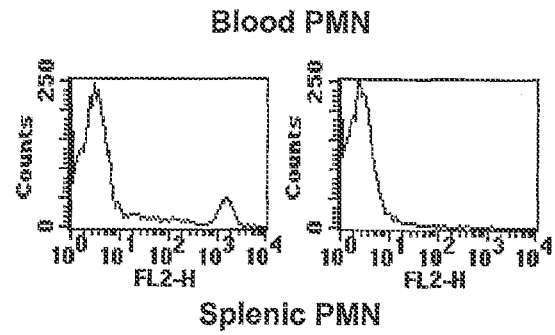
FIGS. 24A-24E are histograms showing treatment of mice with i.v. RB6-8C5 anti-Gr-1 mAb selectively depletes granulocytes but not monocytes, macrophages, or dendritic cells. As described in Materials and Methods, mice were injected with anti-Gr-1 mAb, first by i.p. injection and then 3 days later by i.v. injections repeated at 3-day intervals. Flow cytometry was used to assess the presence of granulocytes (PMN) in blood (FIG. 24A), spleen (FIG. 24B), and bone marrow (FIG. 24B) in normal (left side histograms) versus anti-Gr-1 treated mice (right side histograms). The top two histograms show that anti-Gr-1 treatment effectively removed Gr-1$^+$ PMN from the blood and spleen but had virtually no effect on Gr-1$^+$ PMN in the bone marrow. Monocytes (FIG. 24D) in region 2 (boxed area marked R2) showed no depletion when untreated control mice (left side histogram) were compared to the anti-Gr-1-treated mice (right side histogram). There was also no reduction in splenic macrophage (FIG. 24E) numbers when control mice (left side histogram) were compared to the anti-Gr-1-treated mice (right side histogram). Similar studies carried out with bone marrow macrophages, as well as with splenic and bone marrow dendritic cells likewise provided no evidence for depletion in the anti-Gr-1-treated mice (not shown). For the analysis of each cell population, staining was first carried out with anti-CD45-PerCP-Cy5.5 and a gate for analysis was established that included all CD45$^+$ leukocytes.
Figure 24B:
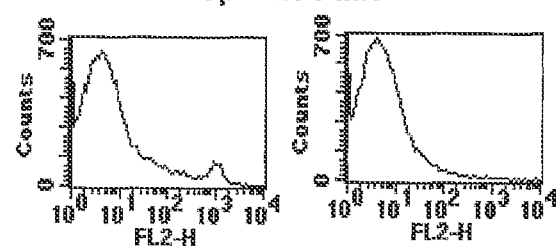
Figure 24C:
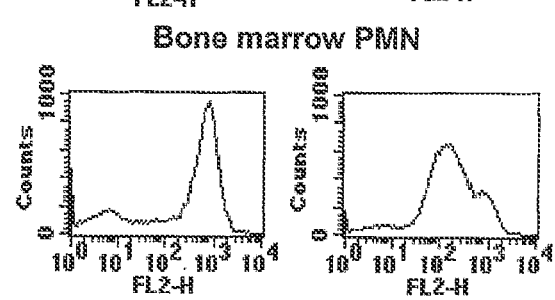
Figure 24D:
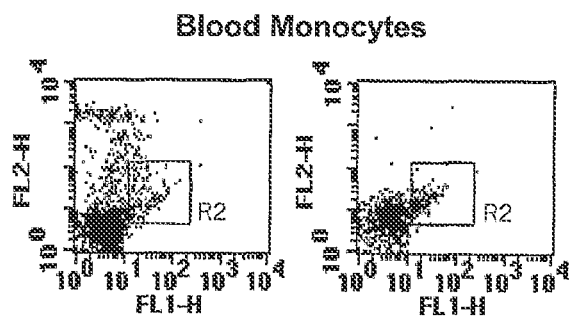
Figure 24E:
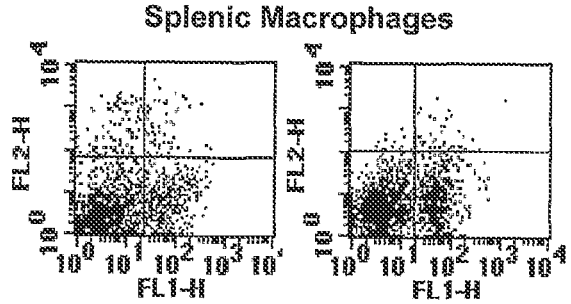

Since the major leukocyte type identified in Ptas64 tumors (with or without therapy) was the granulocyte, it was hypothesized that β-glucan-primed CR3 granulocytes might be predominantly responsible for mAb plus β-glucan-mediated tumoricidal activity. Treatment of mice with anti-Ly6G (anti-Gr-1) mAb has been previously reported to deplete granulocytes (neutrophils plus eosinophils) selectively with little or no effect on other leukocyte types (Wipke, B. T. and Allen, P. M., *J. Immunol.*, 167: 1601-1608 (2001)). However, the Gr-1 antigen is known to be expressed at lower levels on all myeloid cell populations including monocyte/macrophages and dendritic cells. Thus, it was important to demonstrate that the protocol used in this study was selective for granulocytes and did not deplete monocytes, macrophages or dendritic cells. Evaluation of blood and splenic leukocytes by flow cytometry confirmed the nearly complete depletion of peripheral granulocytes (FIGS. 24A and 24B). However, anti-Gr-1 treatment had very little effect on the population of Gr-1$^{high}$ granulocytes in the bone marrow. Presumably these cells are killed as soon as they exit from the marrow. Examination of peripheral blood by flow cytometry showed no depletion of Gr-1$^{low}$CD80$^+$ monocytes, whereas virtually all Gr-1$^{high}$CD80$^-$ neutrophils were missing (FIG. 24D). Tests of splenocytes showed no detectable depletion of Gr-1$^{low}$F4/80$^+$ macrophages (FIG. 24E) or Gr-1$^{low}$CD11c$^+$ dendritic cells (not shown). There was also no evidence for macrophage or dendritic cell depletion from bone marrow (not shown).

Figure 25:
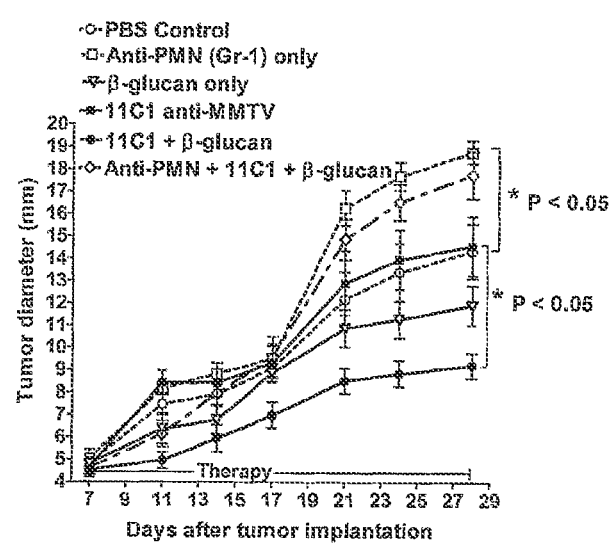
FIG. 25. is a graph showing the tumoricidal activity of immunotherapy with NSG β-glucan requires granulocytes and fails in mice depleted of granulocytes with anti-Gr-1 mAb. BALB/c mice were implanted with Ptas64 mammary carcinoma cells in a mammary fat pad and a tumor was allowed to form over 7 days before initiating immunotherapy. Mice were treated with 11C1 IgG2a anti-MMTV mAb and/or NSG β-glucan (400 μg daily) for a total period of 3 weeks. Granulocytes were depleted from some of the groups of mice as described in the Materials and Methods Section herein. As shown before with this tumor model (FIG. 17A, top panel), the combined use of soluble β-glucan produced significantly greater tumor regression than did treatment with 11C1 mAb only (P<0.05, lower bracket and asterisk). Mean values±SE of the mean are shown.

To determine the role of granulocytes in this form of tumor immunotherapy, mAb and β-glucan therapy of BALB/c mice with Ptas64 mammary tumors was carried out as before but mice were either untreated or granulocyte-depleted using anti-Gr-1 (FIG. 25). To prevent any complement depletion that might occur during the peak of complement-dependent granulocyte killing with the anti-Gr-1 mAb, mice were treated with the anti-Gr-1 i.p. three days prior to beginning mAb plus β-glucan therapy and then the mice were given additional i.v. injections of the anti-Gr-1 mAb at the same time as they were given the i.v. 11C1 therapeutic mAb. Serum complement levels were monitored at the beginning and during mAb plus β-glucan therapy by examining the ability of small serum samples from the mice to opsonize 11C1-opsonized Ptas64 cells in vitro with C3 as determined by staining with anti-mouse C3-FITC and flow cytometry. No evidence for complement depletion via the anti-Gr-1 treatment was obtained (not shown). Not only was the tumor regression mediated by mAb plus β-glucan completely abrogated by granulocyte depletion, but also the tumors in the granulocyte-depleted mice grew at a significantly faster rate than the tumors in the PBS control group during the last week of tumor measurements (FIG. 25). Thus, granulocytes (neutrophils and/or eosinophils) play an essential role in mediating tumor regression in therapy mediated by mAb plus β-glucan.

DISCUSSION

This investigation showed that both the tumor regression and increased survival mediated by monoclonal anti-tumor antibodies could be significantly enhanced if they were given in combination with β-glucan. The ability of β-glucan to enhance the activity of anti-tumor mAbs required that the mAbs activate complement and deposit iC3b on tumor cells for recognition by $CR3^+$ granulocytes.

Previous reports have shown that β-glucans functioned as a monotherapy through naturally-occurring anti-tumor antibodies that deposited iC3b on tumor cells, and that therapy was less effective in young mice that had lower levels of such natural anti-tumor antibodies. Therapy failed in mice with inherited severe combined immunodeficiency (that have no B and T lymphocytes, and cannot make natural antibodies), but could be reconstituted by i.v. injection of natural antibodies isolated from normal mouse sera. However, even in adult wild-type mice, tumor escape occurred when tumors lost the antigens recognized by naturally-occurring antibodies such that they were no longer targeted with iC3b.

In previous studies, β-glucan-mediated immunotherapy was thought to be enhanced by the coadministration of anti-tumor mAbs specific for a highly expressed and stable tumor antigen. The requirement that such mAbs activate complement was confirmed in experiments that demonstrated a failure of β-glucan to enhance mAb-mediated tumor regression or survival in C3-deficient mice. Others have also shown a lack of β-glucan enhancement of anti-tumor mAbs that did not activate complement (Cheung, N. K. and Modak, *Clin. Cancer Res.*, 8: 1217-1223 (2002)). Thus, β-glucan cannot enhance the therapeutic activity of humanized mAbs that have been engineered in such a way that they do not activate complement. The majority of humanized mAbs containing the human IgG1 Fc-region have been shown to activate complement, such as Herceptin™, Rituxan™, and Erbitux™ (Spiridon, C. I., et al., *Clin. Cancer Res.*, 8: 1720-1730 (2002), Idusogie, E. E., et al., *J. Immunol.*, 164: 4178-4184 (2000), Cragg, M. S., et al., *Blood*, 101: 1045-1052 (2003), Herbst, R. S. and Hong, W. K., *Semin. Oncol.*, 29: 18-30 (2002). With the exception of Rituxan, complement dependent cytotoxicity (CDC) does not represent a significant mechanism oftumoricidal activity with these mAbs and β-glucan does not alter the efficiency of CDC. Instead, β-glucan functions to prime granulocytes to kill tumor cells that have been targeted by mAb-mediated complement activation with surface-bound iC3b.

The EL-4 lymphoma was examined because of reports that it was resistant to therapy with mushroom-derived β-glucan (Takahashi, K., et al., *J. Pharmacobiodyn.*, 11: 472-478, 1988). This resistance was hypothesized to be due to an absence of naturally-occurring anti-tumor antibodies in the sera of its syngeneic C57B1/6 host (Yan, J., et al., *J. Immunol.*, 163:3045-3052(1999)). Therapy with 3F8 IgG3 anti-$G_{D2}$ ganglioside had been reported to be effective in protecting mice from an i.v. challenge with EL-4, but only if the mAb was given within 3 days after tumor challenge (Zhang, H., et al., *Cancer Res.*, 58: 2844-2849 (1998)). Unlike the majority of mouse tumors, EL-4 was shown to be very sensitive to CDC, as well as ADCC, mediated by 3F8 mAb. However, when 3F8 therapy was initiated 10 days after i.v. challenge, liver tumors formed that survived two weeks of i.v. therapy with 3F8 mAb. As expected, therapy with β-glucan alone had little effect on tumor growth, as tumors were not targeted with iC3b due to the lack of natural anti-tumor antibodies. However, giving mice 3F8 mAb in combination with β-glucan resulted in a significant enhancement of tumor regression compared to treatment with 3F8 mAb alone.

The RMA-S lymphoma resembles EL-4 in its high surface expression of $G_{D2}$ ganglioside tumor antigen and formation of liver tumors following i.v. challenge. However, RMA-S is completely resistant to CDC, although comparable to EL-4 in its sensitivity to ADCC (F. Hong, unpublished observation). RMA-S also differs from EL-4 in that normal C57B1/6 mouse sera contain naturally-occurring antibodies to RMA-S that opsonize the tumor with IgG and C3 in vivo, and that RMA-S is defective in peptide loading of MHC class I, thus preventing recognition by CD8 cytotoxic T cells.

An i.v. challenge with RMA-S produced liver tumors that survived two weeks of mAb therapy, even when therapy was initiated 5 days after tumor challenge. Although monotherapy with mAb did enhance survival, only the combined therapy with β-glucan produced long-term tumor-free survival.

Combining β-glucan with anti-tumor mAb was able to elicit a significant enhancement of tumor regression in 4 additional syngeneic tumor models in either BALB/c or C57B1/6 mice. The success of therapy in generating long-term survival appeared to depend on tumor antigen density and stability. Tumor escape was characterized by a loss of tumor antigen, resulting in tumor cells lacking the bound iC3b required for recognition by the β-glucan-primed CR3 of recruited granulocytes. With the RMA-S-MUC1 tumor model there was 80% long-term survival when the $G_{D2}$ tumor antigen was targeted with 14.G2a mAb, but only 20% survival when MUC1 was targeted with BCP8 mAb. Examination of tumors that escaped the combined BCP8 and β-glucan therapy showed that <25% of tumor cells continued to express MUC1 and bear membrane iC3b. This should not be a problem in targeting MUC1 on human tumors, as MUC1 is usually overexpressed and stable. It is particularly of interest to note that BCP8 anti-MUC1 mAb monotherapy had no effect on either tumor growth rate or survival from a challenge with MUC1-transfected Lewis lung carcinoma, and yet when BCP8 was used in combination with β-glucan it elicited significant tumor regression and long-term survival (FIGS. 21 and 22).

Previous reports that had studied tumor regression mediated by β-glucan without simultaneous mAb therapy had shown a requirement for both CR3 in a BALB/c tumor model and serum C3 in a 129/J tumor model (Yan, J., et al., *J. Immunol.*, 163:3045-3052(1999)). This investigation confirmed a similar role for CR3 and C3 in β-glucan enhanced mAb therapy in C57B1/6 mice that were examined for both tumor regression and long-term tumor-free survival.

In addition to CR3, others have recently reported the existence of a distinct type of macrophage β-glucan receptor known as dectin-1 (Brown, G. D., et al., *J. Exp. Med.*, 196: 407-412 (2002)). Dectin-1 was shown to be highly expressed on thioglycolate-elicited peritoneal macrophages, whereas much smaller amounts of dectin-1 were observed on resident peritoneal macrophages or granulocytes, and none was detectable on NK cells (Taylor, P. R., et al., *J. Immunol.*, 169: 3876-3882, (2002)). The current investigation does not exclude a function of dectin-1, but shows an absolute requirement for granulocyte CR3. Wild-type, but not CR3-deficient granulocytes, have been shown to bind NSG β-glucan, indicating that CR3 is the major receptor for soluble single-chain β-glucan on mouse granulocytes (Xia, Y., et. al., *J. Immunol.*, 162: 2281-2290 (1999)). CR3 is only required for recognition of soluble β-glucan by granulocytes, but also is needed for triggering cytotoxicity of tumors coated with the CR3 target ligand iC3b.

In vitro experiments have previously shown that soluble β-glucan was able to prime the CR3 of macrophages, neutrophils, and NK cells for cytotoxicity of iC3b-coated tumor cells (Vetvicka, V., et al., *J. Clin. Invest.*, 98: 50-61, 1996; Vetvicka, V., et al., *J. Immunol.*, 159: 599-605 (1997). The current investigation indicated that granulocytes were primarily responsible for β-glucan mediated tumor regression in vivo. Granulocytes are recruited by tumors independently of mAb and β-glucan therapy, perhaps because of natural antibody activation of complement within tumors that releases the potent chemotactic factor C5a. Flow cytometry analysis of tumor cell suspensions showed that Gr-1$^+$ granulocytes were the major CR3$^+$ leukocyte type within tumors, and depletion of granulocytes with anti-Gr-1 confirmed the major role of granulocytes in β-glucan mediated tumor regression.

An unexpected finding was that granulocytes appeared to play a role in tumor regression that was independent of mAb and β-glucan therapy. Tumors in granulocyte-depleted mice grew significantly faster than tumors in untreated control mice. Considering the leukocytosis that occurs in untreated mice with tumors, it appears possible that recruited granulocytes have some ability to kill tumor cells opsonized with natural antibody and iC3b, perhaps through C3-receptor enhanced ADCC since some of the natural anti-tumor antibody is IgG (Yan, J., et al., *J. Immunol.*, 163: 3045-3052 (1999).

In conclusion, this investigation showed that the therapeutic efficacy of anti-tumors antibodies (e.g., monoclonal) could be enhanced significantly by simultaneous administration of NSG, β-glucan. Furthermore, preliminary data have shown a similar enhancement of tumor regression when NSG is given in combination with tumor vaccines that generate anti-tumor antibodies (G. D. Ross, unpublished observation). NSG functions by recruiting granulocytes as tumor killer cells that are triggered via CR3 recognition of tumor cell-bound iC3b. This is a novel effector mechanism for anti-tumor mAb therapy that is additive to all other mechanisms of mAb-mediated tumor regression. As demonstrated with BCP8 anti-MUC1 mAb therapy of LL/2-MUC1, β-glucan can elicit significant regression and long-term survival, even with a mAb that has virtually no therapeutic effect on tumors when used as monotherapy. It is proposed that the previously reported inconsistent activity of NSG in cancer patients was likely due to the variable presence of natural or elicited anti-tumor antibodies. The current investigation demonstrates that NSG can generate a more consistent tumoricidal response if combined with an anti-tumor mAb. Considering the low incidence of side effects associated with NSG, the inclusion of β-glucan in antibody tumor therapy is a beneficial therapy.

Example 3

Orally administered barley β-glucan elicits tumor regression and survival that is similar to i.v. yeast β-glucan. As described in the Materials and Method Section above, groups of C57B1/6 mice were implanted s.c. with RMA-S-MUC1 and after 5 days to allow tumor formation were treated for 2 weeks with i.v. 14.G2a anti-GD2 ganglioside with or without simultaneous i.v. NSG yeast β-glucan or oral barley β-glucan. FIG. 26 describes the results. Mean values±SD are shown in FIG. 26.

While this invention has been particularly shown and described with references to preferred embodiments thereof, it will be understood by those skilled in the art that various changes in form and details may be made therein without departing from the scope of the invention encompassed by the appended claims.

What is claimed is:
1. A method of suppressing or eliminating non-Hodgkin's lymphoma, comprising administering a yeast neutral soluble glucan and rituximab to a subject having non-Hodgkin's lymphoma, wherein the glucan does not induce systemic release of inflammatory cytokines, and the glucan and rituximab together synergistically suppress or eliminate non-Hodgkin's lymphoma.
2. The method of claim 1, wherein the yeast neutral soluble beta glucan is administered parenterally.
3. The method of claim 1, wherein the yeast neutral soluble glucan is in a single helix conformation, a triple helix conformation, or a combination thereof.

* * * * *